(12) United States Patent
Scholz et al.

(10) Patent No.: US 6,348,476 B1
(45) Date of Patent: Feb. 19, 2002

(54) PHARMACEUTICAL COMBINATION PREPARATION OF AN INHIBITOR OF THE SODIUM/HYDROGEN EXCHANGER AND A MEDICAMENT FOR THE TREATMENT OF CARDIOVASCULAR DISEASES

(75) Inventors: Wolfgang Scholz, Eschborn; Udo Albus, Florstadt, both of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/610,425

(22) Filed: Jul. 5, 2000

Related U.S. Application Data

(63) Continuation of application No. 09/368,746, filed on Aug. 5, 1999, now abandoned, which is a continuation of application No. 09/139,385, filed on Aug. 25, 1998, now abandoned.

(30) Foreign Application Priority Data

Aug. 27, 1997 (DE) .......................................... 197 37 224

(51) Int. Cl.$^7$ .............................................. A61K 31/445
(52) U.S. Cl. ....................... 514/331; 514/183; 514/212; 514/237.8; 514/255; 514/275; 514/307; 514/311; 514/316; 514/400; 514/415; 514/427; 514/603; 514/604

(58) Field of Search ................................. 514/331, 183, 514/212, 237.8, 255, 275, 307, 311, 316, 400, 415, 427, 603, 604

(56) References Cited

U.S. PATENT DOCUMENTS 5,968,978 A * 10/1999 Kleeman et al. ............ 514/528

* cited by examiner

*Primary Examiner*—James H Reamer
(74) *Attorney, Agent, or Firm*—Finnegan, Henderson, Farabow, Garrett, & Dunner. L.L.P.

(57) ABSTRACT

Pharmaceutical combination preparation of an inhibitor of the sodium/hydrogen exchanger and a medicament for the treatment of cardiovascular diseases.

These combinations of an NHE inhibitor can comprise one or more therapeutically active compounds having cardiovascular activity. The combination of the cardioprotective properties with known therapies of cardiovascular diseases leads on the one hand to an improvement of the quality of the treatment and on the other hand in a large number of combinations to an additive or potentiated increase of the cardiovascular effects of the individual active compounds alone.

25 Claims, No Drawings

PHARMACEUTICAL COMBINATION PREPARATION OF AN INHIBITOR OF THE SODIUM/HYDROGEN EXCHANGER AND A MEDICAMENT FOR THE TREATMENT OF CARDIOVASCULAR DISEASES

This is a continuation of application Ser. No. 09/368,746, filed Aug. 5, 1999, now abandoned, which is a continuation of application Ser. No. 09/139,385 filed Aug. 25, 1998, now abandoned, which are incorporated herein by reference.

The invention relates to the combination of inhibitors of the sodium/hydrogen exchanger with other substances having cardiovascular activity for treating cardiovascular diseases.

Over the last years, inhibitors of the sodium/hydrogen exchanger (NHE) have been characterized in numerous preclinical studies as substances which, in cases of heart hypoperfusion, are suitable in a superior manner for preventing the destruction of the heart tissue at risk. The protection of the heart tissue by NHE inhibitors includes all manifestations of the damage caused by hypoperfusion, from arrhythmia, hypercontraction of the heart muscle and temporary loss of function up to necrosis of heart tissue and associated permanent damage.

The mechanism of action of the NHE inhibitors consists in a reduction of the increased sodium ion influx which is caused in hypoperfused tissues due to intracellular acidification and subsequent activation of the NHE. This results in a delay of the sodium overload of the tissue. Since sodium arm calcium ion transport are coupled in heart tissue, this also prevents the life-threatening calcium overload of the heart cells. This unique mechanism of action of the NHE inhibitors makes it possible to combine them in an advantageous manner with active compounds which are used for treating various cardiovascular diseases and whose cardiovascular action is based on a variety of mechanisms of action.

These combinations of an NHE inhibitor may comprise one or more active components having therapeutic vascular action. The combination of the heart-protecting properties with known therapies of cardiovascular diseases leads on the one hand to an improvement in the quality of the treatment and on the other hand in a large number of combinations to an additive or potentiated increase of the cardiovascular effects of the individual active components. In this context, the mechanistical prevention of sodium overload of the heart cells by the NHE inhibitors is particularly advantageous for the success of the treatment with the combination partner having cardiovascular activity.

The active compounds which are known and identified as NHE inhibitors are guanidine derivatives, preferably acylguanidines, inter alia such as described in the following publications and patent disclosures: Edward J. Cragoe, Jr., "DIURETICS, Chemistry, Pharmacology and Medicine", J. WILEY & Sons (1983), 303–341, additionally compounds of the following formulae:

I. (HOE 89/F 288—U.S. Pat. No. 5,292,755)

a) benzoylguanidines of the formula I

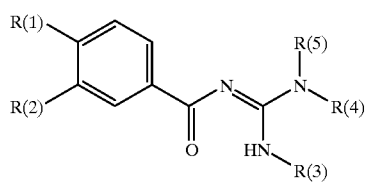

I in which:
R(1) is R(4)—$SO_m$ or R(5)R(6)N—$SO_2$—;
m is zero, 1 or 2;
R(4) and R(5) are $C_1$–$C_8$-alkyl, $C_3$–$C_6$-alkenyl or —$C_nH_{2n}$—R(7);
n is zero, 1, 2, 3 or 4;
R(7) is $C_5$–$C_7$-cycloalkyl or phenyl,
which is unsubstituted or substituted by 1–3 substituents selected from the group consisting of F, Cl, $CF_3$, methyl, methoxy and NR(8)R(9);
R(8) and R(9) are H or $C_1$–$C_4$-alkyl; or
R(5) is H;
R(6) is H or $C_1$–$C_4$-alkyl, or
R(5) and R(6) together are 4 or 5 methylene groups, of which one $CH_2$ group can be replaced by an O, S, NH, N—$CH_3$ or N-benzyl;
R(2) is hydrogen, F, Cl, Br, ($C_1$–$C_4$)-alkyl-, O—$(CH_2)_mC_pF_{2p+1}$ or —X—R(10);
m is zero or 1;
is 1, 2 or 3;

in which:
R(1) or R(2) is R(6)—$S(O)_n$— or R(7)R(8)N—$O_2S$—;
and the other substituent R(1) or R(2) in each case is H, F, Cl, Br, ($C_1$–$C_4$)-alkyl, ($C_1$–$C_4$)-alkoxy or phenoxy,
which is unsubstituted or substituted by 1–3 substituents selected from the group consisting of fluorine, chorine, methyl and methoxy;
or the other substituent R(1) or R(2) in each case is R(6)—$S(O)_n$ or R(7)R(8)N—;
n is zero, 1 or 2;
R(6) is ($C_1$–$C_6$)-alkyl, ($C_5$–$C_7$)-cycloalkyl, cyclopentylmethyl, cyclohexylmethyl or phenyl,
which is unsubstituted or substituted by 1–3 substituents selected from the group consisting of fluorine, chlorine, methyl and methoxy;
R(7) and R(8) identically or differently are H or ($C_1$–$C_6$)-alkyl; or
R(7) is phenyl-$(CH_2)_m$;
m is 1–4; or
R(7) is phenyl,
which is unsubstituted or substituted by 1–2 substituents selected from the group consisting of fluorine, chlorine, methyl and methoxy; or
R(7) and R(8) together are a straight-chain or branched ($C_4$–$C_7$)-chain, where the chain can additionally be interrupted by O, S or NR(9);
R(9) is H or methyl; or
R(7) and R(8) together with the nitrogen atom to which they are bonded, are a dihydroindole, tetrahydroquinoline or tetrahydroisoquinoline system;
R(3), R(4) and R(5) independently of one another are H or ($C_1$–$C_2$)-alkyl, or
R(3) and R(4) together are a ($C_2$–$C_4$)-alkylene chain; or
R(4) and R(5) together are a ($C_4$–$C_7$)-alkylene chain;
and their pharmaceutically tolerable salts;
(HOE 92/F 034—U.S. Pat. No. 5,373,924)

b) benzoylguanidines of the formula I

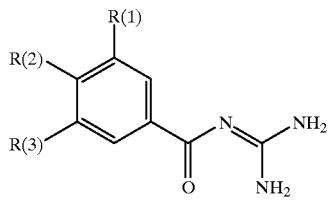

(I)

in which:
R(1) is R(4)—$SO_m$ or R(5)R(6)N—$SO_2$—;
m is zero, 1 or 2;
R(4) and R(5) are $C_1$–$C_8$-alkyl, $C_3$–$C_6$-alkenyl or —$C_nH_{2n}$—R(7);
n is zero, 1, 2, 3 or 4;
R(7) is $C_5$–$C_7$-cycloalkyl or phenyl,
which is unsubstituted or substituted by 1–3 substituents selected from the group consisting of F, Cl, $CF_3$, methyl, methoxy and NR(8)R(9);
R(8) and R(9) are H or $C_1$–$C_4$-alkyl; or
R(5) is H;
R(6) is H or $C_1$–$C_4$-alkyl, or
R(5) and R(6) together are 4 or 5 methylene groups, of which one $CH_2$ group can be replaced by an O, S, NH, N—$CH_3$ or N-benzyl;
R(2) is hydrogen, F, Cl, Br, ($C_1$–$C_4$)-alkyl-, O—$(CH_2)_mC_pF_{2p+1}$ or —X—R(10);
m is zero or 1;
is 1, 2 or 3;

X is O, S or NR(11);
R(10) is H, $C_1$–$C_6$-alkyl, $C_5$–$C_7$-cycloalkyl, cyclohexylmethyl, cyclopentylmethyl or —$C_nH_{2n}$—R(12);
n is zero, 1, 2, 3 or 4;
R(12) is phenyl,
which is unsubstituted or substituted by 1–3 substituents selected from the group consisting of F, Cl, $CF_3$, methyl, methoxy und NR(8)R(9);
R(8) and R(9) are H or $C_1$–$C_4$-alkyl;
R(11) is hydrogen or $C_1$–$C_3$-alkyl; or
R(10) and R(11) together are 4 or 5 methylene groups, of which one $CH_2$ group can be replaced by O, S, NH, N—$CH_3$ or N-benzyl;
R(3) is defined as R(1), or is $C_1$–$C_6$-alkyl, nitro, cyano, trifluoromethyl, F, Cl, Br, I or —X—R(10);
X is O, S or NR(11);
R(10) is H, $C_1$–$C_6$-alkyl, $C_5$–$C_7$-cycloalkyl, cyclohexylmethyl, cyclopentylmethyl or —$C_nH_{2n}$—R(12);
n is zero to 4;
R(12) is phenyl,
which is unsubstituted or substituted by 1–3 substituents selected from the group consisting of F, Cl, $CF_3$, methyl, methoxy und NR(8)R(9);
R(B) and R(9) are H or $C_1$–$C_4$-alkyl;
R(11) is $C_1$–$C_3$-alkyl, or
R(10) and R(11) together are 4 or 5 methylene groups, of which one $CH_2$ group can be replaced by O, S, NH, N—$CH_3$ or N-benzyl;
and their pharmaceutically tolerable salts;
(HOE 92/F 035 EP-Offenlegungsschrift 556 673)
c) ortho-substituted benzoylguanidines of the formula I

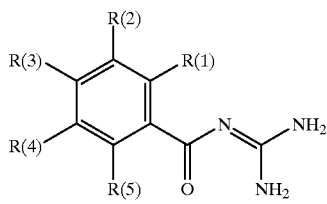

in which
R(1) is F, Cl, Br, I, $C_1$–$C_6$-alkyl or —X—R(6);
X is O, S, NR(7) or Y—ZO;
Y is 0 or NR(7);
Z is C or SO;
R(6) is H, $C_1$–$C_6$-alkyl, $C_5$–$C_7$-cycloalkyl, cyclohexylmethyl, cyclopentylmethyl, —$(CH_2)_mC_pF_{2p+1}$ or —$C_nH_{2n}$—R(8);
m is zero or 1;
p is 1–3;
n is zero to 4;
R(8) is phenyl,
which is unsubstituted or substituted by 1–3 substituents selected from the group consisting of F, Cl, $CF_3$, methyl, methoxy and NR(9)R(10);
R(9) and R(10) are H or $C_1$–$C_4$-alkyl;
R(7) is H or $C_1$–$C_3$-alkyl; or
R(6) and R(7) together are 4 or 5 methylene groups, of which one $CH_2$ group can be replaced by O, S, NH, N—$CH_3$ or N-benzyl;
R(3) is H or —X—R(6);
X is O, S, NR(7) or Y—ZO;
R(7) is H or $C_1$–$C_3$-alkyl;

Y is O or NR(7);
where Y is bonded to the phenyl radical of the formula I,
Z is C or SO;
R(6) is H, $C_1$–$C_6$-alkyl, $C_5$–$C_7$-cycloalkyl, cyclohexylmethyl, cyclopentylmethyl, —$(CH_2)_mC_pF_{2p+1}$ or —$C_nH_{2n}$—R(8);
m is zero or 1;
p is 1–3;
n is zero to 4;
R(8) is phenyl,
which is unsubstituted or substituted by 1–3 substituents selected from the group consisting of F, Cl, $CF_3$, methyl, methoxy and NR(9)R(10);
R(9) and R(10) are H or $C_1$–$C_4$-alkyl; or
R(6) and R(7) together are 4 or 5 methylene groups, of which one $CH_2$ group can be replaced by O, S, NH, N—$CH_3$ or N-benzyl;
R(2) and R(4) identically or differently are R(11)—$SO_q$— or R(12)R(13)N—$SO_2$—;
q is zero–2;
R(11) is $C_1$–$C_4$-alkyl,
which is unsubstituted or carries phenyl as a substituent, where phenyl is unsubstituted or substituted by 1–3 substituents selected from the group consisting of F, Cl, $CF_3$, methyl, methoxy and NR(9)R(10);
R(9) and R(10) are H or $C_1$–$C_4$-alkyl;
R(12) and R(13) are defined as R(6) and R(7);
or one of the two radicals R(2) or R(4) is hydrogen or is defined as R(1);
R(5) is H, methyl, F, Cl or methoxy,
and their pharmaceutically tolerable salts;
(HOE 92/F 036—U.S. Pat. No. 5,364,868)
d) benzoylguanidines of the formula I

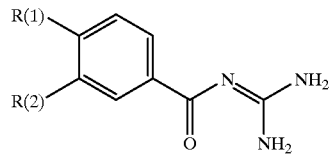

in which:
R(1) or R(2) is an amino group —NR(3)R(4);
R(3) and R(4) identically or differently are H, $C_1$–$C_6$-alkyl or $C_3$–$C_7$-cycloalkyl; or
R(3) is phenyl-$(CH_2)_p$—;
p is 0, 1, 2, 3 or 4; or
R(3) is phenyl,
where the phenyl in each case is unsubstituted or carries one to two substituents selected from the group consisting of fluorine, chlorine, methyl and methoxy; or
R(3) and R(4) together can be a straight-chain or branched $C_4$–$C_7$-methylene chain, where one —$CH_2$— member of the methylene chain can be replaced by oxygen, S or NR(5);
R(5) is H or lower alkyl;
the other substituent R(1) or R(2) in each case is H, F, Cl, $C_1$–$C_4$-alkyl, $C_1$–$C_4$-alkoxy, $CF_3$, $C_mF_{2m+1}$—$CH_2$—, benzyl or phenoxy,
where the respective phenyl radical is unsubstituted or carries one to two substituents selected from the group consisting of methyl, methoxy, fluorine and chlorine;

m is 1, 2 or 3;
and their pharmaceutically tolerable salts;
(92/F 197 K—NZ 248 013)

e) benzoylguanidines of the formula I

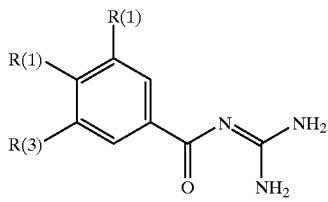

(I)

in which:

R(1) is R(4)—SO$_m$ or R(5)R(6)N—SO$_2$—;
m is zero, 1 or 2;
R(4) and R(5) are C$_1$–C$_8$-alkyl, C$_3$–C$_6$-alkenyl or —C$_n$H$_{2n}$—R(7);
n is zero, 1, 2, 3 or 4;
R(7) is C$_5$–C$_7$-cycloalkyl or phenyl,
which is unsubstituted or substituted by 1–3 substituents selected from the group consisting of F, Cl, CF$_3$, methyl, methoxy and NR(8)R(9);
R(8) and R(9) are H or C$_1$–C$_4$-alkyl; or
R(5) is H;
R(6) is H or C$_1$–C$_4$-alkyl; or
R(5) and R(6) together are 4 or 5 methylene groups, of which one CH$_2$ group can be replaced by an O, S, NH, N—CH$_3$ or N-benzyl;
R(2) is hydrogen, straight-chain or branched (C$_1$–C$_8$)-alkyl, —CR(13)=CHR(12) or —C≡CR(12);
R(12) is phenyl,
which is unsubstituted or substituted by 1–3 substituents selected from the group consisting of F, Cl, CF$_3$, methyl, methoxy and NR(14)R(15);
R(14) and R(15) are H or (C$_1$–C$_4$)-alkyl; or
R(12) is (C$_1$–C$_9$)-heteroaryl,
which is unsubstituted or substituted as phenyl, or
R(12) is (C$_1$–C$_6$)-alkyl,
which is unsubstituted or substituted by 1–3 OH, or
R(12) is (C$_3$–C$_8$)-cycloalkyl;
R(13) is hydrogen or methyl, or
R(12) is (C$_3$–C$_8$)-cycloalkyl, (C$_3$–C$_8$)-cycloalkyl-(C$_1$–C$_4$)-alkyl, phenyl, C$_6$H$_5$—(C$_1$–C$_4$)-alkyl, naphthyl, biphenylyl, 1,1-diphenyl-(C$_1$–C$_4$)-alkyl, cyclopentadienyl, pyridyl, pyrrolyl, furanyl, thienyl, thiazolyl, oxazolyl, indenyl, quinolyl, indolyl, benzofuranyl, benzothienyl, benzothiazolyl, benzoxazolyl, imidazolyl, pyrazolyl, triazolyl, tetrazolyl, isoxazolyl, isothiazolyl, pyrazinyl, pyrimidinyl, pyridazinyl, indazolyl, isoquinolyl, phthalazinyl, quinoxalinyl, quinazolinyl or cinnolinyl;
R(3) is defined as R(2);
and where the aromatic substituents R(2) and R(3) are unsubstituted or substituted by 1–3 substituents from the groups F, Cl, CF$_3$, (C$_1$–C$_4$-alkyl or -alkoxy, or NR(10)R(11) with R(10) and R(11) being H or (C$_1$–C$_4$)-alkyl;
and their pharmaceutically tolerable salts;
(HOE 92/F 303 K—EP-Offenlegungsschrift 589 336, NZ 248 703)

f) benzoylguanidines of the formula I

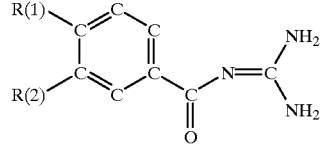

I in which:
R(1) or R(2) is R(3)—S(O)$_n$— or

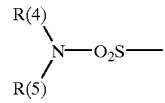

the other substituent R(1) or R(2) in each case is H, OH, F, Cl, Br, I, C$_1$–C$_4$-alkyl, C$_1$–C$_4$-alkoxy, benzyloxy or phenoxy,
which is unsubstituted or carries one to three substituents selected from the group consisting of fluorine, chlorine, methyl, methoxy, hydroxyl and benzyloxy, R(3)—S(O)$_n$, —NR(4)R(5) or 3,4dehydropiperidine
R(3) is C$_1$–C$_6$-alkyl, C$_5$–C$_7$-cycloalkyl, cyclopentylmethyl, cyclohexylmethyl or phenyl,
which is unsubstituted or substituted by one to three substituents selected from the group consisting of fluorine, chlorine, methyl and methoxy;
R(4) and R(5) identically or differently, are H or C$_1$–C$_6$-alkyl; or
R(4) is phenyl-(CH$_2$)$_m$—;
m is 1, 2, 3 or 4; or
R(4) is phenyl,
which is unsubstituted or carries one to two substituents selected from the group consisting of fluorine, chlorine, methyl and methoxy; or
R(4) and R(5) together are a straight-chain or branched C$_4$–C$_7$-chain, where the chain can additionally be interrupted by O, S or NR(6),
R(6) is H or methyl; or
R(4) and R(5) together with the nitrogen atom to which they are bonded, are a dihydroindole, tetrahydroquinoline or tetrahydroisoquinoline system;
n is zero, 1 or 2;
and their pharmaceutically tolerable salts;
(921F 304—U.S. Pat. No. 5,416,094)

g) isoquinolines of the formula I

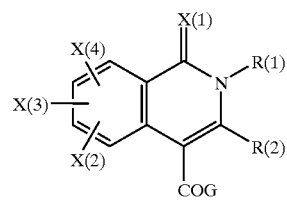

I in which:
R(1) is hydrogen, alkyl, cycloalkyl, arylalkyl, alkenyl, substituted aminoalkyl or an aryl or heteroaryl ring;
where the rings are unsubstituted or substituted by 1–3 groups selected from the group consisting of halogen, nitro, amino, mono(lower alkyl)amino, di(lower alkyl) amino, lower alkyl, lower alkoxy, benzyloxy, phenoxy, hydroxyl, trifluoromethyl, R(2) is hydrogen, halogen, alkyl or aryl;
which is unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl,

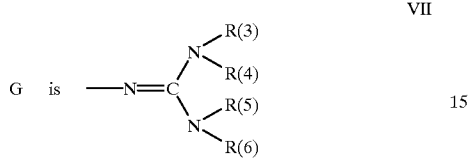

(VII)

X(2), X(3) and X(4) independently of one another are hydrogen, halogen, nitro, amino, alkyl, sulfonamide, mono(lower alkyl)amino, di(lower alkyl)amino, lower alkyl, benzyloxy, hydroxyl;

X(1) is hydrogen, oxygen, sulfur or NR(7);
R(7) is hydrogen, alkyl, cycloalkyl, arylalkyl, alkenyl, substituted aminoalkyl or an aryl or a heteroaryl ring; which rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl and trifluoromethyl;
in which substituents each alkyl chain or alkenyl chain can be interrupted by oxygen, sulfur or NR(8);
R(8) is hydrogen, alkyl, cycloalkyl, arylalkyl, alkenyl, substituted aminoalkyl or an aryl or heteroaryl ring, which rings are unsubstituted or substituted by 1–3 groups selected from the group consisting of halogen, nitro, amino, mono(lower alkyl)amino, di(lower alkyl) amino, lower alkyl, lower alkoxy, benzyloxy, phenoxy, hydroxyl arid trifluoromethyl;

and their pharmaceutically acceptable salts;
(92/F 404—EP 602 522, NZ 250 438)

h) compounds of the formula I

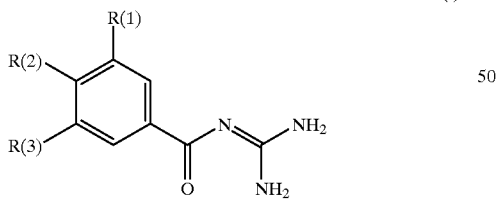

(I)

in which:
R(1) is hydrogen, F, Cl, Br, I, —NO$_2$, —C≡N, —CF$_3$, R(4)—SO$_m$ or R(5)R(6)N—SO$_2$—;
m is zero, 1 or 2;
R(4) and R(5) are (C$_1$–C$_8$)-alkyl, (C$_3$–C$_6$)-alkenyl, —C$_n$H$_{2n}$—R(7) or CF$_3$;
n is zero, 1, 2, 3 or 4;
R(7) is (C$_3$–C$_7$)-cycloalkyl or phenyl,
which is not substituted or is substituted by 1–3 substituents selected from the group consisting of F, Cl, CF$_3$, methyl, methoxy and NR(8)R(9);

R(8) and R(9) are H or C$_1$–C$_4$-alkyl; or
R(5) is H;
R(6) is H or (C$_1$–C$_4$)-alkyl; or
R(5) and R(6) together are 4 or 5 methylene groups, of which one CH$_2$ group can be replaced by oxygen, S, NH, N—CH$_3$ or N-benzyl;
R(2) is —SR(10), —OR(10), —NHR(10), —NR(10)R (11), —CHR(10)R(12), —[CR(12)R(13)OR(13')], —{C—[CH$_2$—OR(13')]R(12)R(13)} or —[CR(18)R (17)]$_p$—(CO)—[CR(19)R(20)]$_q$—R(14);
R(10), R(11) identically or differently are —[CHR(16)]$_s$—(CH$_2$)$_p$—(CHOH)$_q$—(CH$_2$)$_r$—(CH OH)$_t$—R(21) or —(CH$_2$)$_p$—O—(CH$_2$—CH$_2$O)$_q$—R(21),
R(21) is hydrogen, methyl,
p, q, r identically or differently are zero, 1, 2, 3 or 4;
s is zero or 1;
t is 1, 2, 3 or 4;
R(12) and R(13) identically or differently are hydrogen, (C$_1$–C$_6$)-alkyl or, together with the carbon atom carrying them, are a (C$_3$–C$_8$)-cycloalkyl,
R(13') is hydrogen or (C$_1$–C$_4$)-alkyl;
R(14) is H, (C$_1$–C$_6$)-alkyl, (C$_3$–C$_8$)-cycloalkyl or —C$_a$H$_{2a}$—R(15);
a is zero, 1, 2, 3 or 4;
R(15) is phenyl,
which is unsubstituted or substituted by 1–3 substituents selected from the group consisting of F, Cl, CF$_3$, methyl, methoxy and NR(8)R(9);
R(8) and R(9) are H or (C$_1$–C$_4$)-alkyl; or
R(15) is (C$_1$–C$_9$)-heteroaryl,
which is unsubstituted or substituted as phenyl, or
R(15) is (C$_1$–C$_6$)-alkyl,
which is unsubstituted or substituted by 1–3 OH;
R(16), R(17), R(18), R(19) and R(20) are hydrogen or (C$_1$–C$_3$)-alkyl;
R(3) is defined as R(1), or
R(3) is (C$_1$–C$_6$)-alkyl or —X—R(22);
X is oxygen, S or NR(16);
R(16) is H or (C$_1$–C$_3$)-alkyl; or
R(22) and R(16) together are 4 or 5 methylene groups, of which one CH$_2$ group can be replaced by oxygen, S, NH, N—CH$_3$ or N-benzyl;
R(22) is defined as R(14);

and their pharmaceutically tolerable salts;
(HOE 92/F 405—EP 602 523, NZ 250 437)

i) benzoylguanidines of the formula I

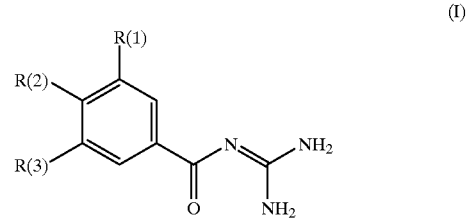

(I)

in which:
R(1) is hydrogen, F, Cl, Br, I, —NO$_2$, —C≡N, R(16)—C$_p$H$_{2p}$—O$_q$, R(4)—SO$_m$ or R(5)R(6)N—SO$_2$—;
m is zero, 1 or 2;
p is zero or 1;
q is zero, 1, 2 or 3;
R(16) is C$_r$F$_{2r+1}$;
r is 1, 2 or 3;
R(4) and R(5) are (C$_1$–C$_8$)-alkyl, (C$_3$–C$_6$)-alkenyl, —C$_n$H$_{2n}$—R(7) or CF$_3$;

n is zero, 1, 2, 3 or 4;
R(7) is $(C_3-C_7)$-cycloalkyl or phenyl,
which is not substituted or is substituted by 1–3 substituents selected from the group consisting of F, Cl, $CF_3$, methyl, methoxy and NR(8)R(9);
R(8) and R(9) are H or $C_1-C_4$-alkyl; or
R(5) is H;
R(6) is H or $(C_1-C_4)$-alkyl; or
R(5) and R(6) together are 4 or 5 methylene groups, of which one $CH_2$ group can be replaced by oxygen, S, NH, N—$CH_3$ or N-benzyl,
R(2) is $(C_1-C_9)$-heteroaryl,
which is linked via C or N and which is unsubstituted or substituted by 1–3 substituents selected from the group consisting of F, Cl, $CF_3$, $CH_3$, methoxy, hydroxyl, amino, methylamino and dimethylamino; or
R(2) is —SR(10), —OR(10), —NR(10)R(11), —CR(10)R(11)R(12);
R(10) is —$C_aH_{2a}$—$(C_1-C_9)$-heteroaryl,
which is unsubstituted or substituted by 1–3 substituents selected from the group consisting of F, Cl, $CF_3$, $CH_3$, methoxy, hydroxyl, amino, methylamino and dimethylamino;
a is zero, 1 or 2;
R(11) and R(12) independently of one another are defined as R(10) or are hydrogen or $(C_1-C_4)$-alkyl;
R(3) is defined as R(1), or is $(C_1-C_8)$-alkyl or —X—R(13);
X is oxygen, S, or NR(14);
R(14) is H or $(C_1-C_3)$-alkyl;
R(13) is H, $(C_1-C_6)$-alkyl, $(C_3-C_8)$-cycloalkyl or —$C_bH_{2b}$—R(15);
b is zero, 1, 2, 3 or 4; or
R(13) and R(14) together are 4 or 5 methylene groups, of which one $CH_2$ group can be replaced by oxygen, S, NH, N—$CH_3$ or N-benzyl;
R(15) is phenyl,
which is unsubstituted or substituted by 1–3 substituents selected from the group consisting of F, Cl, $CF_3$, methyl, methoxy and NR(8)R(9);
R(8) and R(9) are H or $(C_1-C_4)$-alkyl;
and their pharmaceutically tolerable salts;
(HOE 92/F 411—NZ 250 450, EP 603 650)
k) benzoylguanidines of the formula I

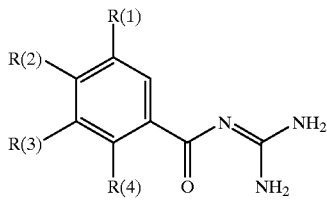

in which:
one of the substituents R(1), R(2), R(3) or R(4)

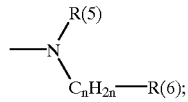

R(5) is hydrogen or $C_{(1-6)}$-alkyl;
n is zero, 1, 2, 3 or 4;
R(6) is H or $C_{(1-4)}$-alkyl;

in which one $CH_2$ group can be replaced by 1 sulfur atom or a group NR(7);
R(7) is hydrogen, methyl or ethyl; or
R(6) is $C_{(3-8)}$-cycloalkyl or phenyl,
which is unsubstituted or carries 1, 2 or 3 substituents selected from the group consisting of F, Cl, Br, methyl, methoxy, —NR(8)R(9);
R(8) and R(9) are H, methyl or ethyl; or
R(5) and R(6) together with the nitrogen atom are a 5-, 6- or 7-membered ring, in which 1 carbon atom can be replaced by oxygen, S or NR(10);
R(10) is H, $C_{(1-3)}$-alkyl or benzyl;
and the other substituents R(1), R(2), R(3), R(4) in each case are:
hydrogen, F, Cl, Br, I, CN, $CF_3$, $NO_2$, $CF_3$—O—, $C_mF_{2m+1}$—$CH_2$—O— or R(11)—$C_qH_{2q}$—$X_p$—;
m is 1, 2 or 3;
q is zero, 1, 2, 3 or 4;
p is zero or 1;
X is oxygen or NR(12);
R(12) is H or $C_{(1-3)}$-alkyl;
R(11) is hydrogen, $C_{(1-6)}$-alkyl, $C_{(3-8)}$-cycloalkyl or phenyl,
which is unsubstituted or substituted by 1, 2 or 3 substituents selected from the group consisting of F, Cl, $CH_3$, $CH_3$—O— and NR(13)R(14);
R(13), R(14) are H, methyl or ethyl;
and their pharmaceutically tolerable salts;
(HOE 92/F 422—EP 604 852)
l) benzoylguanidines of the formula I

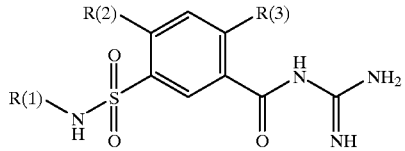

in which:
R(1) is R(4)R(5)N—C(X)—;
X is oxygen, S or N—R(6);
R(4) and R(5) identically or differently, are H, $(C_1-C_8)$ alkyl, $(C_3-C_6)$-alkenyl or —$C_nH_{2n}$—R(7);
n is zero, 1, 2, 3 or 4;
R(7) is $(C_5-C_7)$-cycloalkyl or phenyl,
which is unsubstituted or substituted by 1–3 substituents selected from the group consisting of F, Cl, $CF_3$, methoxy and $(C_1-C_4)$-alkyl; or
R(4) and R(5) together are 4 or 5 methylene groups, of which one $CH_2$ group can be replaced by oxygen, S, NH, N—$CH_3$ or N-benzyl;
R(6) is defined as R(4) or is amidine;
R(2) is H, F, Cl, Br, I, $(C_1-C_8)$-alkyl, 1-alkenyl or 1-alkynyl, $(C_3-C_8)$-cycloalkyl, $(C_3-C_8)$-cycloalkyl-$(C_1-C_4)$-alkyl, phenyl, $C_6H_5$—$(C_1-C_4)$-alkyl, naphthyl, biphenylyl, 1,1-diphenyl-$(C_1-C_4)$-alkyl, cyclopentadienyl, pyridyl, thiopyridyl, pyrrolyl, furanyl, thienyl, thiazolyl, oxazolyl, indenyl, quinolyl, indolyl, benzofuranyl, benzothienyl, benzothiazolyl, benzoxazolyl or —W—R(8);
W is oxygen, S or NR(9);
R(8) is H, $(C_1-C_6)$-alkyl, $(C_5-C_7)$-cycloalkyl, cyclohexylmethyl, cyclopentylmethyl, —$(CH_2)_mC_pF_{2p+1}$ or —$C_qH_{2q}$—R(10);
m is zero or 1;
p is 1, 2 or 3;

q is zero, 1, 2, 3 or 4;
R(10) is phenyl,
which is unsubstituted or substituted by 1–3 substituents selected from the group consisting of F, Cl, $CF_3$, methyl, methoxy and NR(11)R(12);
R(11) and R(12) are H or $(C_1-C_4)$-alkyl;
R(9) is H or $(C_1-C_3)$-alkyl; or
R(8) and R(9) together are 4 or 5 methylene groups, of which one $CH_2$ group can be replaced by oxygen, S, NH, N—$CH_3$ or N-benzyl;
R(3) is H, F, Cl, Br, I, $(C_1-C_6)$-alkyl or —W—R(8) as defined for R(2),
and their pharmaceutically acceptable salts;
(93/F 054—NZ 250 919, EP-Offenlegungsschrift 612 723)

m) benzoylguanidines of the formula I

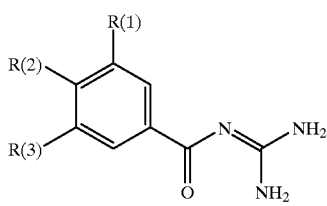

(I)

in which:
R(1), R(2), R(3) are hydrogen, F, Cl, Br, I or $(C_1-C_{12})$-alkyl;
one of the substituents R(1), R(2) and R(3) is $N_3$, CN, OH or $(C_1-C_{10})$-alkyloxy, if at least one of the remaining substituents R(1), R(2) or R(3) is a sufficiently lipophilic alkyl radical having 3 to 12 carbon atoms; or
one of the substituents R(1), R(2) and R(3) is R(4)—$C_nH_{2n}$—$O_m$—;
m is zero or 1;
n is zero, 1, 2 or 3;
R(4) is $C_pF_{2p+1}$;
p is 1, 2 or 3, if n is zero or 1; or
R(4) is $(C_3-C_{12})$-cycloalkyl, phenyl, pyridyl, quinolyl or isoquinolyl,
where the aromatic and heteroaromatic ring systems are unsubstituted or substituted by a substituent selected from the group consisting of F, Cl, $CF_3$, methyl, methoxy and NR(5)R(6);
R(5) and R(6) are hydrogen or $(C_1-C_4)$-alkyl;
or one of the substituents R(1), R(2) and R(3) is —C≡CR(5) or —C[R(6)]=CR(5);
R(5) is phenyl,
which is unsubstituted or substituted by 1–3 substituents selected from the group consisting of F, Cl, $CF_3$, methyl, methoxy, hydroxyl, amino, methylamino and dimethylamino, $(C_1-C_9)$-heteroaryl,
which is unsubstituted or substituted as phenyl, or
R(5) is $(C_1-C_6)$-alkyl,
which is unsubstituted or substituted by 1–3 OH; or
R(5) is $(C_3-C_8)$-cycloalkyl,
R(6) is hydrogen or methyl;
and their pharmacologically acceptable salts;
(93/F 153—EP-Offenlegungsschrift 627 413, NZ 260 660)

o) benzoylguanidines of the formula I

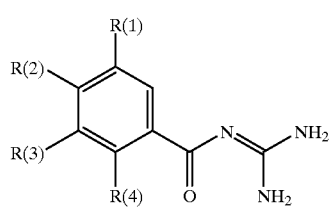

(I)

in which:
R(1) is hydrogen, F, Cl, Br, I, —$NO_2$, —C≡N, $X_o$—$(CH_2)_p$—$(CF_2)_q$—$CF_3$, R(5)—$SO_m$, R(6)—CO— or R(6)R(7)N—$SO_2$—, where
X is oxygen, S or NR(14);
m is zero, 1 or 2;
o is zero or 1;
p is zero, 1 or 2;
q is zero, 1, 2, 3, 4, 5 or 6;
R(5) and R(6) are $(C_1-C_8)$-alkyl, $(C_3-C_6)$-alkenyl, —$C_nH_{2n}$—R(8) or $CF_3$;
n is zero, 1, 2, 3 or 4;
R(8) is $(C_3-C_7)$-cycloalkyl or phenyl,
which is not substituted or is substituted by 1–3 substituents selected from the group consisting of F, Cl, $CF_3$, methyl, methoxy and NR(9)R(10);
R(9) and R(10) are H or $C_1-C_4$-alkyl; or
R(6) is H;
R(7) is H or $(C_1-C_4)$-alkyl; or
R(6) and R(7) together are 4 or 5 methylene groups, of which one $CH_2$ group can be replaced by oxygen, S, NH, N—$CH_3$ or N-benzyl;

R(2) is —Y—⟨phenyl⟩—$(C)_h$—$(CHOH)_i$—$(CH_2)_j$—$(CHOH)_k$—R(11)

or —Y—⟨phenyl⟩—$(C)_h$—$(CHOH)_i$—$(CH_2)_j$—$(CHOH)_k$—R(11)

or ⟨phenyl⟩—$(C)_h$—$(CHOH)_i$—$(CH_2)_j$—$(CHOH)_k$—R(11)
      Y—

Y is oxygen, —S— or —NR(12)—;
R(11) and R(12) are hydrogen or $(C_1-C_3)$-alkyl;
h is zero or 1;
i, j and k independently are zero, 1, 2, 3 or 4;
but where h, i and k are not simultaneously zero,
R(3) is defined as R(1), or is $(C_1-C_6)$-alkyl or —X—R(13);
X is oxygen, S or NR(14);
R(14) is H or $(C_1-C_3)$-alkyl;
R(13) is H, $(C_1-C_6)$-alkyl, $(C_3-C_8)$-cycloalkyl or —$C_bH_{2b}$—R(15);
b is zero, 1, 2, 3 or 4; or
R(13) and R(14) together are 4 or 5 methylene groups, where one $CH_2$ group can be replaced by oxygen, S, NH, N—$CH_3$ or N-benzyl;
R(15) is phenyl,
which is unsubstituted or substituted by 1–3 substituents selected from the group consisting of F, Cl, $CF_3$, methyl, methoxy and NR(9)R(10);

R(9) and R(10) are H or (C$_1$–C$_4$)-alkyl;
R(4) is hydrogen, —OR(16) or —NR(16)R(17);
R(16) and R(17) independently are hydrogen or (C$_1$–C$_3$)-alkyl;
and their pharmaceutically tolerable salts;
(HOE 93/F 154—EP-Offenlegungsschrift 628 543, NZ 260 681)
p) benzoylguanidines of the formula I

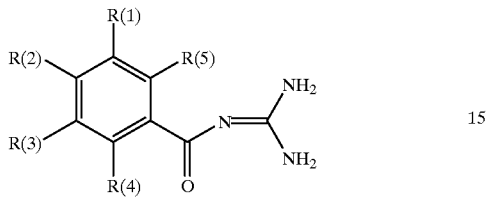

in which:
R(1) is R(6)—CO or R(7)R(8)N—CO;
R(6) is (C$_1$–C$_8$)-alkyl, (C$_1$–C$_8$)-perfluoroalkyl, (C$_3$–C$_8$)-alkenyl or —C$_n$H$_{2n}$—R(9);
n is zero, 1, 2, 3 or 4;
R(9) is (C$_3$–C$_8$)-cycloalkyl, phenyl, biphenylyl or naphthyl,
where the aromatics are not substituted or are substituted by 1–3 substituents selected from the group consisting of F, Cl, CF$_3$, methyl, methoxy and NR(10)R(11);
R(10) and R(11) are H, (C$_1$–C$_4$)-alkyl or (C$_1$–C$_4$) perfluoroalkyl;
R(7) is H, (C$_1$–C$_8$)-alkyl, (C$_1$–C$_8$)-perfluoroalkyl, (C$_3$–C$_8$)-alkenyl or —C$_n$H$_{2n}$—R(12);
n is zero, 1, 2, 3 or 4;
R(12) is (C$_3$–C$_8$)-cycloalkyl, phenyl, biphenylyl or naphthyl,
where the aromatics are not substituted or are substituted by 1–3 substituents selected from the group consisting of F, Cl, CF$_3$, methyl, methoxy and NR(13)R(14);
R(13) and R(14) are H, (C$_1$–C$_4$)-alkyl or (C$_1$–C$_4$)-perfluoroalkyl;
R(8) is H, (C$_1$–C$_4$)-alkyl or (C$_1$–C$_4$)-perfluoroalkyl; or
R(7) and R(8) together are 4 or 5 methylene groups, of which one CH$_2$ group can be replaced by oxygen, S, NH, N—CH3 or N-benzyl;
R(2) is defined as R(1), or is H, F, Cl, Br, I, CN, NO$_2$, (C$_1$–C$_8$)-alkyl, (C$_1$–C$_8$)-perfluoroalkyl, (C$_3$–C$_8$)-alkenyl or —C$_n$H$_{2n}$R(15);
n is zero 1, 2, 3, 4;
R(15) is (C$_3$–C$_8$)-cycloalkyl, phenyl, biphenylyl or naphthyl,
where the aromatics are not substituted or are substituted by 1–3 substituents selected from the group consisting of F, Cl, CF$_3$, methyl, methoxy and NR(16)R(17);
R(16) and R(17) are H, (C$_1$–C$_4$)-alkyl or (C$_1$–C$_4$)-perfluoroalkyl; or
R(2) is (C$_1$–C$_9$)-heteroaryl,
which is linked via C or N and which is unsubstituted or substituted by 1–3 substituents selected from the group consisting of F, Cl, CF$_3$, CH$_3$, methoxy, hydroxyl, amino, methylamino and dimethylamino; or
R(2) is SR(18), —OR(18), —NR(18)R(19), —CR(18)R(19)R(20);
R(18) is —C$_a$H$_{2a}$—(C$_1$–C$_9$)-heteroaryl,
which is unsubstituted or substituted by 1–3 substituents selected from the group consisting of F, Cl, CF$_3$, CH$_3$, methoxy, hydroxyl, amino, methylamino and dimethylamino;
a is zero, 1 or 2;
R(19) and R(20) independently of one another are defined as R(18) or are hydrogen, (C$_1$–C$_4$)-alkyl or (C$_1$–C$_4$)-perfluoroalkyl; or
R(2) is R(21)—SO$_m$ or R(22)R(23)N—SO$_2$—;
m is 1 or 2;
R(21) is (C$_1$–C$_8$)-alkyl, (C$_1$–C$_8$)-perfluoroalkyl, (C$_3$–C$_8$)-alkenyl, —C$_n$H$_{2n}$—R(24),
n is zero, 1, 2, 3 or 4;
R(24) is (C$_3$–C$_8$)-cycloalkyl, phenyl, biphenylyl or naphthyl,
where the aromatics are not substituted or are substituted by 1–3 substituents selected from the group consisting of F, Cl, CF$_3$, methyl, methoxy and NR(27)R(28);
R(27) and R(28) are H, (C$_1$–C$_4$)-alkyl or (C$_1$–C$_4$)-perfluoroalkyl;
R(22) is H, (C$_1$–C$_8$)-alkyl, (C$_1$–C$_8$)-perfluoroalkyl, (C$_3$–C$_8$)-alkenyl, —C$_n$H$_{2n}$—R(29);
n is zero, 1, 2, 3 or 4;
R(29) is (C$_3$–C$_8$)-cycloalkyl, phenyl, biphenylyl or naphthyl,
where the aromatics are not substituted or are substituted by 1–3 substituents selected from the group consisting of F, Cl, CF$_3$, methyl, methoxy and NR(30)R(31);
R(30) and R(31) are H, (C$_1$–C$_4$)-alkyl or (C$_1$–C$_4$)-perfluoroalkyl;
R(23) is H, (C$_1$–C$_4$)-alkyl or (C$_1$–C$_4$)-perfluoroalkyl; or
R(22) and R(23) together are 4 or 5 methylene groups, of which one CH$_2$ group can be replaced by oxygen, S, NH, N—CH$_3$ or N-benzyl; or
R(2) is R(33)X—;
X is oxygen, S, NR(34), (D=O)A—, NR(34)C=MN$^{(*)}$R(35)—;
M is oxygen or S;
A is oxygen or NR(34);
D is C or SO;
R(33) is (C$_1$–C$_8$)-alkyl, (C$_3$–C$_8$)-alkenyl, (CH$_2$)$_b$C$_d$F$_{2d+1}$, —C$_n$H$_{2n}$—R(36),
b is zero or 1;
d is 1, 2, 3, 4, 5, 6 or 7;
n is zero, 1, 2, 3 or 4;
R(36) is (C$_3$–C$_8$)-cycloalkyl, phenyl, biphenylyl or naphthyl,
where the aromatics are not substituted or are substituted by 1–3 substituents selected from the group consisting of F, Cl, CF$_3$, methyl, methoxy and NR(37)R(38);
R(37) and R(38) are H, (C$_1$–C$_4$)-alkyl or (C$_1$–C$_4$)-perfluoroalkyl;
R(34) is H, (C$_1$–C$_4$)-alkyl or (C$_1$–C$_4$)-perfluoroalkyl;
R(35) is defined as R(33); or
R(33) and R(34) together are 4 or 5 methylene groups, of which one CH$_2$ group can be replaced by oxygen, S, NH, N—CH$_3$ or N-benzyl;
where A and N$^{(*)}$ are bonded to the phenyl nucleus of the benzoylguanidine parent structure; or
R(2) is —SR(40), —OR(40), —NHR(40), —NR(40)R(41), —CHR(40)R(42), —C[R(42)R(43)OH], —C≡CR(45), —CR(46)=CHR(45), —[CR(47)R(48)]$_u$—(CO)—[CR49)R(50)]$_v$—R(44);

R(40), R(41) identically or differently are —(CH₂)ₚ—(CHOH)_q—(CH₂)_r—(CHOH)_t—R(51) or —(CH₂)ₚ—O—(CH₂—CH₂O)_q—R(51);
R(51) is hydrogen or methyl;
u is 1, 2, 3 or 4;
v is zero, 1, 2, 3 or 4;
p, q, r identically or differently are zero, 1, 2, 3 or 4;
t is 1, 2, 3 or 4;
R(42) and R(43) identically or differently are hydrogen or (C₁–C₆)-alkyl; or
R(42) and R(43) together with the carbon atom carrying them form a (C₃–C₈)-cycloalkyl;
R(44) is H, (C₁–C₆)-alkyl, (C₃–C₈)-cycloalkyl or —C_eH_{2e}—R(45);
e is zero, 1, 2, 3 or 4;
R(45) is phenyl,
which is unsubstituted or substituted by 1–3 substituents from the group consisting of F, Cl, CF₃, methyl, methoxy and NR(52)R(53) where
R(52) and R(53) are H or (C₁–C₄)-alkyl, or
R(45) is (C₁–C₉)-heteroaryl,
which is unsubstituted or substituted as phenyl; or
R(45) is (C₁–C₆)-alkyl,
which is unsubstituted or substituted by 1–3 OH;
R(46), R(47), R(48), R(49) and R(50) are hydrogen or methyl; or
R(2) is R(55)—NH—SO₂—;
R(55) is R(56)R(57)N—(C=Y)—;
Y is oxygen, S or N—R(58);
R(56) and R(57) identically or differently are H, (C₁–C₈)-alkyl, (C₃–C₆)-alkenyl or —C_fH_{2f}—R(59);
f is zero, 1, 2, 3 or 4;
R(59) is (C₅–C₇)-cycloalkyl or phenyl,
which is unsubstituted or substituted by 1–3 substituents selected from the group consisting of F, Cl, CF₃, methoxy and (C₁–C₄)-alkyl; or
R(56) and R(57) together are 4 or 5 methylene groups, of which one CH₂ group can be replaced by oxygen, S, NH, N—CH₃ or N-benzyl;
R(58) is defined as R(56) or is amidine;
R(3), R(4) and R(5) independently of one another are defined as R(1) or R(2);
and their pharmaceutically tolerable salts;
(HOE 93/F 220—EP-Offenlegungsschrfft 640 593, NZ 264 117)
q) benzoylguanidines of the formula I

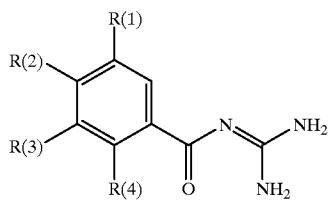

(I)

in which:
R(1) is hydrogen, F, Cl, Br, I, —NO2, —C≡N, —X_o—(CH₂)_p—(CF₂)_q—CF₃, R(5)—SO_m—, R(6)—CO—, R(6)R(7)N—CO— or R(6)R(7)N—SO₂—;
X is oxygen, —S— or NR(14);
m is zero, 1 or 2;
o is zero or 1;
p is zero, 1 or 2;
q is zero, 1, 2, 3, 4, 5 or 6;
R(5) and R(6) are (C₁–C₈)-alkyl, (C₃–C₆)-alkenyl, —C_nH_{2n}—R(8) or CF₃;

n is zero, 1, 2, 3 or 4;
R(8) is (C₃–C₇)-cycloalkyl, phenyl,
which is not substituted or is substituted by 1 to 3 substituents selected from the group consisting of F, Cl, CF₃, methyl, methoxy and NR(9)R(10);
R(9) and R(10) are H or (C₁–C₄)-alkyl; or
R(6) is hydrogen;
R(7) is hydrogen or (C₁–C₄)-alkyl; or
R(6) and R(7) together are 4 or 5 methylene groups, of which one CH₂ group can be replaced by oxygen, S, NH, N—CH₃ or N-benzyl;

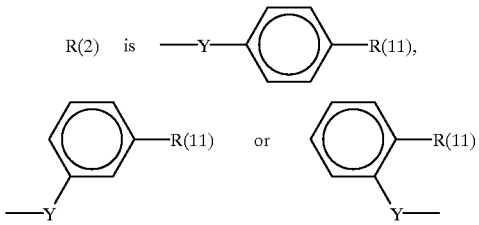

R(11) is (C₁–C₉)-heteroaryl,
which is linked via C or N and which is unsubstituted or substituted by 1 to 3 substituents selected from the group consisting of F, Cl, CF₃, CH₃, methoxy, hydroxyl, amino, methylamino, dimethylamino and benzyl;
Y is oxygen, —S— or NR(12);
R(12) is H or (C₁–C₄)-alkyl;
R(3) is defined as R(1); or
R(3) is (C₁–C₆)-alkyl or —X—R(13);
X is oxygen, —S— or NR(14);
R(14) is H or (C₁–C₃)-alkyl;
R(13) is H, (C₁–C₆)-alkyl, (C₃–C₈)-cycloalkyl or —C_bH_{2b}—R(15);
b is zero, 1, 2, 3 or 4; or
R(13) and R(14) together are 4 or 5 methylene groups, of which one CH₂ group can be replaced by oxygen, S, NH, N—CH₃ or N-benzyl;
R(15) is phenyl,
which is unsubstituted or substituted by 1–3 substituents selected from the group consisting of F, Cl, CF₃, methyl, methoxy and NR(9)R(10);
R(9) and R(10) are H or (C₁–C₄)-alkyl;
R(4) is hydrogen, —OR(16), —NR(16)R(17) or C_rF_{2r+1};
R(16) and R(17) independently are hydrogen or (C₁–C₃)-alkyl;
r is 1, 2, 3 or 4;
and their pharmaceutically tolerable salts;
(HOE 93/F 223 K—EP 639 573, NZ 264 130)
r) benzo-fused 5-membered ring heterocycles of the formula I

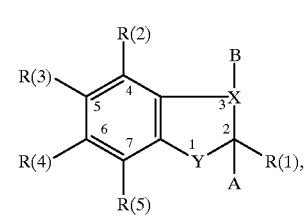

(I)

in which:
X is N or CR(6);

Y is oxygen, S or NR(7);

A, B together are a bond; or

A, B are both hydrogen, if X is simultaneously CR(6) and Y is NR(7);

one of the substituents R(1) to R(6) is a —CO—N=C(NH$_2$)$_2$ group;

the other substituents R(1) to R(6) in each case are hydrogen, F, Cl, Br, I or (C$_1$–C$_6$)-alkyl;

up to two of the other substituents R(1) to R(6) are CN, NO$_2$, N$_3$, (C$_1$–C$_4$)-alkyloxy or CF$_3$;

up to one of the other substituents is R(8)—C$_n$H$_{2n}$—Z—;
 n is zero to 10;
  where the alkylene chain —C$_n$H$_{2n}$— is straight-chain or branched and where one carbon atom can be replaced by an oxygen or sulfur atom or by a nitrogen atom;
 R(8) is hydrogen, (C$_2$–C$_6$)-alkenyl or (C$_3$–C$_{10}$)-cycloalkyl,
  which is unsubstituted or substituted by 1 to 4 methyl groups or an OH group, or can contain an ethylene group —CH=CH—, and in which one methylene group can be replaced by an oxygen or sulfur atom or by a nitrogen atom; or
 R(8) is phenyl,
  which is unsubstituted or substituted by 1 to 3 substituents selected from the group consisting of F, Cl, Br, I, CF$_3$, CH$_3$—S(O)$_s$— or R(9)—W$_y$—;
  s is zero, 1 or 2;
  R(9) is H, methyl, ethyl,
  W is oxygen or NR(10);
   R(10) is H or methyl;
  y is zero or 1; or
 R(8) is C$_m$F$_{2m+1}$;
  m is 1 to 3; or
 R(8) is 1- or 2-naphthyl, pyridyl, quinolyl or isoquinolyl;
 Z is —CO—, —CH$_2$— or —[CR(11)(OH)]$_q$—;
  q is 1, 2 or 3;
  R(11) is H or methyl; or
 Z is oxygen or —NR(12)—;
  R(12) is H or methyl; or
 Z is —S(O)$_s$—;
  s is zero, 1 or 2; or
 Z is —SO$_2$—NR(13)—;
  R(13) is H or (C$_1$–C$_4$)-alkyl;
R(7) is hydrogen, (C$_1$–C$_{10}$)-alkyl, (C$_2$–C$_{10}$)-alkenyl or R(8)—C$_n$H$_{2n}$—;

and their pharmaceutically tolerable salts;
(HOE 93/F 236—EP-Offenlegungsschrift 638 548, NZ 264 216)

s) benzoylguanidines of the formula I

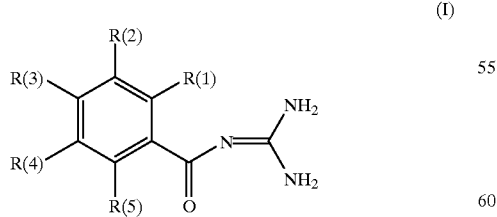

(I)

in which:

R(1), R(3) or R(4) is —NR(6) C=X NR(7)R(8);
 X is oxygen or S;
 R(6) is hydrogen, (C$_1$–C$_8$)-alkyl, (C$_1$–C$_8$)-perfluoroalkyl, (C$_3$–C$_8$)-alkenyl or —C$_n$H$_{2n}$—R(9);
 n is zero, 1, 2, 3 or 4;
 R(9) is (C$_3$–C$_8$)-cycloalkyl, phenyl, biphenylyl or naphthyl,
  where the aromatics are not substituted or are substituted by 1–3 substituents selected from the group consisting of F, Cl, CF$_3$, methyl, methoxy and NR(10)R(11);
   R(10) and R(11) are H, (C$_1$–C$_4$)-alkyl or (C$_1$–C$_4$)-perfluoroalkyl;
 R(7) is hydrogen, (C$_1$–C$_8$)-alkyl, (C$_1$–C$_8$)-perfluoroalkyl, (C$_3$–C$_8$)-alkenyl or —C$_o$H$_{2o}$—R(12);
 o is zero, 1, 2, 3 or 4;
 R(12) is (C$_3$–C$_8$)-cycloalkyl, phenyl, biphenylyl or naphthyl,
  where the aromatics are not substituted or are substituted by 1–3 substituents selected from the group consisting of F, Cl, CF$_3$, methyl, methoxy and NR(13)R(14);
   R(13) and R(14) are H, (C$_1$–C$_4$)-alkyl or (C$_1$–C$_4$)-perfluoroalkyl;
 R(8) is defined as R(7); or
 R(7) and R(8) together are 4 or 5 methylene groups, of which one CH$_2$ group can be replaced by oxygen, S, NH, N—CH$_3$ or N-benzyl;

the remaining substituents R(2), R(3), R(4), R(5) or R(1), R(2), R(4), R(5) or R(1), R(2), R(3), R(5) in each case independently of one another are hydrogen, F, Cl, Br, I, —O$_{ta}$(C$_1$–C$_8$)-alkyl, —O$_{tb}$(C$_3$–C$_8$)-alkenyl, —O$_{tc}$(CH$_2$)$_b$C$_d$F$_{2d+1}$, —O$_{td}$C$_p$H$_{2p}$R(18), or up to 2 groups CN, NO$_2$, NR(16)R(17),
 b is zero or 1;
 d is 1, 2, 3, 4, 5, 6 or 7;
 ta is zero or 1;
 tb is zero or 1;
 tc is zero or 1;
 td is zero or 1;
 p is zero, 1, 2, 3 or 4;
 R(18) is (C$_3$–C$_8$)-cycloalkyl, phenyl, biphenylyl or naphthyl,
  where the aromatics are not substituted or are substituted by 1–3 substituents selected from the group consisting of F, Cl, CF$_3$, methyl, methoxy and NR(19)R(20);
   R(19) and R(20) are hydrogen or (C$_1$–C$_4$)-alkyl or (C$_1$–C$_4$)-perfluoroalkyl;
 R(16) is hydrogen, (C$_1$–C$_8$)-alkyl, (C$_1$–C$_8$)-perfluoroalkyl, (C$_3$–C$_8$)-alkenyl, —C$_q$H$_{2q}$—R(21),
 q is zero, 1, 2, 3 or 4;
 R(21) is (C$_3$–C$_8$)-cycloalkyl, phenyl, biphenylyl or naphthyl,
  where the aromatics are not substituted or are substituted by 1–3 substituents from the group F, Cl, CF$_3$, methyl, methoxy or NR(22)R(23), R(22) and R(23) are hydrogen, (C$_1$–C$_4$)-alkyl or (C$_1$–C$_4$)-perfluoroalkyl;
 R(17) is hydrogen, (C$_1$–C$_8$)-alkyl, (C$_1$–C$_8$)-perfluoroalkyl, (C$_3$–C$_8$)-alkenyl, —C$_r$H$_{2r}$—R(24);
 r is zero, 1, 2, 3 or 4;
 R(24) is (C$_3$–C$_8$)-cycloalkyl, phenyl, biphenylyl or naphthyl,
  where the aromatics are not substituted or are substituted by 1–3 substituents selected from the group consisting of F, Cl, CF$_3$, methyl, methoxy and NR(25)R(26);
   R(25) and R(26) are hydrogen, (C$_1$–C$_4$)-alkyl or (C$_1$–C$_4$)-perfluoroalkyl; or R(16) and R(17) together are 4 or 5 methylene groups, of which one $CH_2$ group can be replaced by oxygen, S, NH, N—$CH_3$ or N-benzyl;

and their pharmaceutically tolerable salts;

(HOE 93/F 249—EP-Offenlegungsschrift 640 587, NZ 264 282)

t) diacyl-substituted guanidines of the formula I

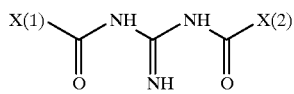

in which: X(1) and X(2) are

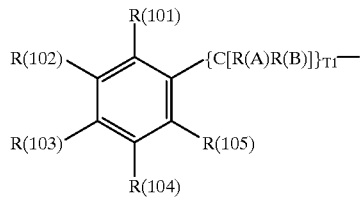

T1 is zero, 1, 2, 3 or 4;

R(A) and R(B) independently of one another are hydrogen, F, Cl, Br, I, CN, OR(106), $(C_1-C_8)$-alkyl, $(C_3-C_8)$-cycloalkyl, $O_{zk}(CH_2)_{zl}C_{zm}F_{2zm+1}$, NR(107)R(108), phenyl or benzyl, where the aromatics are not substituted or are substituted by 1–3 substituents selected from the group consisting of F, Cl, $CF_3$, methyl, methoxy and NR(109)R(110);

R(109) and R(110) are hydrogen, $(C_1-C_4)$-alkyl or $(C_1-C_4)$-perfluoroalkyl;

zl is zero, 1, 2, 3 or 4;

zk is zero or 1;

zm is 1, 2, 3, 4, 5, 6, 7 or 8;

R(106) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(111)R(112);

R(111) and R(112) are hydrogen, $(C_1-C_4)$-alkyl or $(C_1-C_4)$-perfluoroalkyl;

R(107) and R(108) independently of one another are defined as R(106), or

R(107) and R(108) together are 4 or 5 methylene groups, of which one $CH_2$ group can be replaced by oxygen, S, NH, N—$CH_3$ or N-benzyl; or X(1) and X(2) are

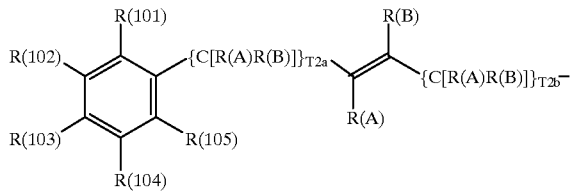

T2a and T2b independently of one another are zero, 1 or 2;

where the double bond can have the (E)- or (Z)-configuration; or

X(1) and X(2) are

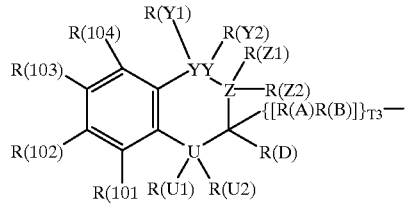

T3 is zero, 1 or 2;

U, YY and Z independently of one another are C or N, where U, YY, Z can carry the following number of substituents:

| U, YY or Z | Bonded in the ring to a double bond | Number of permitted substituents |
|---|---|---|
| C | yes | 1 |
| C | no | 2 |
| N | yes | 0 |
| N | no | 1 |

R(D) is hydrogen, $(C_1-C_8)$-alkyl or $(C_1-C_8)$-perfluoroalkyl, R(U1), R(U2), R(Y1), R(Y2), R(Z1), R(Z2) independently of one another are hydrogen, F, Cl, Br, I, CN, OR(114), $(C_1-C_8)$-alkyl, $(C_3-C_8)$-cycloalkyl, $O_{zka}(CH_2)_{zla}C_{zma}F_{2zma+1}$, NR(115)R(116), phenyl or benzyl, where the aromatics are not substituted or are substituted by 1–3 substituents selected from the group consisting of F, Cl, $CF_3$, methyl, methoxy, NR(117)R(118), R(117) and R(118) are hydrogen, $(C_1-C_4)$-alkyl or $(C_1-C_4)$-perfluoroalkyl, zka is zero or 1;

zla is zero, 1, 2, 3 or 4;

zma is 1, 2, 3, 4, 5, 6, 7 or 8;

R(114) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(119)R(120);

R(119) and R(120) are hydrogen, $(C_1-C_4)$-alkyl or $(C_1-C_4)$-perfluoroalkyl;

R(115) and R(116) independently of one another are defined as R(114); or

R(115) and R(116) together are 4 or 5 methylene groups, of which one $CH_2$ group can be replaced by oxygen, S, NH, N—$CH_3$ or N-benzyl;

but where the constitution of U is nitrogen (N), YY is nitrogen (N) and Z is carbon (C) is excluded, R(101), R(102), R(103), R(104) and R(105) independently of one another are hydrogen, F, Cl, Br, I, —C≡N, $X_{zoa}$—$(CH_2)_{zpa}$—$(C_{zqa}F_{2zqa+1})$, R(110a)—$SO_{zbm}$, R(110b)R(110c)N—CO, R(111a)—CO— or R(112a)R(113a)N—$SO_2$—, where the perfluoroalkyl group is straight-chain or branched, X is oxygen, S or NR(114a);

R(114a) is H or $(C_1-C_3)$-alkyl;

zoa is zero or 1;

zbm is zero, 1 or 2;
zpa is zero, 1, 2, 3 or 4;
zqa is 1, 2, 3, 4, 5, 6, 7 or 8;
R(110a), R(110b), R(111a) and R(112a) independently of one another are $(C_1-C_8)$-alkyl, $(C_3-C_8)$-alkenyl, $-C_{zn}H_{2zn}-R(115a)$ or $(C_1-C_8)$-perfluoroalkyl;
zn is zero, 1, 2, 3 or 4;
 R(115a) is $(C_3-C_8)$-cycloalkyl, phenyl, biphenylyl or naphthyl,
  where the aromatics are not substituted or are substituted by 1–3 substituents selected from the group consisting of F, Cl, $CF_3$, methyl, methoxy and NR(116a)R(117a);
   R(116a) and R(117a) are hydrogen, $(C_1-C_4)$-perfluoroalkyl or $(C_1-C_4)$-alkyl; or
R(101b), R(111a) and R(112a) are hydrogen;
R(110c) and R(113a) independently are hydrogen, $(C_1-C_4)$-perfluoroalkyl or $(C_1-C_4)$-alkyl; or
R(110b) and R(110c) and R(112a) and R(113a) together are 4 or 5 methylene groups, of which one $CH_2$ group can be replaced by oxygen, sulfur, NH, N—$CH_3$ or N-benzyl; or
R(101), R(102), R(103), R(104), R(105) independently of one another are $(C_1-C_8)$-alkyl, $-C_{zal}H_{2zal}R(118a)$ or $(C_3-C_8)$-alkenyl,
zal is zero, 1, 2, 3 or 4;
 R(118a) is $(C_3-C_8)$-cycloalkyl, phenyl, biphenylyl or naphthyl,
  where the aromatics are not substituted or are substituted by 1–3 substituents from the group consisting of F, Cl, $CF_3$, methyl, methoxy or NR(119a)R(119b);
   R(119a) and R(119b) are hydrogen, $(C_1-C_4)$-alkyl or $(C_1-C_4)$-perfluoroalkyl; or
R(101), R(102), R(103), R(104), R(105) independently of one another are $(C_1-C_9)$-heteroaryl,
which is linked via C or N and which is unsubstituted or substituted by 1–3 substituents from the group consisting of F, Cl, $CF_3$, $CH_3$, methoxy, hydroxyl, amino, methylamino and dimethylamino; or
R(101), R(102), R(103), R(104), R(105) independently of one another are $-C{\equiv}C-R(193)$;
 R(193) is phenyl which is not substituted or is substituted by 1–3 substituents from the group consisting of F, Cl, $CF_3$, methyl, methoxy or NR(194)R(195);
 R(194) and R(195) are hydrogen or $CH_3$; or
R(101), R(102), R(103), R(104), R(105) independently of one another are
 —Y-para-$C_6H_4$—$(CO)_{zh}$—$(CHOH)_{zi}$—$(CH_2)_{zj}$—$(CHOH)_{zk}$—R(123), —Y-meta-$C_6H_4$—$(CO)_{zad}$—$(CHOH)_{zae}$—$(CH_2)_{zaf}$—$(CHOH)_{zag}$—R(124) or —Y-ortho-$C_6H_4$—$(CO)_{zah}$—$(CHOH)_{zao}$—$(CH_2)_{zap}$—$(CHOH)_{zak}$—R(125);
 Y is oxygen, —S— or —NR(122d)—;
 zh, zad, zah independently are zero or 1;
 zi, zj, zk, zae, zaf, zag, zao, zap and zak independently are zero, 1, 2, 3 or 4;
 but where in each case
  zh, zi and zk are not simultaneously zero,
  zad, zae and zag are not simultaneously zero, and
  zah, zao and zak are not simultaneously zero,
 R(123), R(124) R(125) and R(122d) independently are hydrogen or $(C_1-C_3)$-alkyl; or
R(101), R(102), R(103), R(104) and R(105) independently of one another are SR(129), —OR(130), —NR(131)R(132) or —CR(133)R(134)R(135);

R(129), R(130), R(131) and R(133) independently are —$C_{zab}H_{2zab}$—$(C_1-C_8)$-heteroaryl,
which is unsubstituted or substituted by 1–3 substituents from the group consisting of F, Cl, $CF_3$, $CH_3$, methoxy, hydroxyl, amino, methylamino and dimethylamino;
zab is zero, 1 or 2;
R(132), R(134) and R(135) independently are defined as R(129) or are hydrogen, $(C_1-C_4)$-alkyl or $(C_1-C_4)$-perfluoroalkyl; or
R(101), R(102), R(103), R(104) and R(105) independently of one another are —W-para-$(C_6H_4)$—R(196), —W-meta-$(C_6H_4)$-R(197) or —W-ortho-$(C_6H_4)$—R(198);
 R(196), R(197) and R(198) independently of one another are $(C_1-C_8)$-heteroaryl,
 which is linked via C or N and which is unsubstituted or substituted by 1 to 3 substituents from the group consisting of F, Cl, $CF_3$, $CH_3$, methoxy, hydroxyl, amino, methylamino, dimethylamino and benzyl;
 W is oxygen, S or NR(136)—;
  R(136) is hydrogen or $(C_1-C_4)$-alkyl; or
R(101), R(102), R(103), R(104) and R(105) independently of one another are R(146)X(1a)—;
 X(1a) is oxygen, S, NR(147), (D=O)A—, NR(148)C=MN$^{(*)}$R(149)—;
 M is oxygen or sulfur;
 A is oxygen or NR(150);
 D is C or SO;
 R(146) is $(C_1-C_8)$-alkyl, $(C_3-C_8)$-alkenyl, $(CH_2)_{zbz}C_{zdz}F_{2zdz+1}$ or —$C_{zxa}H_{2zxa}$—R(151);
 zbz is zero or 1;
 zdz is 1, 2, 3, 4, 5, 6 or 7;
 zxa is zero, 1, 2, 3 or 4;
  R(151) is $(C_3-C_8)$-cycloalkyl, phenyl, biphenylyl or naphthyl,
   where the aromatics are not substituted or are substituted by 1–3 substituents from the group consisting of F, Cl, $CF_3$, methyl, methoxy and NR(152)R(153);
    R(152) and R(153) are hydrogen, $(C_1-C_4)$-alkyl or $(C_1-C_4)$-perfluoroalkyl;
 R(147), R(148) and R(150) independently are hydrogen, $(C_1-C_4)$-alkyl, $(C_1-C_4)$-perfluoroalkyl;
 R(149) is defined as R(146), or
 R(146) and R(147), or R(146) and R(148) together are 4 or 5 methylene groups, of which one $CH_2$ group can be replaced by oxygen, sulfur, NH, N—$CH_3$ or N-benzyl;
 where A and N$^{(*)}$ are bonded to the phenyl nucleus of the alkanoyl parent structure; or
R(101), R(102), R(103), R(104) and R(105) independently of one another are —SR(164), —OR(165), —NHR(166), —NR(167)R(168), —CHR(169)R(170), —CR(154)R(155)OH, —C${\equiv}$CR(156), —CR(158)=CR(157) or —[CR(159)R(160)]$_{zu}$—(C=O)—[CR(161)R(162)]$_{zv}$—R(163);
 R(164), R(165), R(166), R(167), R(169) identically or differently are —$(CH_2)_{zy}$—$(CHOH)_{zz}$—$(CH_2)_{zaa}$—$(CHOH)_{zt}$—R(171) or —$(CH_2)_{zab}$—O—$(CH_2$—$CH_2O)_{zac}$—R(172);
 R(171) and R(172) are hydrogen or methyl;
 zu is 1, 2, 3 or 4;
 zv is zero, 1, 2, 3 or 4;
 zy, zz, zaa, zab, zac identically or differently are zero, 1, 2, 3 or 4;
 zt is 1,2, 3 or 4;

R(168), R(170), R(154), R(155) identically or differently are hydrogen or (C$_1$–C$_6$)-alkyl, or R(169) and R(170), or R(154) and R(155) together with the carbon atom carrying them are a (C$_3$–C$_8$)-cycloalkyl;

R(163) is hydrogen, (C$_1$–C$_6$)-alkyl, (C$_3$–C$_8$)-cycloalkyl or —C$_{zeb}$H$_{2zeb}$—R(173);

zeb is zero, 1, 2, 3 or 4;

R(156), R(157) and R(173) independently are phenyl which is unsubstituted or is substituted by 1–3 substituents from the group consisting of F, Cl, CF$_3$, methyl, methoxy and NR(174)R(175);

R(174) and R(175) are hydrogen or (C$_1$–C$_4$)-alkyl; or

R(156), R(157) and R(173) independently are (C$_1$–C$_8$)-heteroaryl, which is unsubstituted or substituted as phenyl;

R(158), R(159), R(160), R(161) and R(162) are hydrogen or methyl, or

R(101), R(102), R(103), R(104), R(105) independently of one another are R(176)—NH—SO$_2$—;

R(176) is R(177)R(178)N—(C=Y')—;

Y' is oxygen, S or N—R(179);

R(177) and R(178) identically or differently are hydrogen, (C$_1$–C$_8$)-alkyl, (C$_3$–C$_6$)-alkenyl or —C$_{zfa}$H$_{2zfa}$—R(180);

zfa is zero, 1, 2, 3 or 4;

R(180) is (C$_5$–C$_7$)-cycloalkyl or phenyl, which is unsubstituted or substituted by 1–3 substituents selected from the group consisting of F, Cl, CF$_3$, methoxy or (C$_1$–C$_4$)-alkyl; or R(177) and R(178) together are 4 or 5 methylene groups, of which one CH$_2$ group can be replaced by oxygen, sulfur, NH, N—CH$_3$ or N-benzyl;

R(179) is defined as R(177) or is amidine, or

R(101), R(102), R(103), R(104), R(105) independently of one another are NR(184a)R(185), OR(184b), SR(184c) or —C$_{znx}$H$_{2znx}$—R(184d);

znx is zero, 1, 2, 3 or 4;

R(184d) is (C$_3$–C$_7$)-cycloalkyl or phenyl, which is not substituted or substituted by 1–3 substituents from the group consisting of F, Cl, CF$_3$, methyl, methoxy and NR(116k)R(117k);

R(116k) and R(117k) are hydrogen or C$_1$–C$_4$-alkyl;

R(184a), R(184b), R(184c), R(185) independently of one another are hydrogen, (C$_1$–C$_8$)-alkyl, (C$_1$–C$_8$)-perfluoroalkyl or (CH$_2$)$_{zao}$—R(184g);

zao is zero, 1, 2, 3 or 4;

R(184g) is (C$_3$–C$_7$)-cycloalkyl or phenyl, which is not substituted or substituted by 1–3 substituents from the group consisting of F, Cl, CF$_3$, methyl, methoxy and NR(184u)R(184v);

R(184u) and R(184v) are hydrogen or C$_1$–C$_4$-alkyl; or

R(184a) and R(185) together are 4 or 5 methylene groups, of which one CH$_2$ group can be replaced by oxygen, sulfur, NH, N—CH$_3$ or N-benzyl;

and their pharmaceutically tolerable salts;

(HOE 93/F 254—EP-Offenlegungsschrift 640 588, NZ 264 307)

u) benzoylguanidines of the formula I

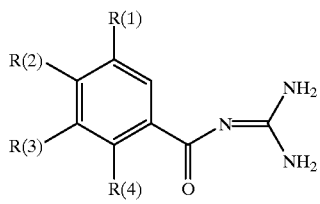

in which:

R(1) is H, F, Cl, Br, I, CN, NO$_2$, (C$_1$–C$_8$)-alkyl, (C$_3$–C—$_8$)-cycloalkyl or X$_a$—(CH$_2$)$_b$—(CF$_2$)$_c$—CF$_3$;

X is oxygen, S or NR(5);

a is zero or 1;

b is zero, 1 or 2;

c is zero, 1, 2 or 3;

R(5) is H, (C$_1$–C$_4$)-alkyl or —C$_d$H$_{2d}$R(6);

d is zero, 1, 2, 3 or 4;

R(6) is (C$_3$–C$_8$)-cycloalkyl, phenyl, biphenylyl or naphthyl, where the aromatics are not substituted or are substituted by 1 to 3 substituents selected from the group consisting of F, Cl, CF$_3$, methyl, methoxy and NR(7)R(8);

R(7) and R(8) independently are H or (C$_1$–C$_4$)-alkyl; or

R(1) is —SR(10), —OR(10) or —CR(10)R(11)R(12);

R(10) is —C$_f$H$_{2f}$—(C$_3$–C$_8$)-cycloalkyl, —(C$_1$–C$_8$)-heteroaryl or phenyl, where the aromatic systems are unsubstituted or substituted by one to 3 substituents selected from the group consisting of F, Cl, CF$_3$, CH$_3$, methoxy, hydroxyl, amino, methylamino and dimethylamino;

f is zero, 1 or 2;

R(11) and R(12) independently of one another are defined as R(10) or are hydrogen or (C$_1$–C$_4$)-alkyl; or R(1) is phenyl, naphthyl, biphenylyl or (C$_1$–C$_9$)-heteroaryl, the latter linked via C or N, and which are unsubstituted or substituted by 1 to 3 substituents selected from the group consisting of F, Cl, CF$_3$, CH$_3$, methoxy, hydroxyl, amino, methylamino and dimethylamino; or R(1) is —SR(13), —OR(13), —NHR(13), —NR(13)R(14), —CHR(13)R(15), —C[R(15)R(16)]OH, C≡CR(18), —C[R(19)]=CR(18), —[CR(20)R(21)]$_k$—(CO)—[CR(22)R(23)R(24)];

R(13) and R(14) identically or differently are —(CH$_2$)$_g$—(CHOH)$_h$—(CH$_2$)$_i$—(CHOH)$_j$—R(17), R(17) is hydrogen or methyl;

—(CH$_2$)$_g$—O—(CH$_2$—CH$_2$O)$_h$—R(24), g, h, i identically or differently are zero, 1, 2, 3 or 4;

j is 1, 2, 3 or 4;

R(15) and R(16) identically or differently are hydrogen, (C$_1$–C$_6$)-alkyl or together with the carbon atom carrying them are a (C$_3$–C$_8$)-cycloalkyl;

R(18) is phenyl, which is unsubstituted or substituted by 1 to 3 substituents selected from the group consisting of F, Cl, CF$_3$, methyl, methoxy and NR(25)R(26);

R(25) and R(26) are H or (C$_1$–C$_4$)-alkyl; or

R(18) is (C$_1$–C$_9$)-heteroaryl, which is unsubstituted or substituted as phenyl; or R(18) is (C$_1$–C$_6$)-alkyl, which is unsubstituted or substituted by 1 to 3 OH; or R(18) is $(C_3-C_8)$-cycloalkyl;

R(19), R(20), R(21), R(22) and R(23) are hydrogen or methyl;

k is zero, 1, 2, 3 or 4;

l is zero, 1, 2, 3 or 4;

R(24) is H, $(C_1-C_6)$-alkyl, $(C_3-C_8)$-cycloalkyl or $-C_mH_{2m}-R(18)$;

m is 1, 2, 3 or 4;

R(2) and R(3) independently of one another are defined as R(1);

R(4) is $(C_1-C_3)$-alkyl, F, Cl, Br, I, CN or $-(CH_2)_n-(CF_2)_o-CF_3$;

n is zero or 1;

o is zero, 1 or 2;

and their pharmaceutically tolerable salts;

(HOE 93/F 436—EP-Offenlegungsschrift 659 748), NZ 270 264)

v) acylguanidines of the formula I (I)

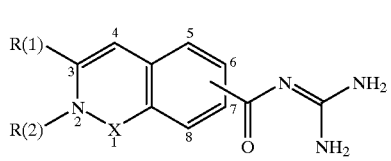

in which:

X is carbonyl, sulfonyl,

R(1) is H, $(C_1-C_8)$-alkyl, unsubstituted or substituted by hydroxyl, $(C_3-C_8)$-cycloalkyl, phenyl,
which is unsubstituted or substituted by 1–3 substituents from the group F, Cl, CF3, $CH_3$, methoxy, hydroxyl, amino, methylamino or dimethylamino, R(2) is H, $(C_1-C_4)$-alkyl, and their pharmaceutically tolerable salts;

(HOE 94/F 014 K—EP-Offenlegungsschrift 666 252, NZ 270 370)

w) phenyl-substituted alkycarboxylic acid guanidides, carrying perfluoroalkyl groups, of the formula I (I)

in which:

R(A) is hydrogen, F, Cl, Br, I, CN, OR(6), $(C_1-C_8)$-alkyl, $(C_3-C_8)$-cycloalkyl, $O_r(CH_2)_aC_bF_{2b+1}$ or NR(7)R(8);

r is zero or 1;

a is zero, 1, 2, 3 or 4;

b is 1, 2, 3, 4, 5, 6, 7 or 8;

R(6) is hydrogen, $(C_1-C_8)$-alkyl, $(C_3-C_8)$-alkenyl, $(C_3-C_8)$-cycloalkyl, phenyl or benzyl,
where the aromatics are not substituted or are substituted by 1–3 substituents selected from the group consisting of F, Cl, CF3, methyl, methoxy and NR(9)R(10);

R(9) and R(10) are H, $(C_1-C_4)$-alkyl or $(C_1-C_4)$-perfluoroalkyl;

R(7) and R(8) independently of one another are defined as R(6);

R(B) independently is defined as R(A);

X is 1, 2 or 3;

R(1) is hydrogen, $(C_1-C_8)$-alkyl, $(C_3-C_9)$-cycloalkyl, $-O_t(CH_2)_dC_eF_{2e+1}$, F, Cl, Br, I or CN;

t is zero or 1;

d is zero, 1, 2, 3 or 4;

e is 1, 2, 3, 4, 5, 6, 7 or 8;

R(2), R(3), R(4) and R(5) independently of one another are defined as R(1);

but with the condition that at least one of the substituents R(1), R(2), R(3), R(4), R(5), R(A) and R(B) is an $-O_t(CH_2)_dC_eF_{2e+1}$ or an $O_r(CH_2)_aC_bF_{2b+1}$ group, and their pharmaceutically tolerable salts;

(HOE 94/F 094—EP-Offenlegungsschrift 676 395, NZ 270 894)

x) heteroaroylguanidines of the formula I

I in which:

HA is $SO_m$, O or NR(5);

m is zero, 1 or 2;

R(5) is hydrogen, $(C_1-C_8)$-alkyl or $-C_{am}H_{2am}R(81)$;

am is zero, 1 or 2;

R(81) is $(C_3-C_8)$-cycloalkyl or phenyl,
which is not substituted or is substituted by 1–3 substituents selected from the group consisting of F, Cl, $CF_3$, methyl, methoxy and NR(82)R(83);

R(82) and R(83) is H or $CH_3$; or

R(81) is $(C_1-C_9)$-heteroaryl,
which is linked via C or N and which is unsubstituted or substituted by 1–3 substituents selected from the group consisting of F, Cl, $CF_3$, $CH_3$, methoxy, hydroxyl, amino, methylamino and dimethylamino;

one of the two substituents R(1) and R(2) is $-CO-N=C(NH_2)_2$;

and the other in each case is hydrogen, F, Cl, Br, I, $(C_1-C_3)$-alkyl, $-OR(6)$, $C_rF_{2r+1}$, $-CO-N=C(NH_2)_2$ or $-NR(6)R(7)$;

R(6) and R(7) independently are hydrogen or $(C_1-C_3)$-alkyl;

r is 1, 2, 3 or 4;

R(3) and R(4) independently of one another are hydrogen, F, Cl, Br, I, $-C\equiv N$, $X-(CH_2)_p-(C_{q-F2q+1})$, R(8)—$SO_{bm}$, R(9)R(10)N—CO, R(11)—CO— or R(12)R(13)N—$SO_2$—, where the perfluoroalkyl group is straight-chain or branched, X is oxygen, S or NR(14);

R(14) is H or $(C_1-C_3)$-alkyl;

bm is zero, 1 or 2;

p is zero, 1 or 2;

q is zero, 1, 2, 3, 4, 5 or 6;

R(8), R(9), R(11) and R(12) independently are $(C_1-C_8)$-alkyl, $(C_3-C_6)$-alkenyl, $-C_nH_{2n}-R(15)$, $CF_3$;

n is zero, 1, 2, 3 or 4;

R(15) is ($C_3$–$C_7$)-cycloalkyl or phenyl;
which is not substituted or is substituted by 1–3 substituents selected from the group consisting of F, Cl, $CF_3$, methyl, methoxy or NR(16)R(17);
R(16) and R(17) are H or $C_1$–$C_4$-alkyl; or
R(9), R(11) and R(12) are H;
R(10) and R(13) independently are H or ($C_1$–$C_4$)-alkyl; or
R(9) and R(10), and R(12) and R(13) together are 4 or 5 methylene groups, of which one $CH_2$ group can be replaced by oxygen, S, NH, N—$CH_3$ or N-benzyl, or
R(3) and R(4) independently of one another are ($C_1$–$C_8$)-alkyl or —$C_{a1}H_{2a1}$R(18);
a1 is zero, 1 or 2;
R(18) is ($C_3$–$C_8$)-cycloalkyl or phenyl;
which is not substituted or is substituted by 1–3 substituents selected from the group consisting of F, Cl, $CF_3$, methyl, methoxy and NR(19)R(20);
R(19) and R(20) are H or $CH_3$; or
R(3) and R(4) independently of one another are ($C_1$–$C_9$)-heteroaryl,
which is linked via C or N and which is unsubstituted or substituted by 1–3 substituents selected from the group consisting of F, Cl, $CF_3$, $CH_3$, methoxy, hydroxyl, amino, methylamino and dimethylamino; or
R(3) and R(4) independently of one another are

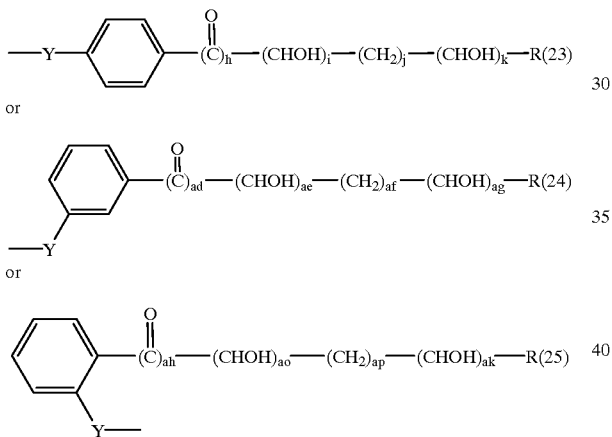

Y is oxygen, —S— or —NR(22)—;
h, ad, ah independently are zero or 1;
i, j, k, ae, af, ag, ao, ap and ak independently are zero, 1, 2, 3, 4,
but where in each case
h, i and k are not simultaneously zero,
ad, ae and ag are not simultaneously zero,
ah, ao and ak are not simultaneously zero,
R(23), R(24) R(25) and R(22) independently are hydrogen or ($C_1$–$C_3$)-alkyl; or
R(3) and R(4) independently are hydrogen, F, Cl, Br, I, CN, ($C_1$–$C_8$)-alkyl, ($C_1$–$C_8$)-perfluoroalkyl, ($C_3$–$C_8$)-alkenyl or —$C_gH_{2g}$R(26);
g is zero, 1, 2, 3 or 4;
R(26) is ($C_3$–$C_8$)-cycloalkyl, phenyl, biphenylyl or naphthyl,
where the aromatics are not substituted or are substituted by 1–3 substituents selected from the group consisting of F, Cl, $CF_3$, methyl, methoxy and NR(27)R(28);
R(27) and R(28) are H, ($C_1$–$C_4$)-alkyl or ($C_1$–$C_4$)-perfluoroalkyl; or R(3) and R(4) independently of one another are SR(29), —OR(30), —NR(31)R(32) or —CR(33)R(34)R(35);
R(29), R(30), R(31) and R(33) independently of one another are —$C_aH_{2a}$—($C_1$–$C_9$)-heteroaryl,
which is unsubstituted or substituted by 1–3 substituents selected from the group consisting of F, Cl, CF3, $CH_3$, methoxy, hydroxyl, amino, methylamino and dimethylamino;
a is zero, 1 or 2;
R(32), R(34) and R(35) independently of one another are defined as R(29) or are hydrogen, ($C_1$–$C_4$)-alkyl or ($C_1$–$C_4$-perfluoroalkyl; or
R(3) and R(4) independently of one another are

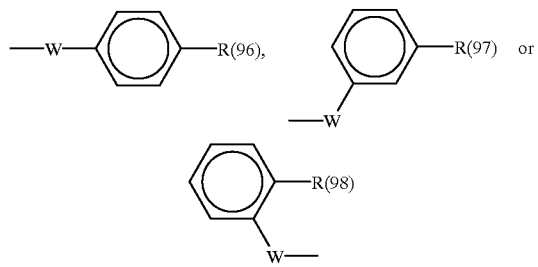

R(96), R(97) and R(98) independently are ($C_1$–$C_9$)-heteroaryl,
which is linked via C or N and which is unsubstituted or substituted by 1 to 3 substituents selected from the group consisting of F, Cl, $CF_3$, $CH_3$, methoxy, hydroxyl, amino, methylamino, dimethylamino or benzyl;
W is oxygen, S or NR(36)—;
R(36) is H or ($C_1$–$C_4$)-alkyl; or
R(3) and R(4) independently of one another are R(37)—$SO_{cm}$ or R(38)R(39)N—$SO_2$—;
cm is 1 or 2;
R(37) is ($C_1$–$C_8$)-alkyl, ($C_1$–$C_8$)-perfluoroalkyl, ($C_3$–$C_8$)-alkenyl or —$C_s$;$H_{2s}$R(40);
s is zero, 1, 2, 3 or 4;
R(40) is ($C_3$–$C_8$)-cycloalkyl, phenyl, biphenylyl or naphthyl,
where the aromatics are not substituted or are substituted by 1–3 substituents selected from the group consisting of F, Cl, $CF_3$, methyl, methoxy and NR(41)R(42);
R(41) and R(42) are H, ($C_1$–$C_4$)-alkyl or ($C_1$–$C_4$)-perfluoroalkyl;
R(38) is H, ($C_1$–$C_8$)-alkyl, ($C_1$–$C_8$)-perfluoroalkyl, ($C_3$–$C_8$)-alkenyl or —$C_wH_{2w}$—R(43);
w is zero, 1, 2, 3 or 4;
R(43) is ($C_3$–$C_8$)-cycloalkyl, phenyl, biphenylyl or naphthyl,
where the aromatics are not substituted or are substituted by 1–3 substituents selected from the group consisting of F, Cl, $CF_3$, methyl, methoxy and NR(44)R(45);
R(44) and R(45) are H, ($C_1$–$C_4$)-alkyl or ($C_1$–$C_4$)-perfluoroalkyl;
R(39) is H, ($C_1$–$C_4$)-alkyl or ($C_1$–$C_4$)-perfluoroalkyl; or
R(38) and R(39) together are 4 or 5 methylene groups, of which one $CH_2$ group can be replaced by oxygen, S, NH, N—$CH_3$ or N-benzyl; or
R(3) and R(4) independently of one another are R(46)X(1)—;
X(1) is oxygen, S, NR(47), (D=O)A—, NR(48)C=MN$^{(+)}$R(49)—, M is oxygen or S;
A is oxygen or NR(50);
D is C or SO;
R(46) is $(C_1-C_8)$-alkyl, $(C_3-C_8)$-alkenyl, $(CH_2)_b C_d F_{2d+1}$ or $—C_x H_{2x}—R(51)$;
b is zero or 1;
d is 1, 2, 3, 4, 5, 6 or 7;
x is zero, 1, 2, 3 or 4;
R(51) is $(C_3-C_8)$-cycloalkyl, phenyl, biphenylyl or naphthyl,
where the aromatics are not substituted or are substituted by 1–3 substituents selected from the group consisting of F, Cl, $CF_3$, methyl, methoxy and NR(52)R(53);
R(52) and R(53) are H, $(C_1-C_4)$-alkyl or $(C_1-C_4)$-perfluoroalkyl;
R(47), R(48) and R(50) independently are hydrogen, $(C_1-C_4)$-alkyl or $(C_1-C_4)$-perfluoroalkyl;
R(49) is defined as R(46); or
R(46) and R(47), or R(46) and R(48) together are 4 or 5 methylene groups, of which one $CH_2$ group can be replaced by oxygen, S, NH, N—$CH_3$ or N-benzyl,
where A and $N^{(*)}$ are bonded to the phenyl nucleus of the benzoylguanidine parent structure; or
R(3) and R(4) independently of one another are —SR(64), —OR(65), —NHR(66), —NR(67)R(68), —CHR(69)R(70), —C(OH)R(54)R(55), —C≡CR(56), —CR(58)=CHR(57), —[CR(59)R(60)]_u—(CO)—[CR(61)R(62)]_v—R(63);
R(64), R(65), R(66), R(67) and R(69) identically or differently are $—(CH_2)_y—(CHOH)_z—(CH_2)_{aa}—(CH_2OH)_t—R(71)$ or $—(CH_2)_{ab}—O—(CH_2—CH_2O)_{ac}—R(72)$,
R(71) and R(72) are hydrogen or methyl;
u is 1, 2, 3 or 4;
v is zero, 1, 2, 3 or 4;
y, z, aa identically or differently are zero, 1, 2, 3 or 4;
t is 1, 2, 3 or 4;
R(68), R(70), R(54) and R(55) identically or differently are hydrogen, $(C_1-C_6)$-alkyl; or
R(69) and R(70), or R(54) and R(55) together with the carbon atom carrying them are a $(C_3-C_8)$-cycloalkyl;
R(63) is H, $(C_1-C_6)$-alkyl, $(C_3-C_8)$-cycloalkyl or —$C_e H_{2e}$—R(73);
e is zero, 1, 2, 3 or 4;
R(56), R(57) and R(73) independently are phenyl, which are unsubstituted or substituted by 1–3 substituents selected from the group consisting of F, Cl, $CF_3$, methyl, methoxy and NR(74)R(75);
R(74) and R(75) are H or $(C_1-C_4)$-alkyl; or
R(56), R(57) and R(73) independently are $(C_1-C_9)$-heteroaryl,
which is unsubstituted or substitued as phenyl;
R(58), R(59), R(60), R(61) and R(62) are hydrogen or methyl, or
R(3) and R(4) independently of one another are R(76)—NH—$SO_2$—,
R(76) is R(77)R(78)N—(C=Y')—;
Y' is oxygen, S or N—R(79);
R(77) and R(78) identically or differently are H, $(C_1-C_8)$-alkyl, $(C_3-C_6)$-alkenyl, —$C_f H_{2f}$—R(80);
f is zero, 1, 2, 3 or 4;
R(80) is $(C_5-C_7)$-cycloalkyl or phenyl,
which is unsubstituted or substituted by 1–3 substituents selected from the group consisting of F, Cl, $CF_3$, methoxy and $(C_1-C_4)$-alkyl; or R(77) and R(78) together are 4 or 5 methylene groups, of which one $CH_2$ group can be replaced by oxygen, S, NH, N—$CH_3$ or N-benzyl,
R(79) is defined as R(77) or is amidine; or
R(3) and R(4) independently of one another are NR(84)R(85);
R(84) and R(85) independently of one another are H, $(C_1-C_4)$-alkyl, or together are 4 or 5 methylene groups,
of which one $CH_2$ group can be replaced by oxygen, S, NH, N—$CH_3$ or N-benzyl; or of which one or two $CH_2$ groups can be replaced by CH—$C_{dm}H_{2dm+1}$,
and their pharmaceutically tolerable salts;

(HOE 94/F 123—EP-Offenlegungsschrift 682 017, NZ 272 058)

y) bicyclic heteroaroylguanidines of the formula I

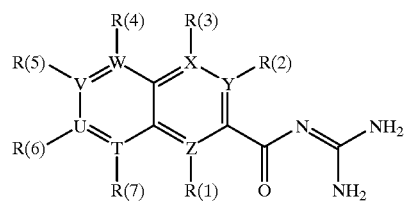

in which:

T, U, V, W, X, Y and Z independently of one another are nitrogen or carbon;
but with the restriction that X and Z are not simultaneously nitrogen,
and that T, U, V, W, X, Y and Z carry no substituents if they are nitrogen,
and that no more than four of them are simultaneously nitrogen,
R(1) and R(2) independently of one another are hydrogen, F, Cl, Br, I, $(C_1-C_3)$-alkyl, $(C_1-C_3)$-perfluoroalkyl, OR(8), NR(8)R(9) or C(=O)N=C(NH_2)_2;
R(8) and R(9) independently of one another are hydrogen or $(C_1-C_3)$-alkyl, or
R(8) and R(9) together are 4 or 5 methylene groups, of which one $CH_2$ group can be replaced by oxygen, S, NH, N—$CH_3$ or N-benzyl;
R(3), R(4), R(5), R(6) and R(7) independently of one another are hydrogen, F, Cl, Br, I, —C≡N, $X_k$—$(CH_2)_p$—$(C_q F_{2q+1})$, R(10a)—$SO_{bm}$, R(10b)R(10c)N—CO, R(11)—CO— or R(12)R(13)N—$SO_2$—,
where the perfluoroalkyl group is straight-chain or branched;
X is oxygen, S or NR(14);
R(14) is H or $(C_1-C_3)$-alkyl;
bm is zero, 1 or 2;
p is zero, 1 or 2;
k is zero or 1;
q 1, 2, 3, 4, 5 or 6;
R(10a), R(10b), R(11) and R(12) independently of one another are $(C_1-C_8)$-alkyl, $(C_3-C_6)$-alkenyl, —$C_n H_{2n}$—R(15) or $(C_1-C_8)$-perfluoroalkyl;
n is zero, 1, 2, 3 or 4;

R(15) is $(C_3-C_7)$-cycloalkyl or phenyl, which is not substituted or is substituted by 1–3 substituents selected from the group consisting of F, Cl, $CF_3$, methyl, methoxy and NR(16)R(17);

R(16) and R(17) are H or $C_1-C_4$-alkyl; or

R(10b), R(11) and R(12) are hydrogen;

R(10c) and R(13) independently are hydrogen or $(C_1-C_4)$-alkyl; or

R(10b) and R(10c) and R(12) and R(13) together are 4 or 5 methylene groups, of which one $CH_2$ group can be replaced by oxygen, sulfur, NH, N—$CH_3$ or N-benzyl; or R(3), R(4), R(5), R(6) and R(7) independently of one another are $(C_1-C_8)$-alkyl, —$C_{al}H_{2al}$R(18) or $(C_3-C_8)$-alkenyl;

al is zero, 1 or 2;

R(18) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(19a)R(19b);

R(19a) and R(19b) are hydrogen, $(C_1-C_4)$-alkyl or $(C_1-C_4)$-perfluoroalkyl; or R(3), R(4), R(5), R(6) and R(7) independently of one another are $(C_1-C_9)$-heteroaryl, which is linked via C or N and which is unsubstituted or substituted by 1–3 substituents from the group consisting of F, Cl, $CF_3$, $CH_3$, methoxy, hydroxyl, amino, methylamino or dimethylamino; or R(3), R(4), R(5), R(6) and R(7)

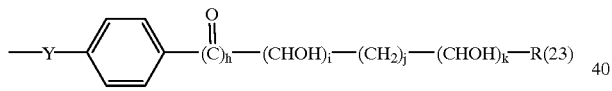

independently of one another are

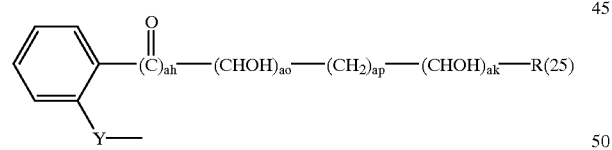

or

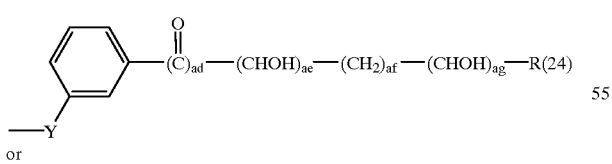

Y is oxygen, —S— or —NR(22)—;

h, ad, ah independently of one another are zero or 1;

i, j, k, ae, af, ag, ao, ap and ak independently of one another are zero, 1, 2, 3 or 4;

but where in each case h, i and k are not simultaneously zero, ad, ae and ag are not simultaneously zero, and ah, ao and ak are not simultaneously zero, R(23), R(24) R(25) and R(22) independently of one another are hydrogen or $(C_1-C_3)$-alkyl; or R(3), R(4), R(5), R(6) and R(7) independently of one another are SR(29), —OR(30), —NR(31)R(32) or —CR(33)R(34)R(35);

R(29), R(30), R(31) and R(33) independently of one another are —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(32), R(34) and R(35) independently of one another are defined as R(29) or are hydrogen, $(C_1-C_4)$-alkyl or $(C_1-C_4)$-perfluoroalkyl; or R(3), R(4), R(5), R(6) and R(7) independently of one another are

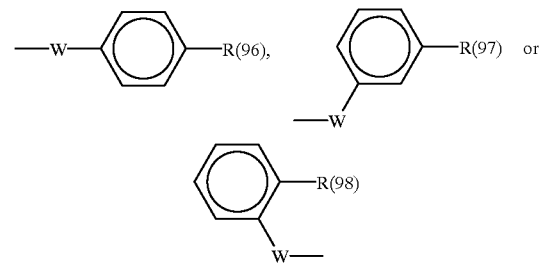

R(96), R(97) and R(98) independently of one another are $(C_1-C_9)$-heteroaryl, which is linked via C or N and which is unsubstitued or substituted by 1 to 3 substituents from the group consisting of F, Cl, $CF_3$, $CH_3$, methoxy, hydroxyl, amino, methylamino, dimethylamino or benzyl;

W is oxygen, S or NR(36)—;

R(36) is H or $(C_1-C_4)$-alkyl; or

R(3), R(4), R(5), R(6) and R(7) independently of one another are R(46)X(1)—;

X(1) is oxygen, S, NR(47), (D=O)A— or NR(48)C=MN$^{(+)}$R(49)—;

M is oxygen or sulfur;

A is oxygen or NR(50);

D is C or SO;

R(46) is $(C_1-C_8)$-alkyl, $(C_3-C_8)$-alkenyl, $(CH_2)_bC_dF_{2d+1}$, or —$C_xH_{2x}$—R(51);

b is zero or 1;

d is 1, 2, 3, 4, 5, 6 or 7;

x is zero, 1, 2, 3 or 4;

R(51) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(52)R(53);

R(52) and R(53) are hydrogen, $(C_1-C_4)$-alkyl or $(C_1-C_4)$-perfluoroalkyl;

R(47), R(48) and R(50) independently are hydrogen, $(C_1-C_4)$-alkyl or $(C_1-C_4)$-perfluoroalkyl;

R(49) is defined as R(46); or

R(46) and R(47), or R(46) and R(48) together are 4 or 5 methylene groups, of which one $CH_2$ groups can be replaced by oxygen, sulfur, NH, N—$CH_3$ or N-benzyl;

here A and N$^{(*)}$ are bonded to the phenyl nucleus of the heteroaroylguanidine parent structure; or R(3), R(4), R(5), R(6) and R(7) independently of one another are —SR(64), —OR(65), —NHR(66), —NR(67)R(68), —CHR(69)R(70) or —CR(54)R(55)OH, —C≡CR(56), —CR(58)=CR(57) or —[CR(59)R(60)]$_u$—CO—[CR(61)R(62)]$_v$—R(63);

R(64), R(65), R(66), R(67) and R(69) identically or differently are —(CH$_2$)$_y$—(CHOH)$_z$—(CH$_2$)$_{aa}$—(CHOH)$_t$—R(71) or —(CH$_2$)$_{ab}$—O—(CH$_2$—CH$_2$O)$_{ac}$—R(72);

R(71) and R(72) independently of one another are hydrogen or methyl;

u is 1, 2, 3 or 4;

v is zero, 1, 2, 3 or 4;

y, z, aa identically or differently are zero, 1, 2, 3 or 4;

t is 1, 2, 3 or 4;

R(68), R(70), R(54) and R(55) identically or differently are hydrogen or (C$_1$–C$_9$)-alkyl; or R(69) and R(70), or R(54) and R(55) together with the carbon atom carrying them are (C$_3$–C$_8$)-cycloalkyl;

R(63) is hydrogen, (C$_1$–C$_6$)-alkyl, (C$_3$–C$_8$)-cycloalkyl or —C$_e$H$_{2e}$—R(73);

e is zero, 1, 2, 3 or 4;

R(56), R(57) and R(73) independently are phenyl, which is unsubstituted or substituted by 1–3 substituents selected from the group consisting of F, Cl, CF$_3$, methyl, methoxy and NR(74)R(75);

R(74) and R(75) are hydrogen or (C$_1$–C$_4$)-alkyl; or

R(56), R(57) and R(73) independently are (C$_1$–C$_9$)-heteroaryl, which is unsubstituted or substituted as phenyl;

R(58), R(59), R(60), R(61) and R(62) are hydrogen or methyl; or

R(3), R(4), R(5), R(6) and R(7) independently of one another are R(76)—NH—SO$_2$—;

R(76) is R(77)R(78)N—(C=Y')—;

Y' is oxygen, S or N—R(79);

R(77) and R(78) identically or differently are hydrogen, (C$_1$–C$_8$)-alkyl, (C$_3$–C$_6$)-alkenyl or —C$_f$H$_{2f}$—R(80);

f is zero, 1, 2, 3 or 4;

R(80) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl; or R(77) and R(78) together are 4 or 5 methylene groups, of which one CH$_2$ group can be replaced by oxygen, sulfur, NH, N—CH$_3$ or N-benzyl;

R(79) is defined as R(77) or is amidine; or

R(3), R(4), R(5), R(6) and R(7) independently of one another are NR(84a)R(85), OR(84b), SR(84c) or —C$_n$H$_{2n}$—R(84d);

n is zero, 1, 2, 3 or 4;

R(84d) is (C$_3$–C$_7$)-cycloalkyl or phenyl, which is not substituted or is substituted by 1–3 substituents from the group consisting of F, Cl, CF$_3$, methyl, methoxy and NR(16)R(17);

R(16) and R(17) are hydrogen or C$_1$–C$_4$-alkyl;

R(84a), R(84b), R(84c) and R(85) independently of one another are hydrogen, (C$_1$–C$_8$)-alkyl, (C$_1$–C$_8$)-perfluoroalkyl or (CH$_2$)$_{ax}$—R(84g);

ax is zero, 1, 2, 3 or 4;

R(84g) is (C$_3$–C$_7$)-cycloalkyl or phenyl, which is not substituted or is substituted by 1–3 substituents selected from the group consisting of F, Cl, CF$_3$, methyl, methoxy and NR(84u)R(84v);

R(84u) and R(84v) are hydrogen or C$_1$–C$_4$-alkyl; or

R(84a) and R(85) together are 4 or 5 methylene groups, of which one CH$_2$ group can be replaced by oxygen, sulfur, NH, N—CH$_3$ or N-benzyl, and their pharmaceutically tolerable salts;

(HOE 94/F 134—EP-Offenlegungsschrift 686 627, NZ 272 103)

z) benzoylguanidines of the formula I

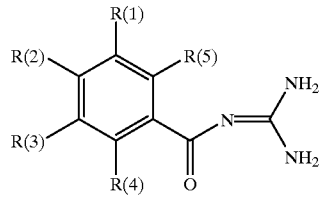

I in which:

R(1) is R(6)—SO$_m$;

m is zero, 1 or 2;

R(6) is perfluoroalkyl having 1, 2, 3, 4, 5 or 6 carbon atoms, which is straight-chain or branched;

R(2) and R(3) independently of one another are hydrogen, F, Cl, Br, I, alkyl having 1, 2, 3 or 4 carbon atoms, alkoxy having 1, 2, 3 or 4 carbon atoms or phenoxy, which is unsubstituted or substituted by 1–3 substituents selected from the group consisting of F, Cl, methyl and methoxy; or R(2) and R(3) independently of one another are pyrrol-1-yl, pyrrol-2-yl or pyrrol-3-yl, which is not substituted or is substituted by 1 to 4 substituents selected from the group consisting of F, Cl, Br, I, CN, alkanoyl having 2, 3, 4, 5, 6, 7 or 8 carbon atoms, alkoxycarbonyl having 2, 3, 4, 5, 6, 7 or 8 carbon atoms, formyl, carboxyl, CF$_3$, methyl and methoxy;

R(4) and R(5) independently of one another are hydrogen, alkyl having 1, 2 or 3 carbon atoms, F, Cl, Br, I, CN, OR(7), NR(8)R(9) or —(CH$_2$)$_n$—(CF$_2$)$_{o-CF3}$;

R(7), R(8) and R(9) independently of one another are hydrogen or alkyl having 1, 2, 3 or 4 carbon atoms;

n is zero or 1;

o is zero, 1 or 2;

and their pharmacologically acceptable salts;

(HOE 94/F 168—EP-Offenlegungsschrift 690 048, NZ 272 373)

ab) Phenyl-substituted alkenylcarboxylic acid guanidides, carrying perfluoroalkyl groups, of the formula I

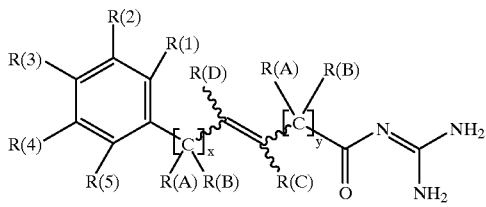

I in which:

R(A) is hydrogen, F, Cl, Br, I, CN, OH, OR(6), (C$_1$–C$_8$)-alkyl, O$_r$(CH$_2$)$_a$C$_b$F$_{2b+1}$, (C$_3$–C$_8$)-cycloalkyl or NR(7)R(8);

r is zero or 1;
a is zero, 1, 2, 3 or 4;
b is 1, 2, 3, 4, 5, 6, 7 or 8;
R(6) is $(C_1-C_8)$-alkyl, $(C_1-C_4)$-perfluoroalkyl, $(C_3-C_8)$-alkenyl, $(C_3-C_8)$-cycloalkyl, phenyl or benzyl;
where the aromatics are not substituted or are substituted by 1–3 substituents from the group consisting of F, Cl, $CF_3$, methyl, methoxy and NR(9)R(10);
R(9) and R(10) are H, $(C_1-C_4)$-alkyl or $(C_1-C_4)$-perfluoroalkyl;
R(7) and R(8) independently of one another are defined as R(6); or
R(7) and R(8) together are 4 or 5 methylene groups, of which one $CH_2$ group can be replaced by oxygen, sulfur, NH, N—$CH_3$ or N-benzyl;
R(B) independently is defined as R(A);
x is zero, 1 or 2;
y is zero, 1 or 2;
R(C) is hydrogen, F, Cl, Br, I, CN, OR(12), $(C_1-C_8)$-alkyl, $O_p(CH_2)_f C_g F_{2g+1}$ or $(C_3-C_8)$-cycloalkyl;
p is zero or 1;
f is zero, 1, 2, 3 or 4;
g is 1, 2, 3, 4, 5, 6, 7 or 8;
R(12) is $(C_1-C_8)$-alkyl, $(C_1-C_4)$-perfluoroalkyl, $(C_3-C_8)$-alkenyl, $(C_3-C_8)$-cycloalkyl, phenyl or benzyl;
where the aromatics phenyl or benzyl are not substituted or are substituted by 1–3 substituents from the group consisting of F, Cl, $CF_3$, methyl, methoxy and NR(13)R(14);
R(13) and R(14) independently of one another are H, $(C_1-C_4)$-alkyl or $(C_1-C_4)$-perfluoroalkyl;
R(D) independently is defined as R(C),
R(1) is hydrogen, $(C_1-C_8)$-alkyl, $-O_t(CH_2)_d C_e F_{2e+1}$, $(C_3-C_8)$-cycloalkyl, F, Cl, Br, I or CN;
t is zero or 1;
d is zero, 1, 2, 3 or 4;
e is 1, 2, 3, 4, 5, 6, 7 or 8;
R(2), R(3), R(4) and R(5) independently of one another are defined as R(1);
but with the condition that at least one of the substituents R(A), R(B), R(C), R(D), R(1), R(2), R(4) or R(5) is a $O_r(CH_2)_a C_b F_{2b+1}$, $O_p(CH_2)_f C_g F_{2g+1}$ or $O_t(CH_2)_d C_e F_{2e+1}$ group and R(3) is not a $O_t(CH_2)_d C_e F_{2e+1}$ group;
and their pharmaceutically tolerable salts;
(HOE 94/F 182—EP-Offenlegungsschrift 690 048, NZ 272 449)

ac) ortho-amino-substituted benzoylguanidines of the formula I

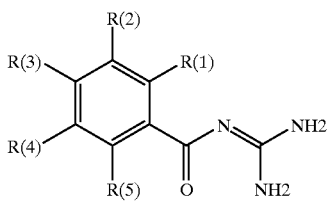

I in which:
R(1) is NR(50)R(6),
R(50) and R(6) independently of one another are hydrogen, $(C_1-C_8)$-alkyl or $(C_1-C_8)$-perfluoroalkyl;

R(2), R(3), R(4) and R(5) independently of one another are R(10)—$SO_{a-R}$(11)R(12)N—CO—, R(13)—CO— or R(14)R(15)N—$SO_2$—;
a is zero, 1 or 2,
R(10), R(11), R(12), R(13), R(14) and R(15) independently of one another are $(C_1-C_8)$-alkyl, $(C_1-C_8)$-perfluoroalkyl, $(C_3-C_6)$-alkenyl or —$C_{ab}H_{2ab}$—R(16);
ab is zero, 1, 2, 3 or 4;
R(16) is $(C_3-C_7)$-cycloalkyl, phenyl,
which is not substituted or is substituted by 1–3 substituents selected from the group consisting of F, Cl, $CF_3$, methyl, methoxy and NR(17)R(18);
R(17) and R(18) independently of one another are H, $CF_3$ or $(C_1-C_4)$-alkyl; or
R(11), R(12), and also R(14) and R(15) together are 4 or 5 methylene groups, of which one $CH_2$ group can be replaced by oxygen, S, NH, N—$CH_3$ or N-benzyl; or
R(11), R(12), R(14) and R(15) independently of one another are hydrogen; or
R(2), R(3), R(4) and R(5) independently of one another are SR(21), —OR(22), —NR(23)R(24) or —CR(25)R(26)R(27);
R(21), R(22), R(23) and R(25) independently of one another are —$C_b H_{2b}$—$(C_1-C_9)$-heteroaryl,
which is unsubstituted or substituted by 1–3 substituents selected from the group consisting of F, Cl, $CF_3$, $CH_3$, methoxy, hydroxyl, amino, methylamino and dimethylamino;
b is zero, 1 or 2;
R(24), R(26) and R(27) independently of one another are hydrogen, $(C_1-C_4)$-alkyl or $(C_1-C_4)$-perfluoroalkyl; or
R(2), R(3), R(4) and R(5) independently of one another are hydrogen, F, Cl, Br, I, CN, —$(Xa)_{dg}$—$C_{da}H_{2da+1}$, —$(Xb)_{dh}$—$(CH_2)_{db}$—$C_{de}F_{2de+1}$, $(C_3-C_8)$-alkenyl or —$C_{df}H_{2df}$R(30);
(Xa) is O, S or NR(33);
R(33)
is H, $(C_1-C_4)$-alkyl or $(C_1-C_4)$-perfluoroalkyl;
dg is zero or 1;
(Xb) is O, S or NR(34);
R(34) is H, $(C_1-C_4)$-alkyl or $(C_1-C_4)$-perfluoroalkyl;
dh is zero or 1;
da is zero, 1, 2, 3, 4, 5, 6, 7, 8;
db is zero, 1, 2, 3, 4;
de is zero, 1, 2, 3, 4, 5, 6, 7;
df is zero, 1, 2, 3, 4;
R(30) is $(C_3-C_8)$-cycloalkyl, phenyl, biphenylyl or naphthyl, where the aromatics phenyl, biphenylyl or naphthyl are not substituted or are substituted by 1–3 substituents selected from the group consisting of F, Cl, $CF_3$, methyl, methoxy and NR(31)R(32);
R(31) and R(32) are H, $(C_1-C_4)$-alkyl or $(C_1-C_4)$-perfluoroalkyl; or
R(2), R(3), R(4) and R(5) independently of one another are NR(40)R(41) or —(Xe)—$(CH_2)_{eb}$R(45);
R(40) and R(41) independently of one another are hydrogen, $(C_1-C_8)$-alkyl, $(C_1-C_8)$-perfluoroalkyl or $(CH_2)_e$—R(42);
e is zero, 1, 2, 3 or 4;
R(42) is $(C_3-C_7)$-cycloalkyl, phenyl, which is not substituted or is substituted by 1–3 substituents selected from the group consisting of F, Cl, $CF_3$, methyl, methoxy and NR(43)R(44);

R(43) and R(44) independently of one another are H, CF$_3$ or (C$_1$–C$_4$)-alkyl; or R(40) and R(41) together are 4 or 5 methylene groups, of which one CH$_2$ group can be replaced by oxygen, sulfur, NH, N—CH$_3$ or N-benzyl;

(Xe) is O, S or NR(47);
R(47) is H, (C$_1$–C$_4$)-alkyl or (C$_1$–C$_4$)-perfluoroalkyl;

eb is zero, 1, 2, 3 or 4;

R(45) is (C$_3$–C$_7$)-cycloalkyl, phenyl, which is not substituted or is substituted by 1–3 substituents selected from the group consisting of F, Cl, CF$_3$, methyl, methoxy, NR(50)R(51) and —(Xfa)—(CH$_2$)$_{ed}$—(Xfb)R(46);

Xfa is CH$_2$, O, S or NR(48);

Xfb is O, S or NR(49);

ed is 1, 2, 3 or 4;

R(46) is H, (C$_1$–C$_4$)-alkyl or (C$_1$–C$_4$)-perfluoroalkyl;

R(48), R(49), R(50) and R(51) independently of one another are H or (C$_1$–C$_4$)-alkyl or (C$_1$–C$_4$)-perfluoroalkyl;

where R(3) and R(4), however, cannot be hydrogen, and their pharmaceutically tolerable salts;

(HOE 94/F 265—NZ 272 946, EP-Offenlegungsschrift 700 904)

ad) benzoylguanidines of the formula I

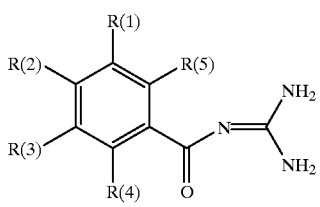

in which:

one of the three substituents R(1), R(2) and R(3) is (C$_1$–C$_9$)-heteroaryl-N-oxide,
which is linked via C or N and which is unsubstituted or substituted by 1–3 substituents selected from the group consisting of F, Cl, CF$_3$, CH$_3$, methoxy, hydroxyl, amino, methylamino and dimethylamino; or one of the three substituents R(1), R(2) and R(3) is —SR(10), —OR(10), —NR(10)R(11) or —CR(10)R(11)R(12);

R(10) is —C$_a$H$_{2a}$—(C$_1$–C$_9$)-heteroaryl-N-oxide,
which is unsubstituted or substituted by 1–3 substituents selected from the group consisting of F, Cl, CF$_3$, CH$_3$, methoxy, hydroxyl, amino, methylamino and dimethylamino;

a is zero, 1 or 2;

R(11) and R(12) independently of one another are defined as R(10), are hydrogen or (C$_1$–C$_4$)-alkyl;

and the other substituents R(1), R(2) and R(3) in each case independently of one another are (C$_1$–C$_8$)-alkyl, (C$_2$–C$_8$)-alkenyl or —C$_m$H$_{2m}$R(14);

m is zero, 1 or 2;

R(14) is (C$_3$–C$_8$)-cycloalkyl or phenyl,
which is not substituted or is substituted by 1–3 substituents selected from the group consisting of F, Cl, CF$_3$, methyl, methoxy and NR(15)R(16), R(15) and R(16) are hydrogen or CH$_3$; or the other substituents R(1), R(2) and R(3) in each case independently of one another are hydrogen, F, Cl, Br, I, —C≡N, X—(CH$_2$)$_p$—(C$_q$F$_{2q+1}$), R(22)—SO$_u$, R(23)R(24)N—CO, R(25)—CO— or R(26)R(27)N—SO$_2$—, where the perfluoroalkyl group is straight-chain or branched;

X is a bond, oxygen, S or NR(28);

u is zero, 1 or 2;

p is zero, 1 or 2;

q is zero, 1, 2, 3, 4, 5 or 6;

R(22), R(23), R(25) and R(26) independently are (C$_1$–C$_8$)-alkyl, (C$_2$–C$_6$)-alkenyl, —C$_n$H$_{2n}$—R(29) or CF$_3$;

n is zero, 1, 2, 3 or 4;

R(28) is hydrogen or (C$_1$–C$_3$)-alkyl;

R(29) is (C$_3$–C$_7$)-cycloalkyl or phenyl;
which is not substituted or is substituted by 1–3 substituents selected from the group consisting of F, Cl, CF$_3$, methyl, methoxy and NR(30)R(31);

R(30) and R(31) are hydrogen or C$_1$–C$_4$-alkyl, or

R(23), R(25) and R(26) are also hydrogen;

R(24) and R(27) independently of one another are hydrogen or (C$_1$–C$_4$)-alkyl; or R(23) and R(24), and also R(26) and R(27) together are 4 or 5 methylene groups, of which one CH$_2$ group can be replaced by oxygen, S, NH, N—CH$_3$ or N-benzyl; or the other substituents R(1), R(2) and R(3) in each case independently of one another are OR(35) or NR(35)R(36);

R(35) and R(36) independently of one another are hydrogen or (C$_1$–C$_6$)-alkyl; or R(35) and R(36) together are 4–7 methylene groups, of which one CH$_2$ group can be replaced by oxygen, S, NH, N—CH$_3$ or N-benzyl, R(4) and R(5) independently of one another are hydrogen, (C$_1$–C$_4$)-alkyl, F, Cl, —OR(32), —NR(33)R(34) or C$_r$F$_{2r+1}$;

R(32), R(33) and R(34) independently of one another are hydrogen or (C$_1$–C$_3$)-alkyl;

r is 1, 2, 3 or 4;

and their pharmaceutically tolerable salts;

(HOE 94/F 266—EP-Offenlegungsschrift 702 001, NZ 272 948)

ae) benzoylguanidines of the formula I

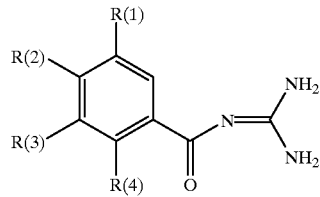

in which:

R(1) is hydrogen, F, Cl, Br, I, CN, NO$_2$, OH, (C$_1$–C$_8$)-alkyl, (C$_3$–C$_8$)-cycloalkyl, O$_a$—(CH$_2$)$_b$—(CF$_2$)$_c$—CF$_3$;

a is zero or 1;

b is zero, 1 or 2;

c is zero, 1, 2 or 3; or

R(1) is R(5)—SO$_m$ or R(6)R(7)N—SO$_2$—;

m is zero, 1 or 2;

R(5) and R(6) independently of one another are (C$_1$–C$_8$)-alkyl, (C$_3$–C$_6$)-alkenyl, CF$_3$ or —C$_n$H$_{2n}$—R(8);

n is zero, 1, 2, 3 or 4;

R(7) is hydrogen or $(C_1-C_4)$-alkyl;

R(8) is $(C_3-C_7)$-cycloalkyl or phenyl,
which is not substituted or is substituted by 1–3 substituents selected from the group consisting of F, Cl, $CF_3$, methyl, methoxy and NR(9)R(10);

R(9) and R(10) independently of one another are hydrogen or $(C_1-C_4)$-alkyl; or R(6) is H;

or R(6) and R(7) together are 4 or 5 methylene groups, of which one $CH_2$ group can be replaced by oxygen, S, NH, N—$CH_3$ or N-benzyl, or R(1) is —SR(11), —OR(11) or —CR(11)R(12)R(13);

R(11) is —$C_pH_{2p}$—$(C_3-C_8)$-cycloalkyl, —$(C_1-C_9)$-heteroaryl or phenyl,
where the aromatic systems are unsubstituted or substituted by 1–3 substituents selected from the group consisting of F, Cl, $CF_3$, $CH_3$, methoxy, hydroxyl, amino, methylamino and dimethylamino;

R(12), R(13) independently of one another are defined as R(11) or are hydrogen or $(C_1-C_4)$-alkyl;

p is zero, 1 or 2; or

R(1) is phenyl, naphthyl, biphenylyl or $(C_1-C_9)$-heteroaryl, the latter linked via C or N,
which are unsubstituted or substituted by 1–3 substituents selected from the group consisting of F, Cl, $CF_3$, $CH_3$, methoxy, hydroxyl, amino, methylamino and dimethylamino;

R(2) is —$CF_2$R(14), —CF[R(15)][(R(16)], —CF[$(CF_2)_q$—$CF_3$)][R(15)], —C[$(CF_2)_r$—$CF_3$]=CR(15)R(16);

R(14) is $(C_1-C_4)$-alkyl or $(C_3-C_6)$-cycloalkyl;

R(15) and R(16) independently of one another are hydrogen or $(C_1-C_4)$-alkyl;

q is zero, 1 or 2;

r is zero, 1 or 2;

R(3) is defined as R(1);

R(4) is hydrogen, $(C_1-C_3)$-alkyl, F, Cl, Br, I, CN, —$(CH_2)_s$—$(CF_2)_t$—$CF_3$;

s is zero or 1;

t is zero, 1 or 2;

and their pharmaceutically tolerable salts;

(HOE 94/F 267—EP-Offenlegungsschrift 700 899, NZ 272 947)

af) benzoylguanidines of the formula I

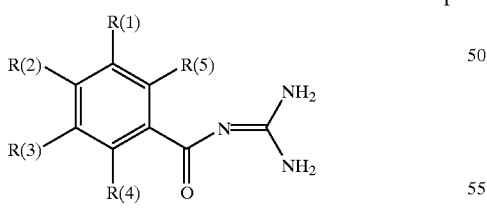

I in which:

one of the three substituents R(1), R(2) and R(3) is —Y4—[$(CH_2)_k$—CHR(7)—(C=O)R(8)]-phenyl, —Y-3-$(CH_2)_k$—CHR(7)—(C=O)R(8)]phenyl or —Y-2—[$(CH_2)_k$—CHR(7)—(C=O)R(8)]-phenyl,
where the phenyl in each case is unsubstituted or substituted by 1–2 substituents from the group F, Cl, —$CF_3$, methyl, hydroxyl, methoxy, or —NR(37)R(38);

R(37) and R(38) independently of one another are hydrogen or —$CH_3$;

Y is a bond, oxygen, —S— or —NR(9);

R(9) is hydrogen or —$(C_1-C_4)$-alkyl;

R(7) is —OR(10) or —NR(10)R(11);

R(10) and R(11) independently of one another are hydrogen, —$(C_1-C_8)$-alkyl, —$(C_1-C_8)$-alkanoyl, —$(C_1-C_8)$-alkoxycarbonyl, benzyl, benzyloxycarbonyl; or R(10) is trityl;

R(8) is —OR(12) or —NR(12)R(13);

R(12) and R(13) independently of one another are hydrogen, —$(C_1-C_8)$-alkyl or benzyl;

k is zero, 1, 2, 3 or 4;

and the other radicals R(1), R(2) and R(3) in each case independently of one another are —$(C_1-C_8)$-alkyl, —$(C_2-C_8)$-alkenyl or —$(CH_2)_m$R(14);

m is zero, 1 or 2;

R(14) is —$(C_3-C_8)$-cycloalkyl or phenyl,
which is not substituted or is substituted by 1–3 substituents selected from the group consisting of F, Cl, —$CF_3$, methyl, methoxy and —NR(15)R(16);

R(15) and R(16) are hydrogen or —$CH_3$; or the other radicals R(1), R(2) and R(3) in each case independently of one another are R(18)R(19)N—(C=Y')—NH—$SO_2$—;

Y' is oxygen, —S— or —N—R(20);

R(18) and R(19) independently of one another are hydrogen, —$(C_1-C_8)$-alkyl, —$(C_3-C_6)$-alkenyl or —$(CH_2)_t$—R(21);

t is zero, 1, 2, 3 or 4;

R(21) is —$(C_5-C_7)$-cycloalkyl or phenyl,
which is unsubstituted or substituted by 1–3 substituents selected from the group consisting of F, Cl, —$CF_3$, methoxy and —$(C_1-C_4)$-alkyl; or R(18) and R(19) together are 4 or 5 methylene groups, of which one $CH_2$ group can be replaced by oxygen, —S—, —NH—, —N—$CH_3$ or —N-benzyl;

R(20) is defined as R(18) or is amidine; or the other radicals R(1), R(2) and R(3) in each case independently of one another are hydrogen, F, Cl, Br, I, —C≡N, X—$(CH_2)_p$—$(C_qF_{2q+1})$, R(22)—$SO_u$—, R(23)R(24)N—CO—, R(25)CO— or R(26)R(27)N—$SO_2$—, where the perfluoroalkyl group is straight-chain or branched;

X is a bond, oxygen, —S— or —NR(28);

u is zero, 1 or 2;

p is zero, 1 or 2;

q is 1, 2, 3, 4, 5 or 6;

R(22), R(23), R(25) and R(26) independently of one another are —$(C_1-C_8)$-alkyl, —$(C_3-C_6)$-alkenyl, —$(CH_2)_n$—R(29) or —$CF_3$;

n is zero, 1, 2, 3 or 4;

R(28) is hydrogen or —$(C_1-C_3)$-alkyl;

R(29) is —$(C_3-C_7)$-cycloalkyl or phenyl,
which is not substituted or is substituted by 1–3 substituents selected from the group consisting of F, Cl, —$CF_3$, methyl, methoxy and —NR(30)R(31);

R(30) and R(31) are hydrogen or —$(C_1-C_4)$-alkyl; or

R(23), R(25) and R(26) are hydrogen;

R(24) and R(27) independently of one another are hydrogen or —$(C_1-C_4)$-alkyl; or R(23) and R(24), and also R(26) and R(27) together are 4 or 5 methylene groups, of which one $CH_2$ group can be replaced by oxygen, —S—, —NH—, —N—$CH_3$ or —N-benzyl; or the other radicals R(1), R(2) and R(3) in each case independently of one another are —OR(35) or —NR(35)R(36);

R(35) and R(36) independently of one another are hydrogen or —$(C_1-C_6)$-alkyl; or R(35) and R(36) together are 4–7 methylene groups, of which one $CH_2$ group can be replaced by oxygen, —S—, —NH—, —N—$CH_3$ or —N-benzyl;

R(4) and R(5) independently of one another are hydrogen, —$(C_1-C_4)$-alkyl, F, Cl, —OR(32), —NR(33)R(34) or —$C_rF_{2r+1}$;

R(32), R(33) and R(34) independently of one another are hydrogen or —$(C_1-C_3)$-alkyl;

r is 1, 2, 3 or 4;

and their pharmaceutically tolerable salts;

(HOE 94/F 352—EP-Offenlegungsschrift 713 684, NZ 280 517)

ag) benzoylguanidines of the formula I

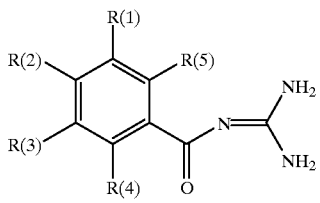

I in which:

R(1) is R(6)—CO or R(7)R(8)N—CO;

R(6) is $(C_1-C_8)$-alkyl, $(C_1-C_8)$-perfluoroalkyl, $(C_3-C_8)$-alkenyl or —$C_nH_{2n}$—R(9), n is zero, 1, 2, 3 or 4;

R(9) is $(C_3-C_8)$cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11), R(10) and R(11) are H, $(C_1-C_4)$-alkyl or $(C_1-C_4)$-perfluoroalkyl;

R(7) is H, $(C_1-C_8)$-alkyl, $(C_1-C_8)$-perfluoroalkyl, $(C_3-C_8)$-alkenyl or —$C_nH_{2n}$—R(12);

n is zero, 1, 2, 3 or 4;

R(12) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);

R(13) and R(14) are H, $(C_1-C_4)$-alkyl or, $(C_1-C_4)$-perfluoroalkyl;

R(8) is H, $(C_1-C_4)$-alkyl or $(C_1-C_4)$-perfluoroalkyl; or

R(7) and R(8) together are 4 or 5 methylene groups, of which one $CH_2$ group can be replaced by oxygen, S, NH, N—$CH_3$ or N-benzyl;

R(2) is defined as R(1), or is H, OH, F, Cl, Br, I, CN, $NO_2$, $(C_1-C_8)$-alkyl, $(C_1-C_8)$-perfluoroalkyl, $(C_3-C_8)$-alkenyl or —$C_nH_{2n}$R(15);

n is zero, 1, 2, 3 or 4;

R(15) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);

R(16) and R(17) are H, $(C_1-C_4)$-alkyl or $(C_1-C_4)$-perfluoroalkyl; or

R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or R(2) is SR(18), —OR(18), —NR(18)R(19) or —CR(18)R(19)R(20);

R(18) is $C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino, dimethylamino;

a is zero, 1 or 2;

R(19) and R(20) independently of one another are defined as R(18) or are hydrogen, $(C_1-C_4)$-alkyl or $(C_1-C_4)$-perfluoroalkyl; or R(2) is R(21)—$SO_m$ or R(22)R(23)N—$SO_2$—;

m is 1 or 2;

R(21) is $(C_1-C_8)$-alkyl, $(C_1-C_8)$-perfluoroalkyl, $(C_3-C_8)$-alkenyl or —$C_nH_{2n}$—R(24);

n is zero, 1, 2, 3 or 4;

R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);

R(27) and R(28) are H, $(C_1-C_4)$-alkyl or $(C_1-C_4)$-perfluoroalkyl;

R(22) is H, $(C_1-C_8)$-alkyl, $(C_1-C_8)$-perfluoroalkyl, $(C_3-C_8)$-alkenyl or —$C_nH_{2n}$—R(29);

n is zero, 1, 2, 3 or 4;

R(29) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);

R(30) and R(31) are H, $(C_1-C_4)$-alkyl or $(C_1-C_4)$-perfluoroalkyl;

R(23) is hydrogen, $(C_1-C_4)$-alkyl or $(C_1-C_4)$-perfluoroalkyl; or

R(22) and R(23) together are 4 or 5 methylene groups, of which one $CH_2$ group can be replaced by oxygen, S, NH, N—$CH_3$ or N-benzyl; or R(2) is R(33)X—;

X is oxygen, S, NR(34), (D=O)A— or NR(34)C=MN$^{(*)}$R(35)—;

M is oxygen or S;

A is oxygen or NR(34);

D is C or SO;

R(33) is $(C_1-C_8)$-alkyl, $(C_3-C_8)$-alkenyl, $(CH_2)_bC_dF_{2d+1}$ or —$C_nH_{2n}$—R(36);

b is zero or 1;

d is 1, 2, 3, 4, 5, 6 or 7;

n is zero, 1, 2, 3, or 4;

R(36) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);

R(37) and R(38) are H, $(C_1-C_4)$-alkyl or $(C_1-C_4)$-perfluoroalkyl;

R(34) is hydrogen, $(C_1-C_4)$-alkyl or $(C_1-C_4)$-perfluoroalkyl;

R(35) is defined as R(33); or

R(33) and R(34) together are 4 or 5 methylene groups, of which one $CH_2$ group can be replaced by oxygen, S, NH, N—$CH_3$ or N-benzyl;

where A and N$^{(*)}$ are bonded to the phenyl nucleus of the benzoylguanidine parent structure; or R(2) is —SR(40), —OR(40), —NHR(40), —NR(40)R(41), —CHR(40)R(42), —CR(42)R(43)OH, —C≡CR(45), —CR(46)=CR(45) or —[CR(47)R(48)]$_u$—CO—[C(R49)R(50)]$_v$—R(44);

R(40) and R(41) independently of one another are —(CH$_2$)$_p$—(CHOH)$_q$—(CH$_2$)$_r$—(CHOH)$_t$—R(51) or (CH$_2$)$_p$—O—(CH$_2$CH$_2$O)$_q$—R(51);

R(51) is hydrogen or methyl;

u is 1, 2, 3 or 4;

v is zero, 1, 2, 3 or 4;

p, q and r independently of one another are zero, 1, 2, 3 or 4;

t is 1, 2, 3 or 4;

R(42) and R(43) independently of one another are hydrogen or (C$_1$–C$_6$)-alkyl; or R(42) and R(43) together with the carbon atom carrying them are a (C$_3$–C$_8$)-cycloalkyl;

R(44) is hydrogen, (C$_1$–C$_6$)-alkyl, (C$_3$–C$_8$)-cycloalkyl, —C$_e$H$_{2e}$—R(45);

e is zero, 1, 2, 3 or 4;

R(45) is phenyl, which is unsubstituted or substituted by 1–3 substituents selected from the group consisting of F, Cl, CF$_3$, methyl, methoxy and NR(52)R(53);

R(52) and R(53) are H or (C$_1$–C$_4$)-alkyl; or

R(45) is (C$_1$–C$_9$)-heteroaryl, which is unsubstituted or substituted as phenyl; or R(45) is (C$_1$–C$_6$)-alkyl, which is unsubstituted or substituted by 1–3 OH;

R(46), R(47), R(48), R(49) and R(50) independently of one another are hydrogen or methyl; or R(2) is R(55)—NH—SO$_2$—;

R(55) is R(56)R(57)N—(C=Y)—;

Y is oxygen, S or N—R(58);

R(56) and R(57) independently of one another are hydrogen, (C$_1$–C$_8$)-alkyl, (C$_3$–C$_6$)-alkenyl or —C$_f$H$_{2f}$—R(59);

f is zero, 1, 2, 3 or 4;

R(59) is (C$_5$–C$_7$)-cycloalkyl, phenyl, which is unsubstituted or substituted by 1–3 substituents selected from the group consisting of F, Cl, CF$_3$, methoxy. and (C$_1$–C$_4$)-alkyl; or R(56) and R(57) together are 4 or 5 methylene groups, of which one CH$_2$ group can be replaced by oxygen, S, NH, N—CH$_3$ or N-benzyl;

R(58) is defined as R(56) or is amidine;

R(3), R(4) and R(5) are independently of one another defined as R(1) or R(2), but where at least one of the substituents R(2), R(3), R(4) and R(5) must be OH;

and their pharmaceutically tolerable salts;

(HOE 95/F 007 K—EP-Offenlegungsschrift 723 956, NZ 280 887)

ah) benzoylguanidines of the formula I

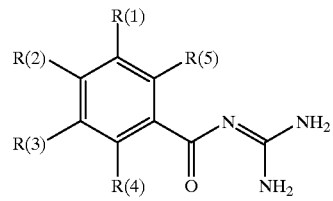

in which:

one of the three substituents R(1), R(2) and R(3) is R(6)—A—B—D—;

R(6) is a basic protonatable radical, i.e. an amino group —NR(7)R(8), an amidino group R(7)R(8)N—C[=N—R(9)]— or a guanidino group

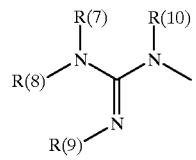

R(7), R(8), R(9) and R(10) independently of one another are hydrogen or alkyl having 1, 2, 3 or 4 carbon atoms; or R(7) and R(8) together are C$_a$H$_{2a}$;

a is 4, 5, 6 or 7;

where if a=5, 6 or 7 a methylene group of the group C$_a$H$_{2a}$ can be replaced by a heteroatom group O, SO$_m$ or NR(11), or R(8) and R(9) or R(9) and R(10) or R(7) and R(10) are a group C$_a$H$_{2a}$;

a is 2, 3, 4 or 5;

where if a=3, 4 or 5 a methylene group of the group C$_a$H$_{2a}$ can be replaced by a heteroatom group O, SO$_m$ or NR(11);

m is zero, 1 or 2;

R(11) is hydrogen or methyl; or

R(6) is a basic heteroaromatic ring system having 1–9 carbon atoms;

A is C$_b$H$_{2b}$;

b is 1, 2, 3, 4, 5, 6, 7, 8, 9 or 10;

where in the group C$_b$H$_{2b}$ one or two methylene groups can be replaced by one of the groupings selected from the group consisting of —O—, —CO—, —CH[OR(20)]—, —SO$_m$—, —NR(20)—, —NR(20)—CO—, —NR(20)—CO—NH—, —NR(20)—CO—NH—SO$_2$—

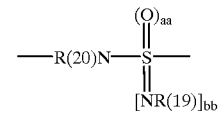

and —SO$_{aa}$[NR(19)]$_{bb}$—;

and where in the group C$_b$H$_{2b}$ a methylene group can be replaced by —CH—R(99), where R(99) together with R(7) forms a pyrrolidine or piperidine ring;

aa is 1 or 2;

bb is 0 or 1;

aa+bb=2;

R(19) is hydrogen or alkyl having 1, 2, 3 or 4 carbon atoms;
R(20) is hydrogen or methyl;
B is a phenylene or naphthylene radical

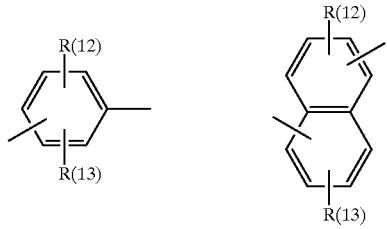

R(12) and R(13) independently of one another are hydrogen, methyl, F, Cl, Br, I, $CF_3$ or —$SO_{w}$—R(14);
R(14) is methyl or NR(15)R(16);
R(15) and R(16) independently of one another are hydrogen or alkyl having 1, 2, 3 or 4 carbon atoms;
w is zero, 1 or 2;
D is —$C_dH_{2d}$—$X_f$—;
d is zero, 1, 2, 3 or 4;
X is —O—, —CO—, —CH[OR(21)]—, —$SO_m$— or —NR(21)—;
f is zero or 1;
R(21) is hydrogen or methyl;
m is zero, 1 or 2;
and the other substituents R(1) and R(2) and R(3) in each case independently of one another are hydrogen, F, Cl, Br, I, —CN, —($C_1$–$C_8$)-alkyl, —($C_2$–$C_8$)-alkenyl, —NR(35)R(36) or R(17)—$C_gH_{2g}$—$Z_h$—;
g is zero, 1, 2, 3 or 4;
h is zero or 1;
R(35) and R(36) independently of one another are hydrogen or alkyl having 1, 2, 3, 4, 5 or 6 carbon atoms; or
R(35) and R(36) together are 4–7 methylene groups, of which one $CH_2$ group can be replaced by oxygen, —S—, —NH—, —$NCH_3$ or —N-benzyl;
Z is —O—, —CO—, —$SO_v$—, —NR(18)—, —NR(18)—CO—, —NR(18)—CO—NH— or —NR(18)—$SO_2$—;
R(18) is hydrogen or methyl;
v is zero, 1 or 2;
R(17) is hydrogen, cycloalkyl having 3, 5 or 6 carbon atoms or $C_kF_{2k+1}$—;
k is 1, 2 or 3, or
R(17) is pyrrol-1-yl, pyrrol-2-yl or pyrrol-3-yl, which is not substituted or is substituted by 1–4 substituents selected from the group consisting of F, Cl, Br, I, —CN, ($C_2$–$C_8$)-alkanoyl, ($C_2$–$C_8$)-alkoxycarbonyl, formyl, carboxyl, —$CF_3$, methyl and methoxy; or
R(17) is ($C_3$–$C_8$)-cycloalkyl or phenyl, which is not substituted or is substituted by 1–3 substituents selected from the group consisting of F and Cl, —$CF_3$, methyl, hydroxyl, methoxy, —NR(37)R(38), $CH_3SO_2$— and $H_2NO_2S$—;
R(37) and R(38) are hydrogen or —$CH_3$;
R(4) and R(5) independently of one another are hydrogen, alkyl having 1, 2, 3 or 4 carbon atoms, F, Cl, —OR(32), —NR(33)R(34) or —$C_rF_{2r+1}$;

R(32), R(33) and R(34) independently of one another are hydrogen or alkyl having 1, 2 or 3 carbon atoms;
r is 1, 2, 3 or 4;
and their pharmacologically tolerable salts;
(HOE 95/F 072—EP-Offenlegungsschrift 738 712, NZ 286 380)
ai) indenoylguanidines of the formula I

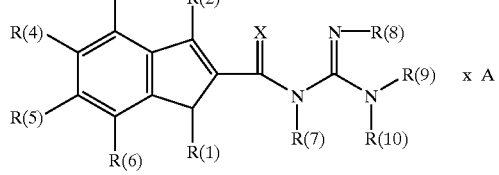

in which:
R(1) and R(2) independently of one another are hydrogen, alkyl having 1, 2, 3, 4, 5, 6, 7, 8, 9 or 10 carbon atoms, cycloalkyl having 3, 4, 5 or 6 carbon atoms, O-alkyl having 1, 2, 3 or 4 carbon atoms, O—C(=O)-alkyl having 1, 2, 3 or 4 carbon atoms or $C_mH_{2m}$—NR(12)R(13);
R(12) and R(13) independently of one another are hydrogen or alkyl having 1, 2, 3 or 4 carbon atoms;
m is zero, 1, 2, 3 or 4;
NH-C(=O)—$NH_2$, C(=O)—O-alkyl having 1, 2, 3 or 4 carbon atoms, C(=O)—$NH_2$, C(=O)NH-alkyl having 1, 2, 3 or 4 carbon atoms, C(=O)—N(alkyl)$_2$ having 1, 2, 3 or 4 carbon atoms in each alkyl group, alkenyl having 2, 3, 4, 5, 6, 7, 8, 9 or 10 carbon atoms, alkynyl having 2, 3, 4, 5, 6, 7, 8, 9 or 10 carbon atoms, alkylaryl having 1, 2, 3 or 4 carbon atoms in the alkyl group, alkenylaryl having 2, 3, 4, 5, 6, 7, 8, 9 or 10 carbon atoms in the alkenyl group, alkynylaryl having 2, 3, 4, 5, 6, 7, 8, 9 or 10 carbon atoms in the alkynyl group, $C_1$–$C_4$-alkyl-substituted aryl, $C_1$–$C_4$-alkylheteroaryl, $C_1$–$C_4$-alkenylheteroaryl, aminoalkylaryl having 1, 2, 3 or 4 carbon atoms in the alkyl group, substituted aryl, heteroaryl and substituted heteroaryl;
R(3), R(4), R(5) and R(6) independently of one another are hydrogen, alkyl having 1, 2, 3, 4, 5, 6, 7, 8, 9 or 10 carbon atoms, O-alkyl having 1, 2, 3, 4, 5, 6, 7, 8, 9 or 10 carbon atoms, halogen, (such as F, Cl, Br, I), OH, aryl, substituted aryl, heteroaryl, substituted heteroaryl, O-lower alkyl, O-aryl, O-lower alkylaryl, O-substituted aryl, O-lower alkyl-substituted aryl, O—C(=O)—$C_1$–$C_4$-alkylaryl, O—C(=O)—NH—$C_1$–$C_4$-alkyl, O—C(=O)—N($C_1$–$C_4$-alkyl)$_2$, $NO_2$, CN, $CF_3$, $NH_2$, NH—C(=O)—$C_1$–$C_4$-alkyl, NH—C(=O)—$NH_2$, COOH, C(=O)—O—$C_1$–$C_4$-alkyl, C(=O)—$NH_2$, C(=O)—NH—$C_1$–$C_4$-alkyl, C(=O)—N($C_1$–$C_4$-alkyl)$_2$, $C_1$–$C_4$-COOH, $C_1$–$C_4$-alkyl-C(=O)—O—$C_1$–$C_4$-alkyl, $SO_3H$, $SO_2$-alkyl, $SO_2$-alkylaryl, $SO_2$—N—(alkyl)$_2$, $SO_2$—N(alkyl)(alkylaryl), C(=O)—R(11), $C_1$–$C_{10}$-alkyl-C(=O)—R(11), $C_2$–$C_{10}$-alkenyl-C(=O)—R(11), $C_2$–$C_{10}$-alkynyl-C(=O)—R(11), NH—C(=O)—$C_1$–$C_{10}$-alkyl-C(=O)—R(11), O—$C_1$–$C_{11}$-alkyl-C(=O)—R(11);
R(11) is $C_1$–$C_4$-alkyl, $C_1$–$C_4$-alkynyl, aryl, substituted aryl, $NH_2$, NH—$C_1$–$C_4$-alkyl, N—($C_1$–$C_4$-alkyl)$_2$, $SO_3H$, $SO_2$-alkyl, $SO_2$-alkylaryl, $SO_2$—N-(alkyl)$_2$, $SO_2$—N(alkyl)(alkylaryl);
X is O, S or NH;
R(7), R(8), R(9) and R(10) independently of one another are hydrogen, alkyl, cycloalkyl, aryl, alkylaryl; or R(8) and R(9) together are part of a 5, 6 or 7-membered heterocyclic ring;

A is absent or is a nontoxic organic or inorganic acid.
(HOE 951F 109—EP 748 795, NZ 286 583)

ak) benzyloxycarbonylguanidines of the formula I

I in which:
R(1), R(2) and R(3) independently of one another are
—Y—[4—R(8)-phenyl], —Y—[3—R(8)-phenyl] or —Y—[2—R(8)-phenyl],
where the phenyl is in each case unsubstituted or substituted by 1–2 substituents from the group consisting of F, Cl, —CF$_3$, methyl, hydroxyl, methoxy and —NR(96)R(97);
R(96) and R(97) independently of one another are hydrogen or —CH$_3$;
Y is a bond, CH$_2$, oxygen, —S— or —NR(9);
R(9) is hydrogen or alkyl having 1, 2, 3 or 4 carbon atoms;
R(8) is SO$_a$[NR(98)]$_b$NR(99)R(10);
a is 1 or 2;
b is 0 or 1;
a+b=2;
R(98), R(99) and R(10) independently of one another are hydrogen, —(C$_1$–C$_8$)-alkyl, benzyl, —(C$_2$–C$_8$)-alkylene-NR(11)R(12), (C$_2$–C$_8$)-alkylene-NR(13)—(C$_2$–C$_8$)-alkylene-NR(37)R(38) or (C$_0$–C$_8$)-alkylene-CR(39)R(40)CR(41)R(42)(C$_0$–C$_8$)-alkylene-NR(43)R(44);
R(11), R(12), R(13), R(37), R(38), R(43) and R(44) independently of one another are hydrogen, —(C$_1$–C$_8$)-alkyl or benzyl:
R(39), R(40), R(41) and R(42) independently of one another are hydrogen, —(C$_1$–C$_8$)-alkyl or —(C$_0$–C$_3$)-alkylenephenyl,
where the phenyl is not substituted or is substituted by 1–3 substituents selected from the group consisting of F, Cl, —CF$_3$, methyl and methoxy; or
R(99) and R(10) together are 4–6 methylene groups, of which one CH$_2$ group can be replaced by oxygen, —S—, —NH—, —N—CH$_3$ or —N-benzyl; or
R(8) is SO$_a$[NR(98)]$_b$NR(95)—C[=N—R(94)]—NR(93)R(92);
R(92), R(93), R(94) and R(95) independently of one another are hydrogen or alkyl having 1, 2, 3 or 4 carbon atoms; or
R(1), R(2) and R(3) independently of one another are pyrrol-1-yl, pyrrol-2-yl or pyrrol-3-yl,
which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl, methoxy; or
R(1), R(2) and R(3) independently of one another are hydrogen, —(C$_1$–C$_8$)-alkyl, —(C$_2$–C$_8$)-alkenyl or —(CH$_2$)$_m$R(14);

m is zero, 1 or 2;
R(14) is —(C$_3$–C$_8$)-cycloalkyl or phenyl,
which is not substituted or is substituted by 1–3 substituents selected from the group consisting of F and —Cl, —CF$_3$, methyl, methoxy and —NR(15)R(16);
R(15) and R(16) are hydrogen or —CH$_3$; or
R(1), R(2) and R(3) independently of one another are —Q4[(CH$_2$)$_k$—CHR(17)—(C=O)R(20)]-phenyl, —Q-3-(CH$_2$)$_k$—CHR(17)—(C=O)R(20)]-phenyl or —Q-2—[(CH$_2$)$_k$—CHR(17)—(C=O)R(20)]-phenyl,
where the phenyl in each case is unsubstituted or substituted by 1–2 substituents from the group F, Cl, —CF$_3$, methyl, hydroxyl, methoxy and —NR(35)R(36);
R(35) and R(36) independently of one another are hydrogen or —CH$_3$;
Q is a bond, oxygen, —S— or —NR(18);
R(18) is hydrogen or —(C$_1$–C$_4$)-alkyl;
R(17) is —OR(21) or —NR(21)R(22);
R(21) and R(22) independently of one another are hydrogen, —(C$_1$–C$_8$)-alkyl, —(C$_1$–C$_8$)-alkanoyl, —(C$_1$–C$_8$,alkoxycarbonyl, benzyl, benzyloxycarbonyl; or
R(21) is trityl;
R(20) is —OR(23) or —NR(23)R(24);
R(23), R(24) independently of one another are hydrogen, —(C$_1$–C$_8$)-alkyl or benzyl;
k is zero, 1, 2, 3 or 4; or
R(1), R(2) and R(3) independently of one another are (C$_1$–C$_9$)-heteroaryl, which is linked via C or N and which is unsubstituted or substituted by 1–3 substituents from the group F, Cl, CF$_3$, CH$_3$, methoxy, hydroxyl, amino, methylamino and dimethylamino; or
R(1), R(2) and R(3) are —SR(25), —OR(25), —NR(25)R(26), —CR(25)R(26)R(27);
R(25) is —C$_f$H$_{2f}$(C$_1$–C$_9$)-heteroaryl,
which is unsubstituted or is substituted by 1–3 substituents from the group F, Cl, CF$_3$, CH$_3$, methoxy, hydroxyl, amino, methylamino and dimethylamino;
f is zero, 1 or 2;
R(26) and R(27) independently of one another are defined as R(25) or are hydrogen or (C$_1$–C$_4$)-alkyl, or
R(1), R(2) and R(3) independently of one another are (C$_1$–C$_9$)-heteroaryl-N-oxide,
which is linked via C or N and which is unsubstituted or substituted by 1–3 substituents selected from the group consisting of F, Cl, CF$_3$, CH$_3$, methoxy, hydroxyl, amino, methylamino and dimethylamino; or
R(1), R(2) and R(3) independently of one another are —SR(28), —OR(28), —NR(28)R(29) or —CR(28)R(29)R(30);
R(28) is —C$_g$H$_{2g}$—(C$_1$–C$_9$)-heteroaryl-N-oxide,
which is unsubstituted or is substituted by 1–3 substituents selected from the group consisting of F, Cl, CF$_3$, CH$_3$, methoxy, hydroxyl, amino, methylamino and dimethylamino;
g is zero, 1 or 2;
R(29), R(30) independently of one another are defined as R(28), hydrogen or (C$_1$–C$_4$)-alkyl; or
R(1), R(2) and R(3) independently of one another are hydrogen, F, Cl, Br, I, —C≡N, T—(CH$_2$)$_h$—(C$_i$F$_{2i+1}$), R(31)SO$_j$—, R(32)R(33)N—CO—, R(34)—CO— or R(45)R(46)N—SO$_2$, where the perfluoroalkyl group is straight-chain or branched;

T is a bond, oxygen, —S— or —NR(47);

l is zero, 1 or 2;

h is zero, 1 or 2;

i is 1, 2, 3, 4, 5 or 6;

R(31), R(32), R(34) and R(45) independently of one another are —($C_1$–$C_8$)-alkyl, —($C_3$–$C_6$)-alkenyl, $(CH_2)_n$R(48) or —$CF_3$;

n is zero, 1, 2, 3 or 4;

R(47) is hydrogen or alkyl with 1, 2 or 3 carbon atoms;

R(48) is —($C_3$–$C_7$)-cycloalkyl or phenyl, which is not substituted or is substituted by 1–3 substituents selected from the group consisting of F, Cl, —$CF_3$, methyl, methoxy and —NR(49)R(50);

R(49) and R(50) are hydrogen or alkyl having 1, 2, 3 or 4 carbon atoms; or

R(32), R(34) and R(45) are hydrogen;

R(33) and R(46) independently of one another are hydrogen or alkyl having 1, 2, 3 or 4 carbon atoms; or R(32) and R(33), and R(45) and R(46) together are 5 or 6 methylene groups, of which one $CH_2$ group can be replaced by oxygen, —S—, —NH—, —$NCH_3$ or —N-benzyl; or R(1), R(2) and R(3) independently of one another are R(51)—A—G—D—;

R(51) is a basic protonatable radical, i.e. an amino group —NR(52)R(53), an amidino group R(52)R(53)N—C[=N—R(54)] or a guanidino group R(52)R(53)N—C[=N—R(54)]—NR(55)—;

R(52), R(53), R(54) and R(55) independently of one another are hydrogen or alkyl having 1, 2, 3 or 4 carbon atoms; or R(52) and R(53) are a group $C_\alpha H_{2\alpha}$;

α is 4, 5, 6 or 7;

where if α=5, 6 or 7 a carbon atom of the group $C_\alpha H_{2\alpha}$ can be replaced by a heteroatom group O, $SO_d$ or NR(56), or R(53) and R(54) or R(54) and R(55) or R(52) and R(55) are a group $C_y H_{2y}$;

y is 2, 3, 4 or 5;

where if y=3, 4 or 5 a carbon atom of the group $C_y H_{2y}$ can be replaced by a heteroatom group O, $SO_d$ or NR(56);

d is zero, 1 or 2;

R(56) is hydrogen or methyl; or

R(51) is a basic heteroaromatic ring system having 1–9 carbon atoms;

A is a group $C_e H_{2e}$;

e is zero, 1, 2, 3, 4, 5, 6, 7, 8, 9 or 10;

where in the group $C_e H_{2e}$ a carbon atom can be replaced by one of the groupings —O—, —CO—, —CH[OR(57)]—, —$SO_r$—, —NR(57)—, —NR(57)—CO—, —NR(57)—CO—NH—, —NR(57)—CO—NH—$OS_2$— or —NR(57)—$SO_2$—;

r is zero, 1 or 2;

G is a phenylene radical

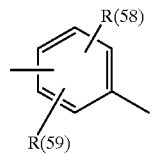

R(58) and R(59) independently of one another are hydrogen, methyl, methoxy, F, Cl, Br, I, $CF_3$ or —$SO_s$—R(60);

R(60) is methyl or NR(61)R(62);

R(61) and R(62) independently of one another are hydrogen or alkyl having 1, 2, 3 or 4 carbon atoms;

D is —$C_v H_{2v}$—$E_w$—;

v is zero, 1, 2, 3 or 4;

E is —O—, —CO—, —CH[OR(63)]—, —$SO_{aa}$— or —NR(63)—;

w is zero or 1;

aa is zero, 1 or 2

R(63) is hydrogen or methyl, or

R(1), R(2) and R(3) independently of one another are —$CF_2$R(64), —CF[R(65)][R(66)], —CF[$(CF_2)_q$—$CF_3$][R(65)], —C[$(CF_2)_p$—$CF_3$]=CR(65)R(66);

R(64) is alkyl having 1, 2, 3 or 4 carbon atoms or cycloalkyl having 3, 4, 5, 6 or 7 carbon atoms;

R(65) and R(66) independently of one another are hydrogen or alkyl having 1, 2, 3 or 4 carbon atoms;

q is zero, 1 or 2;

p is zero, 1 or 2; or

R(1), R(2) and R(3) independently of one another are —OR(67) or —NR(67)R(68);

R(67) and R(68) independently of one another are hydrogen or alkyl having 1, 2, 3, 4, 5 or 6 carbon atoms; or R(67) and R(68) together are 4, 5, 6 or 7 methylene groups, of which one $CH_2$ group can be replaced by oxygen, —S—, $SO_2$, —NH—, —$NCH_3$ or —N-benzyl;

R(4) and R(5) independently of one another are hydrogen, alkyl having 1, 2, 3 or 4 carbon atoms, F, Cl, —OR(69), —NR(70)R(71) or —$C_z F_{2z+1}$;

R(69), R(70) and R(71) independently of one another are hydrogen or alkyl having 1, 2 or 3 carbon atoms;

z is 1, 2, 3 or 4;

R(6) and R(7) independently of one another are hydrogen or alkyl having 1, 2, 3 or 4 carbon atoms;

X is oxygen or NR(72);

R(72) is hydrogen or alkyl having 1, 2, 3 or 4 carbon atoms;

and their pharmaceutically tolerable salts;

(HOE 95/F 115—EP 744 397, NZ 286 622)

al) alkenylcarboxylic acid guanidides, carrying fluorophenyl groups, of the formula I

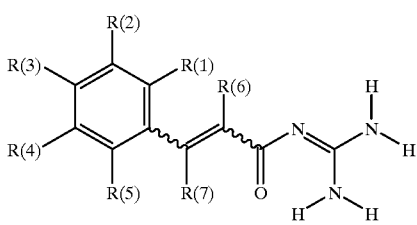

in which:
R(6) is hydrogen, $(C_1-C_8)$-alkyl, $(C_3-C_8)$-cycloalkyl or phenyl,
where the phenyl group is not substituted or is substituted by 1–3 substituents selected from the group consisting of F, Cl, $CF_3$, methyl, methoxy and NR(9)R(10);
R(9) and R(10) are hydrogen, $(C_1-C_4)$-alkyl or $(C_1-C_4)$-perfluoroalkyl;
R(7) independently is defined as R(6);
R(1), R(2), R(3), R(4) and R(5) independently of one another are hydrogen or F;
where, however, at least one of the radicals R(1), R(2), R(3), R(4) and R(5) must be fluorine;
and their pharmaceutically tolerable salts;
(HOE 95/F 167—NZ 299 015)
am) benzoylguanidines of the formula I

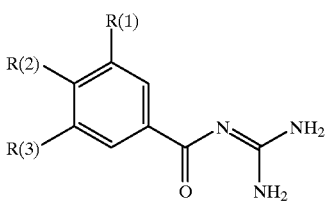

in which:
R(1) is R(4)—$SO_m$ or R(5)R(6)N—$SO_2$—;
m is 1 or 2;
R(4) and R(5) independently of one another are alkyl having 1, 2, 3, 4, 5, 6, 7 or 8 carbon atoms, alkenyl having 3, 4, 5 or 6 carbon atoms, $CF_3$ or —$C_nH_{2n}$—R(7);
n is zero, 1, 2, 3 or 4;
R(6) is H or alkyl having 1, 2, 3 or 4 carbon atoms;
R(7) is cycloalkyl having 3, 4, 5, 6, 7 or 8 carbon atoms or phenyl,
which is not substituted or is substituted by 1–3 substituents selected from the group consisting of F, Cl, $CF_3$, methyl, methoxy and NR(8)R(9);
R(8) and R(9) are H or alkyl having 1, 2, 3 or 4 carbon atoms; or
R(5) is also hydrogen; or
R(5) and R(6) together are 4 or 5 methylene groups, of which a $CH_2$ group can be replaced by oxygen, S, NH, N—$CH_3$ or N-benzyl; or
R(1) is —$O_p$—$(CH_2)_q$—$(CF_2)_r$—$CF_3$;
p is zero or 1;
q is zero, 1 or 2;
r is zero, 1, 2 or 3; or
R(1) is —SR(10), —OR(10) or —CR(10)R(11)R(12);
R(10), R(11) and R(12) independently of one another are hydrogen, alkyl having 1, 2, 3, 4, 5, 6, 7 or 8 carbon atoms, —$C_sH_{2s}$—$(C_3-C_8)$-cycloalkyl or an aromatic system selected from the group consisting of pyridyl, pyrrolyl, quinolyl, isoquinolyl, imidazolyl or phenyl;
s is zero, 1 or 2;
where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;
R(2) is —$(CH_2)_u$—$(CF_2)_t$—$CF_3$;
t is zero, 1, 2 or 3;
u is zero or 1;
R(3) is hydrogen or independently is defined as R(1);
and their pharmaceutically tolerable salts;
(HOE 95/F 173—NZ 299 052)
an) substituted cinnamic acid guanidides of the formula I

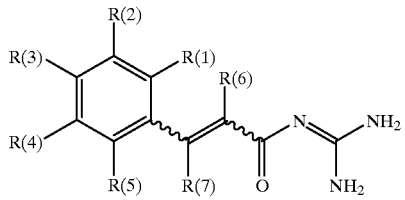

in which:
at least one of the substituents R(1), R(2), R(3), R(4) and R(5) is —$X_a$—$Y_b$—$L_n$—U;
X is CR(16)R(17), O, S or NR(18);
R(16), R(17) and R(18) independently of one another are H, alkyl having 1, 2, 3 or 4 carbon atoms or perfluoroalkyl having 1, 2, 3 or 4 carbon atoms;
a is zero or 1;
Y is alkylene having 1, 2, 3, 4, 5, 6, 7 or 8 carbon atoms, alkylene-T having 1, 2, 3, 4, 5, 6, 7 or 8 carbon atoms in the alkylene group, T, T-alkylene having 1, 2, 3, 4, 5, 6, 7 or 8 carbon atoms in the alkylene group;
T is NR(20), O, S or phenylene,
where the phenylene is not substituted or is substituted by 1–3 substituents selected from the group consisting of F, Cl, $CF_3$, methyl, methoxy and NR(21)R(22);
R(20), R(21) and R(22) independently of one another are H, alkyl having 1, 2, 3 or 4 carbon atoms or perfluoroalkyl having 1, 2, 3 or 4 carbon atoms;
b is zero or 1;
L is O, S, NR(23) or $C_kH_{2k}$;
k is 1, 2, 3, 4, 5, 6, 7, 8;
n is zero or 1;
U is NR(24)R(25) or an N-containing heterocycle having 1, 2, 3, 4, 5, 6, 7, 8 or 9 carbon atoms;
R(24) and R(25) independently of one another are hydrogen, alkyl having 1, 2, 3, 4, 5, 6, 7 or 8 carbon atoms or perfluoroalkyl having 1, 2, 3, 4, 5, 6, 7 or 8 carbon atoms; or
R(24) and R(25) together are 4 or 5 methylene groups, of which one $CH_2$ group can be replaced by oxygen, S, NH, N—$CH_3$ or N-benzyl;
where the N-containing heterocycles are N— or C-bridged and are not substituted or are substituted by 1–3 substituents selected from the group consisting of F, Cl, $CF_3$, methyl, methoxy and NR(27)R(28);

R(23), R(27) and R(28) independently of one another are H, alkyl having 1, 2, 3 or 4 carbon atoms or perfluoroalkyl having 1, 2, 3 or 4 carbon atoms;

and the other substituents R(1), R(2), R(3), R(4) and R(5) in each case independently of one another are H, F, Cl, Br, I, CN, $-O_n-C_mH_{2m+1}$, $-O_p-(CH_2)_s-C_qF_{2q+1}$ or $-C_rH_{2r}R(10)$;

n is zero or 1;
m is zero 1, 2, 3, 4, 5, 6, 7 or 8;
p is zero or 1;
q is 1, 2, 3, 4, 5, 6, 7 or 8;
s is zero, 1, 2, 3 or 4;
r is zero, 1, 2, 3 or 4;
R(10) is cycloalkyl having 3, 4, 5, 6, 7 or 8 carbon atoms, or phenyl,
where the phenyl is not substituted or is substituted by 1–3 substituents selected from the group consisting of F, Cl, $CF_3$, methyl, methoxy and NR(11)R(12);
R(11) and R(12) independently of one another are H, alkyl having 1, 2, 3 or 4 carbon atoms or perfluoroalkyl having 1, 2, 3 or 4 carbon atoms;

R(6) and R(7) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
which is not substituted or is substituted by 1–3 substituents selected from the group consisting of F, Cl, $CF_3$, methyl, methoxy and NR(14)R(15);
R(14) and R(15) independently of one another are H, alkyl having 1, 2, 3 or 4 carbon atoms or perfluoroalkyl having 1, 2, 3 or 4 carbon atoms;

and their pharmaceutically tolerable salts;
(HOE 95/F 220—NZ 299 052)

ao) benzoylguanidines of the formula I

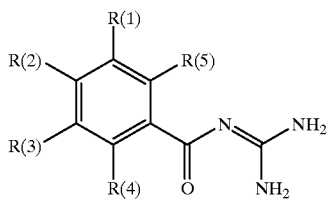

in which:
at least one of the substituents R(1), R(2) and R(3) is $R(6)-C(OH)_2-$;
R(6) is perfluoroalkyl having 1, 2 or 3 carbon atoms, which is straight-chain or branched;
and the other substituents R(1), R(2) and R(3) independently of one another are hydrogen, OH, F, Cl, Br, I, alkyl having 1, 2, 3, 4, 5 or 6 carbon atoms, cycloalkyl with 3, 4, 5 or 6 carbon atoms, alkoxy having 1, 2, 3 or 4 carbon atoms or phenoxy,
which is unsubstituted or is substituted by 1–3 substituents selected from the group consisting of F, Cl, methyl and methoxy; or
the other substituents R(1), R(2) and R(3) independently of one another are alkyl-$SO_x$, $-CR(7)=CR(8)R(9)$ or $-C\equiv CR(9)$;
x is zero, 1 or 2;
R(7) is hydrogen or methyl;
R(8) and R(9) independently of one another are hydrogen, alkyl having 1, 2, 3 or 4 carbon atoms, cycloalkyl having 3, 4, 5, 6, 7 or 8 carbon atoms or phenyl,
which is unsubstituted or is substituted by 1–3 substituents selected from the group consisting of F, Cl, $CF_3$, methyl and methoxy; or
the other substituents R(1), R(2) and R(3) independently of one another are phenyl, $C_6H_5-(C_1-C_4)$-alkyl, naphthyl, biphenylyl, quinolinyl, isoquinolinyl or imidazolyl,
where quinolinyl, isoquinolinyl or imidazolyl are bonded via C or N and where phenyl, $C_6H_5-(C_1-C_4)$-alkyl, naphthyl, biphenylyl, quinolinyl, isoquinolinyl and imidazolyl are unsubstituted or are substituted by 1–3 substituents selected from the group consisting of F, Cl, $CF_3$, $CH_3$, methoxy, hydroxyl, amino, methylamino and dimethylamino; or
the other substituents R(1), R(2) and R(3) independently of one another are SR(10), $-OR(10)$, $-CR(10)R(11)R(12)$;
R(10) is $-C_fH_{2f}-(C_3-C_8)$-cycloalkyl, quinolinyl, isoquinolinyl, pyridinyl, imidazolyl or phenyl,
where the aromatic systems quinolinyl, isoquinolinyl, pyridinyl, imidazolyl and phenyl are unsubstituted or are substituted by 1–3 substituents selected from the group consisting of F, Cl, $CF_3$, $CH_3$, methoxy, hydroxyl, amino, methylamino and dimethylamino;
f is zero, 1 or 2;
R(11) and R(12) independently of one another are defined as R(10), hydrogen or alkyl having 1, 2, 3 or 4 carbon atoms;
R(4) and R(5) independently of one another are hydrogen, alkyl having 1, 2 or 3 carbon atoms, F, Cl, Br, I, CN, OR(13), NR(14)R(15), $-(CH_2)_n-(CF_2)_o-CF_3$;
R(13), R(14) and R(15) independently of one another are hydrogen or alkyl having 1, 2, 3 or 4 carbon atoms;
n is zero or 1;
o is zero, 1 or 2;

and their pharmacologically acceptable salts;
(HOE 95/F 253—NZ 299 682)

ap) sulfonimidamides of the formula I

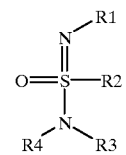

in which:
at least one of the three substituents R(1), R(2) and R(3) is a benzoylguanidine,

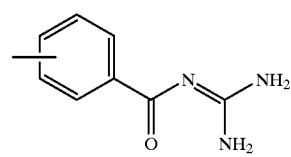

which is unsubstituted or substituted in the phenyl moiety by 1–4 radicals selected from the group consisting of alkyl having 1, 2, 3, 4, 5, 6, 7 or 8 carbon atoms, alkenyl having 2, 3, 4, 5, 6, 7 or 8 carbon atoms, —(CH$_2$)$_m$—R(14), F, Cl, Br, I, —C≡N, CF$_3$, R(22) SO$_2$—, R(23)R(24)N—CO—, R(25)—CO—, R(26)R (27)N—SO$_2$, —OR(35), —SR(35) or —NR(35)R(36); m is zero, 1 or 2;

R(14) is —(C$_3$–C$_8$)-cycloalkyl or phenyl,
which is not substituted or is substituted by 1–3 substituents selected from the group consisting of F and Cl, —CF$_3$, methyl, methoxy and —NR(15)R (16);

R(15) and R(16) independently of one another are hydrogen or —CH$_3$;

R(22), R(23), R(25) and R(26) independently of one another are alkyl having 1, 2, 3, 4, 5, 6, 7 or 8 carbon atoms, alkenyl having 2, 3, 4, 5, 6, 7 or 8 carbon atoms, (CH$_2$)$_n$R(29) or —CF$_3$;

n is zero, 1, 2, 3 or 4;
R(29) is —(C$_3$–C$_7$)-cycloalkyl or phenyl,
which is not substituted or is substituted by 1–3 substituents selected from the group consisting of F, Cl, —CF$_3$, methyl, methoxy and —NR(30)R (31);
R(30) and R(31) are hydrogen or alkyl having 1, 2, 3 or 4 carbon atoms; or R(23), R(25) and R(26) are hydrogen;

R(24) and R(27) independently of one another are hydrogen or alkyl having 1, 2, 3 or 4 carbon atoms; or R(23) and R(24), and also R(26) and R(27) together are 5 or 6 methylene groups, of which one CH$_2$ group can be replaced by oxygen, —S—, —NH—, —NCH$_3$ or —N-benzyl;

R(35) and R(36) independently of one another are hydrogen or alkyl having 1, 2, 3, 4, 5 or 6 carbon atoms; or R(35) and R(36) together are 4–7 methylene groups, of which one CH$_2$ group can be replaced by oxygen, —S—, —NH—, —NCH$_3$ or —N-benzyl; or R(35) is phenyl,
which is not substituted or is substituted by 1–3 substituents selected from the group consisting of F, Cl, —CF$_3$, methyl, methoxy, SO$_2$R(5), SO$_2$NR(6)R (7) and —NR(32)R(33);
R(5) is alkyl having 1, 2, 3, 4, 5 or 6 carbon atoms
R(6) and R(7) independently of one another are hydrogen or alkyl having 1, 2, 3 or 4 carbon atoms;
R(32) and R(33) independently of one another are hydrogen or alkyl having 1, 2, 3 or 4 carbon atoms; or
R(35) is C$_1$–C$_9$-heteroaryl,
which is unsubstituted or substituted by 1–3 substituents selected from the group consisting of F, Cl, CF$_3$, CH$_3$, methoxy, hydroxyl, amino, methylamino and dimethylamino;

and the other substituents R(1), R(2) and R(3) in each case independently of one another are alkyl having 1, 2, 3, 4, 5, 6, 7 or 8 carbon atoms, (CH$_2$)$_p$R(10)
p is zero, 1, 2, 3 or 4;
R(10) is phenyl,
which is not substituted or is substituted by 1–3 substituents selected from the group consisting of F, Cl, —CF$_3$, methyl, methoxy, —SO$_2$NR(17)R(8) and —SO$_2$R(9);
R(17) and R(8) independently of one another are hydrogen or alkyl having 1, 2, 3 or 4 carbon atoms;

R(9) is alkyl having 1, 2, 3 or 4 carbon atoms; or the other radicals R(1) and R(3) in each case are hydrogen, R(4) is hydrogen or alkyl having 1, 2, 3 or 4 carbon atoms;
and their pharmaceutically tolerable salts;
(HOE 95/F 265—NZ 299 739)

aq) benzoylguanidines of the formula I

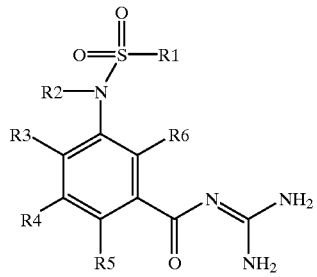

in which:
R(1) is alkyl having 1, 2, 3, 4, 5, 6, 7 or 8 carbon atoms or NR(7)R(8);
R(7) and R(8) independently of one another are hydrogen or alkyl having 1, 2, 3, 4, 5, 6, 7 or 8 carbon atoms;

R(2) is hydrogen, alkyl having 1, 2, 3, 4, 5, 6, 7 or 8 carbon atoms or —SO$_2$R(9);
R(9) independently is defined as R(1);

R(3) is hydrogen, —SR(25), —OR(25), —NR(25)R(26) or —CR(25)R(26)R(27);
R(25) is hydrogen, alkyl having 1, 2, 3, 4, 5, 6, 7 or 8 carbon atoms, or phenyl,
which is unsubstituted or substituted by 1–3 substituents selected from the group consisting of F, Cl, CF3, CH$_3$, methoxy, hydroxyl, amino, methylamino and dimethylamino; or
R(25) is —(C$_1$–C$_9$)-heteroaryl,
which is unsubstituted or substituted by 1–3 substituents selected from the group consisting of F, Cl, CF$_3$, CH$_3$, methoxy, hydroxyl, amino, methylamino and a dimethylamino;
R(26) and R(27) independently of one another are defined as R(25) or are hydrogen or alkyl having 1, 2, 3, 4, 5, 6, 7 or 8 carbon atoms;

R(4) is hydrogen, F, Cl, Br, I, OH, —C≡N, CF$_3$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);
m is zero, 1 or 2;
R(14) is —(C$_3$–C$_8$)-cycloalkyl or phenyl,
which is not substituted or is substituted by 1–3 substituents selected from the group consisting of F and Cl, —CF$_3$, methyl, methoxy and —NR(15)R (16);
R(15) and R(16) independently of one another are hydrogen or —CH$_3$;

R(5) and R(6) independently of one another are hydrogen, alkyl having 1, 2, 3 or 4 carbon atoms, F, Cl, —OR(32), —NR(33)R(34) or CF$_3$;
R(32), R(33) and R(34) independently of one another are hydrogen or alkyl having 1, 2, 3 or 4 carbon atoms;
and their pharmaceutically tolerable salts;

(HOE 95/F 269 K)
ar) benzenedicarboxylic acid diguanidides of the formula I

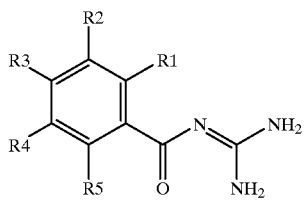

in which:
one of the radicals R(1), R(2), R(3) and R(4) is —CO—N=C(NH$_2$)$_2$;
and the other radicals R(1), R(2), R(3) and R(4) in each case are:
R(1) is hydrogen, alkyl having 1, 2, 3 or 4 carbon atoms, F, Cl, Br, I, —OR(32), —NR(33)R(34) or CF$_3$;
R(32), R(33) and R(34) independently of one another are hydrogen or alkyl having 1, 2, 3 or 4 carbon atoms;
R(2) and R(4) independently of one another are hydrogen, F, Cl, Br, I, OH, —CN, CF$_3$, —CO—N=C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);
m is zero, 1 or 2;
R(14) is —(C$_3$–C$_8$)-cycloalkyl or phenyl,
which is not substituted or is substituted by 1–3 substituents selected from the group consisting of F and Cl, —CF$_3$, methyl, methoxy and —NR(15)R(16);
R(15) and R(16) are hydrogen or —CH$_3$; or
R(2) and R(4) independently of one another are pyrrol-1-yl, pyrrol-2-yl or pyrrol-3-yl,
not which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl, methoxy; or
R(2) and R(4) independently of one another are R(22)—SO$_2$—, R(23)R(24)N—CO—, R(28)—CO— or R(29)R(30)N—SO$_2$—;
R(22) and R(28) independently of one another are methyl or —CF$_3$;
R(23), R(24), R(29) and R(30) independently of one another are hydrogen or methyl; or
R(2) and R(4) independently of one another are —OR(35) or —NR(35)R(36);
R(35) and R(36) independently of one another are hydrogen or alkyl having 1, 2, 3, 4, 5 or 6 carbon atoms; or
R(35) and R(36) together are 4–7 methylene groups, of which one CH$_2$ group can be replaced by oxygen, —S—, —NH—, —NCH$_3$ or —N-benzyl;
R(3) is hydrogen, —SR(25), —OR(25), —NR(25)R(26), —CR(25)R(26)R(27),
R(25) is hydrogen, alkyl having 1, 2, 3, 4, 5, 6, 7 or 8 carbon atoms or phenyl,
which is unsubstituted or substituted by 1–3 substituents selected from the group consisting of F, Cl, CF$_3$, CH$_3$, methoxy, hydroxyl, amino, methylamino and dimethylamino; or R(25) is —(C$_1$–C$_9$)-heteroaryl,
which is unsubstituted or substituted by 1–3 substituents selected from the group consisting of F, Cl, CF$_3$, CH$_3$, methoxy, hydroxyl, amino, methylamino and dimethylamino;
R(26) and R(27) independently of one another are defined as R(25) or are hydrogen or alkyl having 1, 2, 3, 4, 5, 6, 7 or 8 carbon atoms;
R(5) is alkyl having 1, 2, 3 or 4 carbon atoms, F, Cl, Br, I, X—(CH$_2$)$_y$—CF$_3$ or phenyl,
which is not substituted or is substituted by 1–3 substituents selected from the group consisting of F and Cl, —CF$_3$, methyl, methoxy and —NR(6)R(7);
R(6) and R(7) independently of one another are hydrogen or —CH$_3$;
X is a bond or oxygen;
y is zero, 1 or 2;
and their pharmaceutically tolerable salts;
(HOE 95/F 269 BK)
as) benzenedicarboxylic acid diguanidides of the formula I

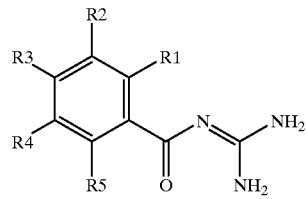

in which:
one of the radicals R(1), R(2), R(3) and R(5) is —CO—N=C(NH$_2$)$_2$;
and the other radicals R(1), R(2), R(3) and R(5) in each case are:
R(1) and R(5) independently of one another are hydrogen, alkyl having 1, 2, 3 or 4 carbon atoms, F, Cl, —OR(32), —NR(33)R(34) or CF$_3$;
R(32), R(33) and R(34) independently of one another are hydrogen or alkyl having 1, 2, 3 or 4 carbon atoms;
R(2) is hydrogen, F, Cl, Br, I, OH, —CN, CF$_3$, —CO—N=C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);
m is zero, 1 or 2;
R(14) is —(C$_3$–C$_8$)-cycloalkyl or phenyl,
which is not substituted or is substituted by 1–3 substituents selected from the group consisting of F and Cl, —CF$_3$, methyl, methoxy and —NR(15)R(16);
R(15) and R(16) independently of one another are hydrogen or —CH$_3$; or
R(2) is R(22)—SO$_2$—, R(23)R(24)N—CO—, R(28)—CO— or R(29)R(30)N—SO$_2$—;
R(22) and R(28) independently of one another are methyl or —CF$_3$;
R(23), R(24), R(29) and R(30) independently of one another are hydrogen or methyl; or
R(2) is —OR(35) or —NR(35)R(36);
R(35) and R(36) independently of one another are hydrogen or alkyl having 1, 2, 3, 4, 5 or 6 carbon atoms; or
R(35) and R(36) together are 4–7 methylene groups, of which one CH$_2$ group can be replaced by oxygen, —S—, —NH—, —NCH$_3$ or —N-benzyl;

R(3) is hydrogen, —SR(25), —OR(25), —NR(25)R(26), —CR(25)R(26)R(27);
R(25) is hydrogen, alkyl having 1, 2, 3, 4, 5, 6, 7 or 8 carbon atoms or phenyl,
which is unsubstituted or substituted by 1–3 substituents selected from the group consisting of F, Cl, $CF_3$, $CH_3$, methoxy, hydroxyl, amino, methylamino and dimethylamino; or
R(25) is —($C_1$–$C_9$)-heteroaryl,
which is unsubstituted or substituted by 1–3 substituents selected from the group consisting of F, Cl, $CF_3$, $CH_3$, methoxy, hydroxyl, amino, methylamino and dimethylamino;
R(26) and R(27) independently of one another are defined as R(25) or are hydrogen or alkyl having 1, 2, 3, 4, 5, 6, 7 or 8 carbon atoms;
R(4) is CF3, alkyl having 1, 2, 3, 4, 5, 6, 7 or 8 carbon atoms, alkenyl having 2, 3, 4, 5, 6, 7 or 8 carbon atoms, —($C_3$–$C_8$)-cycloalkyl or —$(CH_2)_m$R(14);
m is 1 or 2;
R(14) is —($C_3$–$C_8$)-cycloalkyl or phenyl,
which is not substituted or is substituted by 1–3 substituents selected from the group consisting of F and Cl, —$CF_3$, methyl, methoxy and —NR(15)R(16);
R(15) and R(16) independently of one another are hydrogen or —$CH_3$; or
R(4) is phenyl,
which is substituted by 2, 3, 4 or five substituents selected from the group consisting of F, Cl, $CF_3$, methyl, methoxy and —NR(15)R(16);
R(15) and R(16) independently of one another are hydrogen or $CH_3$;
and their pharmaceutically tolerable salts;
(HOE 96/F 013)
at) diaryldicarboxylic acid diguanidides of the formula I

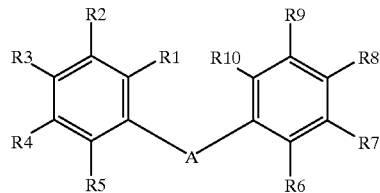

in which:
one of the radicals R(1), R(2), R(3), R(4) and R(5) is —CO—N=C($NH_2$)$_2$;
the other radicals R(1) and R(5) in each case independently of one another are hydrogen, alkyl having 1, 2, 3 or 4 carbon atoms, F, Cl, —OR(32), —NR(33)R(34) or $CF_3$;
R(32), R(33) and R(34) independently of one another are hydrogen or alkyl having 1, 2, 3 or 4 carbon atoms;
the other radicals R(2) and R(4) in each case independently of one another are hydrogen, F, Cl, Br, I, OH, —CN, $CF_3$, —CO—N=C($NH_2$)$_2$, alkyl having 1, 2, 3, 4, 5, 6, 7 or 8 carbon atoms, alkenyl having 2, 3, 4, 5, 6, 7 or 8 carbon atoms or —$(CH_2)_m$R(14);
m is zero, 1 or 2;
R(14) is —($C_3$–$C_8$)-cycloalkyl or phenyl,
which is not substituted or is substituted by 1–3 substituents selected from the group consisting of F and Cl, —$CF_3$, methyl, methoxy and —NR(15)R(16);
R(15) and R(16) are hydrogen or —$CH_3$; or
the other radicals R(2) and R(4) in each case independently of one another are pyrrol-1-yl, pyrrol-2-yl or pyrrol-3-yl,
which is not substituted or is substituted by 1–4 substituents selected from the group consisting of F, Cl, Br, I, —CN, ($C_2$–$C_8$)-alkanoyl, ($C_2$–$C_8$)alkoxycarbonyl, formyl, carboxyl, —$CF_3$, methyl, methoxy; or
the other radicals R(2) and R(4) in each case are R(22)—$SO_2$—, R(23)R(24)N—CO—, R(28)—CO— or R(29)R(30)N—$SO_2$;
R(22) and R(28) independently of one another are methyl or —$CF_3$;
R(23), R(24), R(29) and R(30) independently of one another are hydrogen or methyl; or
the other radicals R(2) and R(4) in each case independently of one another are —OR(35) or —NR(35)R(36);
R(35) and R(36) independently of one another are hydrogen or alkyl having 1, 2, 3, 4, 5 or 6 carbon atoms; or
R(35) and R(36) together are 4–7 methylene groups, of which one $CH_2$ group can be replaced by oxygen, —S—, —NH—, —$NCH_3$ or —N-benzyl;
the other radical R(3) in each case is hydrogen, —SR(25), —OR(25), —NR(25)R(26), —CR(25)R(26)R(27);
R(25) is hydrogen, alkyl having 1, 2, 3, 4, 5, 6, 7 or 8 carbon atoms or phenyl,
which is unsubstituted or substituted by 1–3 substituents selected from the group consisting of F, Cl, $CF_3$, $CH_3$, methoxy, hydroxyl, amino, methylamino and dimethylamino; or
R(25) is —($C_1$–$C_9$)-heteroaryl,
which is unsubstituted or substituted by 1–3 substituents selected from the group consisting of F, Cl, $CF_3$, $CH_3$, methoxy, hydroxyl, amino, methylamino and dimethylamino;
R(26) and R(27) independently of one another are defined as R(25) or are hydrogen or alkyl having 1, 2, 3, 4, 5, 6, 7 or 8 carbon atoms;
one of the radicals R(6), R(7), R(8), R(9) and R(10) is —CO—N=C($NH_2$)$_2$;
the other radicals R(6) and R(10) in each case independently of one another are hydrogen, alkyl having 1, 2, 3 or 4 carbon atoms, F, Cl, —OR(132), —NR(133)R(134) or $CF_3$;
R(132), R(133) and R(134) independently of one another are hydrogen or alkyl having 1, 2, 3 or 4 carbon atoms;
the other radicals R(7) and R(9) in each case independently of one another are hydrogen, F, Cl, Br, I, OH, —CN, $CF_3$, —CO—N=C($NH_2$)$_2$, alkyl having 1, 2, 3, 4, 5, 6, 7 or 8 carbon atoms, alkenyl having 2, 3, 4, 5, 6, 7 or 8 carbon atoms or —$(CH_2)_{mm}$R(114);
mm is zero, 1 or 2;
R(114) is —($C_3$–$C_8$)-cycloalkyl or phenyl,
which is not substituted or is substituted by 1–3 substituents selected from the group consisting of F and Cl, —$CF_3$, methyl, methoxy and —NR(115)R(116);
R(115) and R(116) are hydrogen or —$CH_3$; or
the other radicals R(7) and R(9) in each case independently of one another are pyrrol-1-yl, pyrrol-2-yl or pyrrol-3-yl,
which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl and methoxy; or the other radicals R(7) and R(9) in each case are R(122)—SO$_2$—, R(123)R(124)N—CO—, R(128)—CO— or R(129)R(130)N—SO$_2$;

R(122) and R(128) independently of one another are methyl or —CF$_3$;

R(123), R(124), R(129) and R(130) independently of one another are hydrogen or methyl; or the other radicals R(7) and R(9) in each case independently of one another are —OR(135) or —NR(135)R(136);

R(135) and R(136) independently of one another are hydrogen or alkyl having 1, 2, 3, 4, 5 or 6 carbon atoms; or R(135) and R(136) together are 4–7 methylene groups, of which one CH$_2$ group can be replaced by oxygen, —S—, —NH—, —NCH$_3$ or —N-benzyl;

the other radical R(8) in each case is hydrogen, —SR(125), —OR(125), —NR(125)R(126) or —CR(125)R(126)R(127);

R(125) is hydrogen, alkyl having 1, 2, 3, 4, 5, 6, 7 or 8 carbon atoms or phenyl,
which is unsubstituted or substituted by 1–3 substituents selected from the group consisting of F, Cl, CF$_3$, CH$_3$, methoxy, hydroxyl, amino, methylamino and dimethylamino; or R(125) is —(C$_1$–C$_9$)-heteroaryl,
which is unsubstituted or substituted by 1–3 substituents selected from the group consisting of F, Cl, CF$_3$, CH$_3$, methoxy, hydroxyl, amino, methylamino and dimethylamino;

R(126) and R(127) independently of one another are defined as R(125) or are hydrogen or alkyl having 1, 2, 3, 4, 5, 6, 7 or 8 carbon atoms;

A is absent or is —NR(11)—CO—, —NR(12)—CO—NR(13)—, —NR(17)—CO—NR(18)—SO$_2$—, —NR(19)—SO$_2$—, —SO$_2$—NR(19)—SO$_2$—, —SO$_2$—NR(19)—CO—, —O—CO—NR(19)—SO$_2$— or —CR(20)=CR(21)—;

R(11), R(12), R(13), R(17), R(18), R(19), R(20) and R(21) independently of one another are hydrogen or alkyl having 1, 2, 3, 4, 5, 6, 7 or 8 carbon atoms and their pharmaceutically tolerable salts;
(HOE 96/F 026)

au) substituted thiophenylalkenylcarboxylic acid guanidides of the formula I

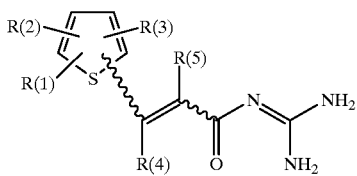

I in which:
at least one of the substituents R(1), R(2) and R(3) is —O$_p$—(CH$_2$)$_s$—C$_q$F$_{2q+1}$, R(40)CO— or R(31)SO$_k$—;
p is zero or 1;
s is zero, 1, 2 or 3 or 4;
q is 1, 2, 3, 4, 5, 6, 7 or 8;
k is zero, 1 or 2;
R(40) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
which is not substituted or is substituted by 1–3 substituents selected from the group consisting of F, Cl, CF$_3$, methyl and methoxy;

R(31) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
which is not substituted or is substituted by 1–3 substituents selected from the group consisting of F, Cl, CF$_3$, methyl or methoxy; or R(31) is NR(41)R(42);
R(41) and R(42) independently of one another are hydrogen, alkyl having 1, 2, 3 or 4 carbon atoms, perfluoroalkyl having 1, 2, 3 or 4 carbon atoms, or
R(41) and R(42) together are 4 or 5 methylene groups, of which one CH$_2$ group can be replaced by oxygen, S, NH, N—CH$_3$ or N-benzyl;

and the other substituents R(1), R(2) and R(3) in each case independently of one another are H, F, Cl, Br, I, CN, —O$_{na}$—C$_{ma}$H$_{2ma+1}$ or —O$_{ga}$C$_{ra}$H$_{2ra}$R(10);
na is zero or 1;
ma is zero, 1, 2, 3, 4, 5, 6, 7 or 8;
ga is zero or 1;
ra is zero, 1, 2, 3 or 4;
R(10) is cycloalkyl having 3, 4, 5, 6, 7 or 8 carbon atoms or phenyl,
where the phenyl is not substituted or is substituted by 1–3 substituents selected from the group consisting of F, Cl, CF$_3$, methyl and methoxy;

R(4) and R(5) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms or phenyl,
which is not substituted or is substituted by 1–3 substituents selected from the group consisting of F, Cl, CF$_3$, methyl, methoxy and NR(14)R(15);

R(14) and R(15) independently of one another are H, alkyl having 1, 2, 3 or 4 carbon atoms or perfluoroalkyl having 1, 2, 3 or 4 carbon atoms;

and their pharmaceutically tolerable salts;
(HOE 96/F 032)

av) ortho-substituted benzoylguanidines of the formula I

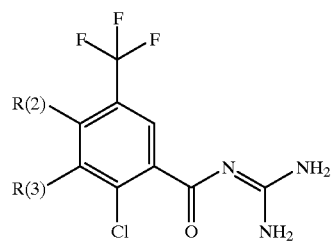

in which:
R(2) and R(3) independently of one another are hydrogen, Cl, Br, I, (C$_1$–C$_8$)-alkyl, (C$_3$–C$_8$)-cycloalkyl or —OR(5);
R(5) is (C$_1$–C$_8$)-alkyl or —C$_d$H$_2$d-(C$_3$–C$_8$)-cycloalkyl;
d is zero, 1 or 2;
where one of the two substituents R(2) and R(3) is always hydrogen but both substituents R(2) and R(3) are not simultaneously hydrogen,
and their pharmaceutically tolerable salts;

(HOE 96/F 042)
aw) benzoylguanidines of the formula I

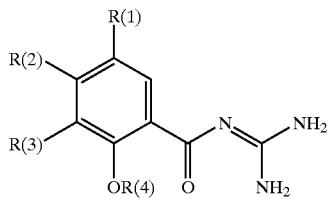

in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$;
X is oxygen, S, NR(5),
a is zero or 1;
b is zero, 1 or 2;
c is zero, 1, 2 or 3;
 R(5) is H, alkyl having 1, 2, 3 or 4 carbon atoms or —$C_dH_{2d}R(6)$;
 d is zero, 1, 2, 3 or 4;
 R(6) is cycloalkyl having 3, 4, 5, 6, 7 or 8 carbon atoms, phenyl, biphenylyl or naphthyl,
  where the aromatics phenyl, biphenylyl or naphthyl are not substituted or are substituted by 1–3 substituents selected from the group consisting of F, Cl, CF$_3$, methyl, methoxy and NR(7)R(8);
   R(7) and R(8) independently are H or alkyl having 1, 2, 3 or 4 carbon atoms; or
R(1) is —SR(10), —OR(10) or —CR(10)R(11)R(12);
 R(10) is —$C_fH_{2f}$-cycloalkyl having 3, 4, 5, 6, 7 or 8 carbon atoms in the cycloalkyl ring, or phenyl,
  where phenyl is unsubstituted or substituted by 1–3 substituents selected from the group consisting of F, Cl, CF$_3$, CH$_3$, methoxy, hydroxyl, amino, methylamino and dimethylamino;
 f is zero, 1 or 2;
 R(11) and R(12) independently of one another are defined as R(10) or are hydrogen or alkyl having 1, 2, 3 or 4 carbon atoms; or
R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring,
 which are in each case unsubstituted or substituted by 1–3 substituents selected from the group consisting of F, Cl, CF$_3$, CH$_3$, methoxy, hydroxyl, amino, methylamino and dimethylamino, or
R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$R(24),
 k is zero, 1, 2, 3 or 4;
 l is zero, 1, 2, 3 or 4;
 R(13) and R(14) identically or differently are —$(CH_2)_g$—$(CHOH)_h$—$(CH_2)_i$—$(CHOH)_j$—R(17) or —$(CH_2)_g$—O—$(CH_2$—$CH_2O)_h$—R(24);
  R(17) is hydrogen or methyl,
  g, h and i identically or differently are zero, 1, 2, 3 or 4;
  j is 1, 2, 3 or 4;
 R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;
 R(18) is phenyl,
  which is unsubstituted or substituted by 1–3 substituents selected from the group consisting of F, Cl, CF$_3$, methyl, methoxy and NR(25)R(26);
   R(25) and R(26) are H or alkyl having 1, 2, 3 or 4 carbon atoms; or
 R(18) is heteroaryl having 1, 2, 3, 4, 5, 6, 7, 8 or 9 carbon atoms,
  which is unsubstituted or substituted as phenyl; or
 R(18) is alkyl having 1, 2, 3, 4, 5 or 6 carbon atoms, which is unsubstituted or substituted by 1–3 OH; or
 R(18) is cycloalkyl having 3, 4, 5, 6, 7 or 8 carbon atoms;
 R(19), R(20), R(21), R(22) and R(23) identically or differently are hydrogen or methyl;
 R(24) is H, alkyl having 1, 2, 3, 4, 5 or 6 carbon atoms, cycloalkyl having 3, 4, 5, 6, 7 or 8 carbon atoms or —$C_mH_{2m}$—R(18);
  m is 1, 2, 3 or 4;
R(2) and R(3) are defined as R(1);
R(4) is alkyl having 1, 2, 3 or 4 carbon atoms;
and their pharmaceutically tolerable salts;
(HOE 96/F 043)
ax) ortho-substituted benzoylguanidines of the formula I

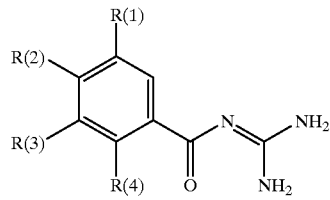

in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$:
X is oxygen, S, NR(5),
a is zero or 1;
b is zero, 1 or 2;
c is zero, 1, 2 or 3;
 R(5) is H, alkyl having 1, 2, 3 or 4 carbon atoms or —$C_dH_{2d}R(6)$;
 d is zero, 1, 2, 3 or 4;
 R(6) is cycloalkyl having 3, 4, 5, 6, 7 or 8 carbon atoms, phenyl, biphenylyl or naphthyl,
  where the aromatics phenyl, biphenylyl or naphthyl are unsubstituted or substituted by 1–3 substituents selected from the group consisting of F, Cl, CF$_3$, methyl, methoxy and NR(7)R(8);
   R(7) and R(8) independently are H or alkyl having 1, 2, 3 or 4 carbon atoms; or
R(1) is —SR(10), —OR(10) or —CR(10)R(11)R(12);
 R(10) is —$C_fH_{2f}$-cycloalkyl having 3, 4, 5, 6, 7 or 8 carbon atoms in the cycloalkyl ring, or phenyl,
  where phenyl is unsubstituted or substituted by 1–3 substituents selected from the group consisting of F, Cl, CF$_3$, CH$_3$, methoxy, hydroxyl, amino, methylamino and dimethylamino;
 f is zero, 1 or 2;
 R(11) and R(12) independently of one another are defined as R(10), or hydrogen or alkyl having 1, 2, 3 or 4 carbon atoms; or R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, $CF_3$, $CH_3$, methoxy, hydroxyl, amino, methylamino and dimethylamino, or R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$—R(24), k is zero, 1, 2, 3 or 4;

l is zero, 1, 2, 3 or 4;

R(13) and R(14) identically or differently are —(CH$_2$)$_g$—(CHOH)$_h$—(CH$_2$)$_i$—(CHOH)$_j$—R(17) or —(CH$_2$)$_g$—O—(CH$_2$—CH$_2$O)$_h$—R(24);

R(17) is hydrogen or methyl, g, h and i identically or differently are zero, 1, 2, 3 or 4;

j is 1, 2, 3 or 4;

R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;

R(18) is phenyl, which is unsubstituted or substituted by 1–3 substituents selected from the group consisting of F, Cl, $CF_3$, methyl, methoxy and NR(25)R(26);

R(25) and R(26) are H or alkyl having 1, 2, 3 or 4 carbon atoms; or

R(18) is heteroaryl having 1, 2, 3, 4, 5, 6, 7, 8 or 9 carbon atoms, which is unsubstituted or substituted as phenyl; or R(18) is alkyl having 1, 2, 3, 4, 5 or 6 carbon atoms, which is unsubstituted or substituted by 1–3 OH; or R(18) is cycloalkyl having 3, 4, 5, 6, 7 or 8 carbon atoms;

R(19), R(20), R(21), R(22) and R(23) identically or differently are hydrogen or methyl;

R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);

m is 1, 2, 3 or 4;

one of the two substituents R(2) and R(3) is hydroxyl; and the other of the substituents R(2) and R(3) in each case is defined as R(1);

R(4) is alkyl having 1, 2, 3 or 4 carbon atoms; alkoxy having 1, 2, 3 or 4 carbon atoms, F, Cl, Br, I or —(CH$_2$)$_n$—(CF$_2$)$_o$—CF$_3$;

n is zero or 1;

o is zero or 1;

and their pharmaceutically tolerable salts;

(HOE 96/F 135)

ay) bisortho-substituted benzoylguanidines of the formula I

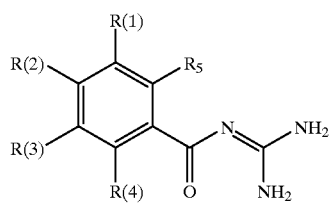

in which:

R(1), R(2) and R(3) independently of one another are R(10)—SO$_a$— or R(14)R(15)N—SO$_2$—;

a is zero, 1 or 2,

R(10), R(14) and R(15) independently of one another are alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5 or 6 carbon atoms or —C$_{ab}$H$_{2ab}$—R(16);

ab is zero, 1, 2, 3 or 4;

R(16) is cycloalkyl having 3, 4, 5, 6 or 7 carbon atoms or phenyl, which is unsubstituted or substituted by 1–3 substituents selected from the group consisting of F, Cl, $CF_3$, methyl, methoxy and NR(17)R(18);

R(17) and R(18) independently of each other are hydrogen, $CF_3$ or alkyl having 1, 2, 3 or 4 carbon atoms; or R(14) and R(15) together are 4 or 5 methylene groups, of which one CH$_2$ group can be replaced by oxygen, sulfur, NH, N—CH$_3$ or N-benzyl; or R(14) and R(15) are hydrogen; or R(1), R(2) and R(3) independently of each other are SR(21), —OR(22), —NR(23)R(24) or —CR(25)R(26)R(27);

R(21), R(22), R(23) and R(25) independently of one another are —C$_b$H$_{2b}$—(C$_1$–C$_9$)-heteroaryl, which is unsubstituted or substituted by 1–3 substituents selected from the group consisting of F, Cl, $CF_{31}$ $CH_{31}$ methoxy, hydroxyl, amino, methylamino and dimethylamino;

b is zero, 1 or 2;

R(24), R(26) and R(27) independently of each other are hydrogen, alkyl having 1, 2, 3 or 4 carbon atoms or perfluoroalkyl having 1, 2, 3 or 4 carbon atoms; or R(1), R(2) and R(3) independently of one another are hydrogen, F, Cl, Br, I, CN, —(Xa)$_{dg}$—C$_{da}$H$_{2da+1}$, —(Xb)$_{dh}$—(CH$_2$)$_{db}$—C$_{de}$F$_{2de+1}$, alkenyl having 3, 4, 5, 6, 7 or 8 carbon atoms or —C$_{df}$H$_{2df}$R(30);

(Xa) is oxygen, sulfur or NR(33);

R(33) is hydrogen, alkyl having 1, 2, 3 or 4 carbon atoms or perfluoroalkyl having 1, 2, 3 or 4 carbon atoms;

dg is zero or 1;

(Xb) is oxygen, sulfur or NR(34);

R(34) is hydrogen, alkyl having 1, 2, 3, or 4 carbon atoms or perfluoroalkyl having 1, 2, 3 or 4 carbon atoms;

dh is zero or 1;

da is zero, 1, 2, 3, 4, 5, 6, 7 or 8;

db is zero, 1, 2, 3 or 4;

de is zero, 1, 2, 3, 4, 5, 6 or 7;

df is zero, 1, 2, 3 or 4;

R(30) is cycloalkyl having 3, 4, 5, 6, 7 or 8 carbon atoms, phenyl, biphenylyl or naphthyl, where the aromatics phenyl, biphenylyl or naphthyl are not substituted or substituted by 1–3 substituents selected from the group consisting of F, Cl, $CF_3$, methyl, methoxy and NR(31)R(32);

R(31) and R(32) are hydrogen, alkyl having 1, 2, 3 or 4 carbon atoms or perfluoroalkyl having 1, 2, 3 or 4 carbon atoms; or R(1), R(2) and R(3) independently of one another are NR(40)R(41) or —(Xe)—$(CH_2)_{eb}$R(45);

R(40) and R(41) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms or $(CH_2)_e$—R(42);

e is zero, 1, 2, 3 or 4;

R(42) is cycloalkyl having 3, 4, 5, 6 or 7 carbon atoms or phenyl,
which is not substituted or substituted by 1–3 substituents selected from the group consisting of F, Cl, $CF_3$, methyl, methoxy and NR(43)R(44);

R(43) and R(44) independently of one another are hydrogen, $CF_3$ or alkyl having 1, 2, 3 or 4 carbon atoms; or R(40) and R(41) together are 4 or 5 methylene groups, of which one $CH_2$ group can be replaced by oxygen, sulfur, NH, N—$CH_3$ or N-benzyl;

(Xe) is oxygen, sulfur or NR(47);

R(47) is hydrogen, alkyl having 1, 2, 3 or 4 carbon atoms or perfluoroalkyl having 1, 2, 3 or 4 carbon atoms;

eb is zero, 1, 2, 3 or 4;

R(45) is cycloalkyl having 3, 4, 5, 6 or 7 carbon atoms or phenyl,
which is not substituted or substituted by 1–3 substituents selected from the group consisting of F, Cl, $CF_3$, methyl, methoxy, NR(50)R(51) and —(Xfa)—$(CH_2)_{ed}$—(Xfb)R(46);

Xfa is $CH_2$, oxygen, sulfur or NR(48);

Xfb is oxygen, sulfur or NR(49);

R(48), R(49), R(50) and R(51) independently of one another are hydrogen, alkyl having 1, 2, 3 or 4 carbon atoms or perfluoroalkyl having 1, 2, 3 or 4 carbon atoms;

ed is 1, 2, 3 or 4;

R(46) is hydrogen, alkyl having 1, 2, 3 or 4 carbon atoms or perfluoroalkyl having 1, 2, 3 or 4 carbon atoms; or R(1), R(2) and R(3) independently of one another are —CHR(52)R(53);

R(52) is $CH_2)_g$—$(CHOH)_h$—$(CH)_i$—$(CHOH)_k$—R(54) or —$(CH_2)_g$—O—$(CH_2$—$CH_2O)h$—R(54);

R(54) is hydrogen or methyl;

g, h, i are identical or different and are zero, 1, 2, 3 or 4;

k is 1, 2, 3 or 4;

R(53) is hydrogen or alkyl having 1, 2, 3 or 4 carbon atoms; or

R(1), R(2) and R(3) independently of one another are —C(OH)R(55)R(56);

R(55) and R(56) are identical or different and are hydrogen or alkyl having 1, 2, 3 or 4 carbon atoms; or R(55) and R(56) together are cycloalkyl having 3, 4, 5 or 6 carbon atoms; or R(55) is —$CH_2OH$; and R(4) and R(5) independently of one another are alkyl having 1, 2, 3 or 4 carbon atoms, alkoxy having 1, 2, 3 or 4 carbon atoms, OH, F, Cl, Br, I, CN, —$O_n$—$(CH_2)_o$—$(CF_2)_p$—$CF_3$;

n is zero or 1;

o is zero, 1 or 2;

p is zero, 1 or 2;

and their pharmaceutically tolerable salts;

(96/F 136)

az) substituted 1-naphthoylguanidines of the formula I

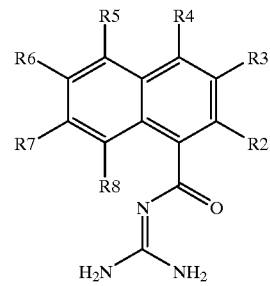

in which:

R2, R3, R4, R5, R6, R7 and R8 independently of one another are H, F, Cl, Br, I, CN, $NO_2$, $CF_3$, $C_2F_5$ or $X_aY_bZ$;

X is O, S, NR(10), CR(11)R(12), C=O, C(=O)NR(10), C(=O)O, SO, $SO_2$, $SO_2$NR(10), OC=O, NR(10)C=O or NR(10)$SO_2$,
where the linkage with the naphthalene ring is in each case effected through the atom on the left;

R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

a is zero or 1;

Y is alkylene having 1, 2, 3, 4, 5, 6, 7 or 8 $CH_2$ groups; it being possible for one of these $CH_2$ groups to be replaced by O, S, NR(13) or o-, p- or m-phenylene;

R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

b is zero or 1;

Z is H, alkyl having 1, 2, 3, 4, 5, 6 or 7 carbon atoms, cycloalkyl having 3, 4, 5, 6 or 7 carbon atoms, C(=O)R(15), $SO_2$R(15), NR(16)R(17) or phenyl, which is not substituted or substituted by 1–3 substituents selected from the group consisting of F, Cl, Br, $CF_3$, methyl, methoxy, NR(21)R(22);

R(21) and R(22) independently of one another are H or alkyl having 1, 2, 3 or 4 carbon atoms or perfluoroalkyl having 1, 2, 3 or 4 carbon atoms;

R(15) is N=$C(NH_2)_2$, NR(18)R(19), $N(CH_2)_c$ NR(18)R(19) or OR(20);

c is 2 or 3;

R(18) and R(19) independently of one another are H, alkyl having 1, 2, 3, 4, 5, 6, 7 or 8 carbon atoms or perfluoroalkyl having 1, 2, 3 or 4 carbon atoms; or R(18) and R(19) together are 4 or 5 methylene groups,
of which one $CH_2$ group can be replaced by oxygen, S, NH, N—$CH_3$, N-benzyl or N-(p-chlorophenyl);

R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

R(16) and R(17) independently of one another are H, alkyl having 1, 2, 3, 4, 5, 6, 7 or 8 carbon atoms or perfluoroalkyl having 1, 2, 3 or 4 carbon atoms; or R(16) and R(17) together are 4 or 5 methylene groups, of which one $CH_2$ group can be replaced by oxygen, S, NH, N—$CH_3$, N-benzyl or N-(p-chlorophenyl); or Z is a N-containing heterocycle having 1, 2, 3, 4, 5, 6, 7, 8 or 9 carbon atoms,
where the N-containing heterocycle is linked via N or C and is not substituted or substituted by 1–3 substituents selected from the group consisting of F, Cl, Br, $CF_3$, methyl, methoxy and NR(21)R(22);

but where in the case that R(4) is an alkoxy radical, at least one of the substituents R(2), R(3), R(5), R(6), R(7) and R(8) is not hydrogen;

and their pharmaceutically tolerable salts;
(HOE 96/F 137)

ba) substituted 2-naphthoylguanidines of the formula I

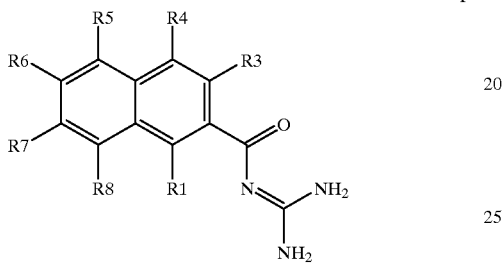

I in which:
at least one of the substituents R1, R3, R4, R5, R6, R7 and R8 is $XY_aWZ$ or $X'Y_aWZ'$;
X is O, S, NR(10) or CR(11)R(12);
R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
Y is alkylene having 1, 2, 3, 4, 5, 6, 7 or 8 $CH_2$ groups, where one of these $CH_2$ groups can be replaced by O, S, NR(13) or o-, p- or m-phenylene;
R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
a is zero or 1;
W is $CH_2$, $SO_2$, S(=O)(=NH) or—if W does not immediately follow a hetero atom of the group $XY_a$—also O or NR(14);
R(14) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
Z is C(=O)R(15), $SO_2$R(15) or—if W is not O or NR(14)—also NR(16)R(17);
R(15) is N=C(NH$_2$)$_2$, NR(18)R(19), N(CH$_2$)$_b$NR (18)R(19) or OR(20);
b is 2 or 3;
R(18) and R(19) independently of one another are H, alkyl having 1, 2, 3, 4, 5, 6, 7 or 8 carbon atoms or perfluoroalkyl having 1, 2, 3 or 4 carbon atoms; or
R(18) and R(19) together are 4 or 5 methylene groups,
of which one $CH_2$ group can be replaced by oxygen, S, NH, N—$CH_3$, N-benzyl or N-(p-chlorophenyl);
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
R(16) and R(17) independently of one another are H, alkyl having 1, 2, 3, 4, 5, 6, 7 or 8 carbon atoms or perfluoroalkyl having 1, 2, 3 or 4 carbon atoms; or
R(16) and R(17) together are 4 or 5 methylene groups, of which one $CH_2$ group can be replaced by oxygen, S, NH, N—$CH_3$, N-benzyl or N—(p-chlorophenyl);
X' is C=O, C(=O)NR(30), C(=O)O, SO, $SO_2$, $SO_2$NR (30), OC=O, NR(30) C=O or NR(30)$SO_2$,
where the linkage with the naphthalene ring is in each case effected through the atom on the left;
R(30) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
Z' is C(=O)R(15), $SO_2$R(15), an N-containing heterocycle having 1, 2, 3, 4, 5, 6, 7, 8 or 9 carbon atoms,
where the N-containing heterocycle is linked via N or C and is not substituted or substituted by 1–3 substituents selected from the group consisting of F, Cl, Br, $CF_3$, methyl, methoxy and NR(21)R(22);
R(21) and R(22) independently of one another are H, alkyl having 1, 2, 3 or 4 carbon atoms or perfluoroalkyl having 1, 2, 3 or 4 carbon atoms;
R(15) is N=C(NH$_2$)$_2$, NR(18)R(19), N(CH$_2$)$_b$NR(18) R(19) or OR(20);
R(18) and R(19) independently of one another are H, alkyl having 1, 2, 3, 4, 5, 6, 7 or 8 carbon atoms or perfluoroalkyl having 1, 2, 3 or 4 carbon atoms; or
R(18) and R(19) together are 4 or 5 methylene groups, of which one CH2 group can be replaced by oxygen, S, NH, N—$CH_3$, N-benzyl or N-(p-chlorophenyl);
b is 2 or 3;
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms; or
Z'—if W is not O or NR(14)—is NR(16)R(17);
R(16) and R(17) independently of one another are H, alkyl having 1, 2, 3, 4, 5, 6, 7 or 8 carbon atoms or perfluoroalkyl having 1, 2, 3 or 4 carbon atoms; or
R(16) and R(17) together are 4 or 5 methylene groups, of which one $CH_2$ group can be replaced by oxygen S, NH, N—$CH_3$, N-benzyl or N-(p-chlorophenyl);
and in each case the remaining substituents R1, R3, R4, R5, R6, R7 and R8, to which none of the abovementioned definitions has been assigned, independently of one another are H, F, Cl, Br, I, CN, $NO_2$, $CF_3$, $C_2F_5$ or $V_pQ_qU$;
V is O, S, SO, $SO_2$, NR(60), OC=O, C=O, C(=O) NR(60), C(=O)O or CR(66)R(67);
R(60), R(66) and R(67) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
p is zero or 1;
Q is alkylene having 1, 2, 3, 4, 5, 6, 7 or 8 $CH_2$ groups, where one of these $CH_2$ groups can be replaced by O, S, NR(68) or o-, p- or m-phenylene;
R(68) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

q is zero or 1;

U is H, alkyl having 1, 2, 3, 4, 5, 6 or 7 carbon atoms, cycloalkyl having 3, 4, 5, 6 or 7 carbon atoms, C(=O)R(65), SO$_2$R(65), NR(61)R(62) or phenyl, which is not substituted or substituted by 1–3 substituents selected from the group consisting of F, Cl, Br, CF$_3$, methyl, methoxy and NR(63)R(64);

R(63) and R(64) independently of one another are H, alkyl having 1, 2, 3 or 4 carbon atoms or perfluoroalkyl having 1, 2, 3 or 4 carbon atoms;

R(65) is N=C(NH$_2$)$_2$, NR(61)R(62) or OR(60);

R(61) and R(62) independently of one another are H, alkyl having 1, 2, 3, 4, 5, 6, 7 or 8 carbon atoms or perfluoroalkyl having 1, 2, 3 or 4 carbon atoms; or R(61) and R(62) together are 4 or 5 methylene groups, of which one CH$_2$ group can be replaced by oxygen, S, NH, N—CH$_3$, N-benzyl or N-(p-chlorophenyl); or U is an N-containing heterocycle having 1, 2, 3, 4, 5, 6, 7, 8 or 9 carbon atoms, where the N-containing heterocycle is linked via N or C and is not substituted or substituted by 1–3 substituents selected from the group consisting of F, Cl, Br, CF$_3$, methyl, methoxy and NR(63)R(64);

and at least one of the substituents R5, R6, R7 and R8 not being hydrogen;

and their pharmaceutically tolerable salts;

(HOE 96/F 141)

bb) ortho-substituted benzoylguanidines of the formula I in which:

R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF2)$_c$—CF$_3$;

X is oxygen, sulfur or NR(9), a is zero or 1;

b is zero, 1 or 2;

c is zero, 1, 2 or 3;

R(9) is H, alkyl having 1, 2, 3 or 4 carbon atoms or —C$_d$H$_{2d}$R(6);

d is zero, 1, 2, 3 or 4;

R(6) is cycloalkyl having 3, 4, 5, 6, 7 or 8 carbon atoms, phenyl, biphenylyl or naphthyl, where the aromatics phenyl, biphenylyl or naphthyl are not substituted or substituted by 1–3 substituents selected from the group consisting of F, Cl, CF$_3$, methyl, methoxy and NR(7)R(8);

R(7) and R(8) independently of one another are H or alkyl having 1, 2, 3 or 4 carbon atoms; or R(1) is —SR(10), —OR(10) or —CR(10)R(11)R(12);

R(10) is —C$_f$H$_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl, where heteroaryl and phenyl are unsubstituted or substituted by 1–3 substituents selected from the group consisting of F, Cl, CF$_3$, CH$_3$, methoxy, hydroxyl, amino, methylamino and dimethylamino;

f is zero, 1 or 2;

R(11) and R(12) independently of one another are as defined for R(10) or are hydrogen or alkyl having 1, 2, 3 or 4 carbon atoms; or R(1) is phenyl, naphthyl, biphenylyl or heteroaryl having 1, 2, 3, 4, 5, 6, 7, 8 or 9 carbon atoms, the latter being linked via a carbon or a nitrogen ring atom, each of the radicals being unsubstituted or substituted by 1–3 substituents selected from the group consisting of F, Cl, CF3, CH$_3$, methoxy, hydroxyl, amino, methylamino and dimethylamino, or R(1) is —SR(13), —OR(13), —NHR(13), —NR(13)R (14), —CHR(13)R(15), —C[R(15)R(16)]OH, —C≡CR(18), —C[R(19)]=CHR(18), —C[R(20)R (21)]$_k$—(CO)—[CR(22)R(23)]$_l$—R(24), k is zero, 1, 2, 3 or 4;

l is zero, 1, 2, 3 or 4;

R(13) and R(14) are identical or different and are —(CH$_2$)$_g$—(CHOH)$_h$—(CH$_2$)$_i$—(CHOH)$_{kk}$—R(17) or —(CH$_2$)$_g$—O—(CH$_2$—CH$_2$O)$_h$—R(24);

R(17) is hydrogen or methyl, g, h and i are identical or different and are zero, 1, 2, 3 or 4;

kk is 1, 2, 3 or 4;

R(15) and R(16) are identical or different and are hydrogen, alkyl having 1, 2, 3, 4, 5 or 6 carbon atoms, or together with the carbon atom carrying them are cycloalkyl having 3, 4, 5, 6, 7 or 8 carbon atoms;

R(18) is phenyl, which is unsubstituted or substituted by 1–3 substituents selected from the group consisting of F, Cl, CF$_3$, methyl, methoxy and NR(25)R(26);

R(25) and R(26) are H or alkyl having 1, 2, 3 or 4 carbon atoms; or

R(18) is heteroaryl having 1, 2, 3, 4, 5, 6, 7, 8 or 9 carbon atoms which is unsubstituted or substituted as for phenyl; or R(18) is alkyl having 1, 2, 3, 4, 5 or 6 carbon atoms, which is unsubstituted or substituted by 1–3 OH; or R(18) is cycloalkyl having 3, 4, 5, 6, 7 or 8 carbon atoms;

R(19), R(20), R(21), R(22) and R(23) are identical or different and are hydrogen or methyl;

R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);

m is 1, 2, 3 or 4;

one of the two substituents R(2) and R(3) is —O—CO—R(27);

R(27) is alkyl having 1, 2, 3, 4, 5, 6, 7 or 8 carbon atoms, cycloalkyl having 3, 4, 5, 6, 7 or 8 carbon atoms, phenyl, biphenylyl, naphthyl, pyridyl or quinolyl, where phenyl, biphenylyl, naphthyl, pyridyl or quinolyl are unsubstituted by 1–3 substituents selected from the group consisting of F, Cl, CF$_3$, methyl, methoxy and NR(7)R(8);

R(7) and R(8) independently of one another are hydrogen or alkyl having 1, 2, 3 or 4 carbon atoms;

one of the substituents R(2) and R(3) always being defined as R(1);

R(4) and R(5) independently of one another are hydrogen, alkyl having 1, 2, 3 or 4 carbon atoms;
  alkoxy having 1, 2, 3 or 4 carbon atoms, F, Cl, Br, I, CN or —(CH$_2$)$_n$—(CF$_2$)$_o$—CF$_3$;
    n is zero or 1;
    o is zero or 1;
and their pharmaceutically tolerable salts;
(96/F 154)
bc) benzoylguanidines of the formula I

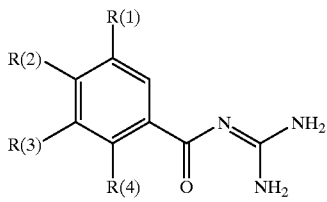

in which:
  R(1) is R(13)—SO$_m$ or R(14)R(15)N—SO$_2$—;
  m is 1 or 2;
    R(13) is alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —C$_n$H$_{2n}$—R(16),
    n is zero, 1, 2, 3 or 4;
      R(16) is cycloalkyl having 3, 4, 5, 6, 7 or 8 carbon atoms, phenyl, biphenylyl or naphthyl,
        where phenyl, biphenylyl and naphthyl are not substituted or substituted by 1–3 substituents selected from the group consisting of F, Cl, CF$_3$, methyl, methoxy and NR(25)R(26);
          R(25) and R(26) independently of one another are hydrogen, alkyl having 1, 2, 3 or 4 carbon atoms or perfluoroalkyl having 1, 2, 3 or 4 carbon atoms;
    R(14) is hydrogen, alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —C$_n$H$_{2n}$—R(27),
    n is zero, 1, 2, 3 or 4;
      R(27) is cycloalkyl having 3, 4, 5, 6, 7 or 8 carbon atoms, phenyl, biphenylyl or naphthyl,
        where phenyl, biphenylyl and naphthyl are not substituted or substituted by 1–3 substituents selected from the group consisting of F, Cl, CF$_3$, methyl, methoxy and NR(28)R(29);
          R(28) and R(29) independently of one another are hydrogen, alkyl having 1, 2, 3 or 4 carbon atoms or perfluoroalkyl having 1, 2, 3 or 4 carbon atoms;
    R(15) is hydrogen, alkyl having 1, 2, 3 or 4 carbon atoms or perfluoroalkyl having 1, 2, 3 or 4 carbon atoms; or
    R(14) and R(15) together are 4 or 5 methylene groups, of which one CH$_2$ group can be replaced by oxygen, S, NH, N—CH$_3$ or N-benzyl;
  one of the substituents R(2) and R(3) is hydrogen;
  and the other substituent R(2) and R(3) in each case is —CHR(30)R(31);
    R(30) is —(CH$_2$)$_g$—(CHOH)$_h$—(CH$_2$)$_i$—(CHOH)$_k$—R(32) or —(CH$_2$)$_g$—O—(CH$_2$—CH$_2$O)$_h$—R(24);
      R(24) and R(32) independently of one another are hydrogen or methyl;
      g, h, i are identical or different and are zero, 1, 2, 3 or 4;
      k is 1, 2, 3 or 4;
  or the other substituent R(2) and R(3) in each case is —C(OH)R(33)R(34);
    R(31), R(33) and R(34) are identical or different and are hydrogen or alkyl having 1, 2, 3 or 4 carbon atoms; or
    R(33) and R(34) together are cycloalkyl having 3, 4, 5 or 6 carbon atoms; or
    R(33) is —CH$_2$OH;
  R(4) is alkyl having 1, 2, 3 or 4 carbon atoms, alkoxy having 1, 2, 3 or 4 carbon atoms, F, Cl, Br, I, CN, —(CH$_2$)$_n$—(CF$_2$)$_o$—CF$_3$;
    n is zero or 1;
    o is zero, 1 or 2;
and their pharmaceutically tolerable salts;
(HOE 96/F 202)
bd) indanylideneacetylguanidines of formula I

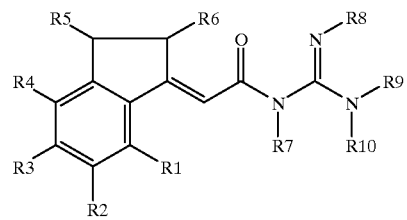

in which R1, R2, R3, R4, R5 and R6 independently of one another are H, C$_1$–C$_{10}$-alkyl; haloalkyl having 1–6 carbon atoms, O—C$_1$–C$_{10}$-alkyl, haloalkoxy having 1–6 carbon atoms, F, Cl, Br, I, aryl, substituted aryl, heteroaryl, substituted heteroaryl, OH, O-lower alkyl, O-aryl, O-lower alkylaryl, O-substituted aryl, O-lower alkyl-substituted aryl, O—C(=O)—C$_1$–C$_4$-alkylaryl, O—C(=O)—NH—C$_1$–C$_4$-alkyl, O—C(=O)—N(C$_1$–C$_4$-alkyl)$_2$, NO$_2$, CN, CF$_3$, NH$_2$, NH—C(=O)—C$_1$–C$_4$-alkyl, NH—C(=O)—NH$_2$, COOH, C(=O)—O—C$_1$–C$_4$-alkyl, C(=O)—NH$_2$, C(=O)—NH—C$_1$–C$_4$-alkyl, C(=O)—N(C$_1$–C$_4$-alkyl)$_2$, C$_1$–C$_4$—COOH, C$_1$–C$_4$-alkyl-C(=O)—O—C$_1$–C$_4$-alkyl, SO$_3$H, SO$_2$-alkyl, SO$_2$-alkylaryl, SO$_2$—N—(alkyl)$_2$, SO$_2$—N(alkyl)(alkylaryl), C(=O)—R11, C$_1$–C$_{10}$-alkyl-C—(=O)—R11, C$_2$–C$_{10}$-alkenyl-C(=O)—R11, C$_2$–C$_{10}$-alkynyl-C(=O)—R11, NH—C(=O)—C$_1$–C$_{10}$-alkyl-C(=O)—R11 or O—C$_1$–C$_{11}$-alkyl-C(=O)—R11;
  R11 is C$_1$–C$_4$-alkyl, C$_1$–C$_4$-alkynyl, aryl, substituted aryl, NH$_2$, NH—C$_1$–C$_4$-alkyl, N—(C$_1$–C$_4$-alkyl)$_2$, SO$_3$H, SO$_2$-alkyl, SO$_2$-alkylaryl, SO$_2$—N-(alkyl)$_2$ or SO$_2$—N(alkyl)(alkylaryl);
  X is O, S or NH;
    R7, R8, R9 and R10 independently of one another are H, alkyl, cycloalkyl, aryl, alkylaryl, or
    R8 and R9 together are part of a 5-, 6- or 7-membered heterocyclic ring;
or their pharmaceutically tolerable salts;
(HOE96/F 226)
be) phenyl-substituted alkenylcarboxylic acid guanidines of the formula I

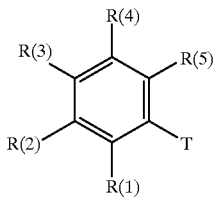

in which:
T is

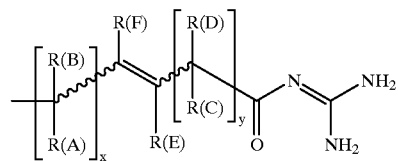

R(A) is hydrogen, F, Cl, Br, I, CN, OH, OR(6), $(C_1-C_4)$-alkyl, $O_r(CH_2)_aC_bF_{2b+1}$, $(C_3-C_8)$-cycloalkyl or NR(7)R(8)
  r is zero or 1;
  a is zero, 1, 2, 3 or 4;
  b is 1, 2, 3 or 4;
  R(6) is $(C_1-C_4)$-alkyl, $(C_1-C_4)$-perfluoroalkyl, $(C_3-C_6)$-alkenyl, $(C_3-C_8)$-cycloalkyl, phenyl or benzyl,
    where the phenyl ring is not substituted or substituted by 1–3 substituents selected from the group consisting of F, Cl, CF$_3$, methyl, methoxy and NR(9)R(10);
  R(9) and R(10) are H, $(C_1-C_4)$-alkyl or $(C_1-C_4)$-perfluoroalkyl;
  R(7) and R(8) independently of one another are defined as R(6); or R(7) and R(8) together are 4 or 5 methylene groups, of which one CH$_2$ group can be replaced by oxygen, sulfur, NH, N—CH$_3$ or N-benzyl;
R(B), R(C) and R(D) independently are as defined for R(A);
x is zero, 1 or 2;
y is zero, 1 or 2;
R(F) is hydrogen, F, Cl, Br, I, CN, OR(12), $(C_1-C_8)$-alkyl, $O_p(CH_2)_fC_gF_{2g+1}$, $(C_3-C_8)$-cycloalkyl or $(C_1-C_9)$-heteroaryl;
  p is zero or 1;
  f is zero, 1, 2, 3 or 4;
  g is 1, 2, 3, 4, 5, 6, 7 or 8;
  R(12) is $(C_1-C_8)$-alkyl, $(C_1-C_4)$-perfluoroalkyl, $(C_3-C_8)$-alkenyl, $(C_3-C_8)$-cycloalkyl, phenyl or benzyl,
    where the phenyl ring is not substituted or substituted by 1–3 substituents selected from the group consisting of F, Cl, CF$_3$, methyl, methoxy and NR(13)R(14);
  R(13) and R(14) are H, $(C_1-C_4)$-alkyl or $(C_1-C_4)$-perfluoroalkyl;
R(E) independently is as defined for R(F);
R(1) independently is as defined for T; or
R(1) is hydrogen, —$O_kC_mH_{2m+1}$, —$O_n(CH_2)_pC_qF_{2q+1}$, F, Cl, Br, I, CN, —(C=O)—N=C(NH$_2$)$_2$, —SO$_r$R(17), —SO$_2$,NR(31)R(32); —$O_u$(CH$_2$)$_vC_6H_5$, —$O_{u2}$—$(C_1-C_9)$-heteroaryl or —$S_{u2}$—$(C_1-C_9)$-heteroaryl;
  k is zero or 1;
  m is zero, 1, 2, 3, 4, 5, 6, 7 or 8;
  n is zero or 1;
  p is zero 1, 2, 3 or 4;
  q is 1, 2, 3, 4, 5, 6, 7 or 8;
  r is zero, 1, 2;
  r is zero, 1, 2;
  R(31) and R(32) independently of one another are hydrogen, $(C_1-C_8)$-alkyl or $(C_1-C_8)$-perfluoroalkyl; or
  R(31) and R(32) together are 4 or 5 methylene groups, of which one CH$_2$ group can be replaced by oxygen, S, NH, N—CH$_3$ or N-benzyl;
  R(17) is $(C_1-C_8)$-alkyl;
  u is zero or 1;
  u2 is zero or 1;
  v is zero, 1, 2, 3 or 4;
    where the phenyl ring is not substituted or substituted by 1–3 substituents selected from the group consisting of F, Cl, CF$_3$, methyl, methoxy, —(CH$_2$)$_w$NR(21)R(22), NR(18)R(19) and $(C_1-C_9)$-heteroaryl;
    R(18), R(19), R(21) and R(22) independently of one another are $(C_1-C_4)$-alkyl or $(C_1-C_4)$-perfluoroalkyl;
  w is 1, 2, 3 or 4;
    where the heterocycle of the $(C_1-C_9)$-heteroaryl is unsubstituted or substituted by 1–3 substituents selected from the group consisting of F, Cl, CF$_3$, methyl or methoxy;
R(2), R(3), R(4) and R(5) independently of one another are as defined for R(1), or
R(1) and R(2) or R(2) and R(3) in each case together are —CH=CH—CH=CH—,
  which is unsubstituted or substituted by 1–3 substituents selected from the group consisting of F, Cl, CF$_{31}$ methyl, methoxy, —(CH$_2$)$_{w2}$NR(24)R(25) and NR(26)R(27);
  R(24), R(25), R(26) and R(27) are H, $(C_1-C_4)$-allyl or $(C_1-C_4)$-perfluoroalkyl;
  w2 is 1, 2, 3 or 4;
the radical T being present in the molecule at least twice, but at most three times;
and their pharmaceutically tolerable salts;
(HOE 97/F 082)
bf) benzoylguanidines of the formula I

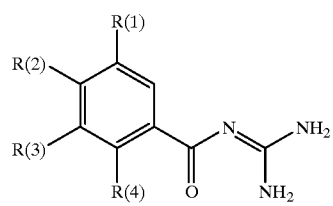

in which:
R(1) is CF$_3$;
one of the substituents R(2) and R(3) is hydrogen;
and the other substituent R(2) and R(3) in each case is —C(OH)(CH$_3$)—CH$_2$OH, —CH(CH$_3$)—CH$_2$OH or —C(OH)(CH$_3$)$_2$;
R(4) is methyl, methoxy, Cl or CF$_3$;
and their pharmaceutically tolerable salts;
(DE 195 02 895, DE 44 30 212, EP 667 341, DE 44 04 183, EP 708 088, EP 723 963, EP 0 694 537, DE 44 21 495, EP 699 660, EP 699 663, EP 699 666, DE 43 37 611, EP 0719 766, WO 94/26709, WO 96 04 241, EP 726 254, U.S. Pat. No. 4,251,545, DE 35 02 629, WO 84/00875, Kumamoto et al., Pharm. Bull. [1966], 7–13; U.S. Pat. No. 3,780,027, JP 8225513; EP 743 301)

II. Also Suitable are Compounds of the Formula

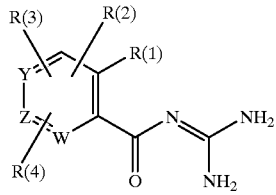

in which:
- W, Y and Z are a nitrogen atom or a carbon atom substituted by R(2) or R(3) or R(4);
- R(1) is hydrogen, A, Hal, —CF$_3$, —CH$_2$F, —CHF$_2$, —CH$_2$CF$_3$, —C$_2$F$_5$, —CN, —NO$_2$, -ethynyl, or an X—R';
- A is alkyl having 1 to 6 carbon atoms;
- Hal is F, Cl, Br or I;
- X is oxygen, S or NR";
  - R" is hydrogen, A or a cyclic methylene chain having 3 to 7 carbon atoms;
- R' is H, A, HO—A—, HOOC—A—, (C$_3$–C$_7$)-cycloalkyl, (C$_6$–C$_8$)-cycloalkylalkyl, CF$_3$, CH$_2$F, CHF$_2$, CH$_2$—CF$_3$, Ph, —CH$_2$—Ph or Het;
  - Ph is phenyl, naphthyl or biphenylyl which is unsubstituted or mono-, di- or trisubstituted by A, OA, NR'R", Hal, CF$_3$;
  - Het is a mono- or binuclear saturated, unsaturated or aromatic heterocycle having 1 to 4 nitrogen, oxygen and/or sulfur atoms,
    which is unsubstituted or mono-, di- or trisubstituted by Hal, CF$_3$, A, OH, OA, —X—R', —CN, —NO$_2$, and/or carbonyl oxygen,
    where Het is bonded via N or an alkylene chain C$_m$H$_{2m}$, where m=zero to 6; or
  - R' and R" together are alkylene having 4–5 carbon atoms, in which one CH$_2$ group can also be replaced by oxygen, S, NH, N—A, N—Ph and N—CH$_2$—Ph;
- R(2) and R(3) independently of one another are hydrogen, Hal, A, HO—A—, X—R', —C(=N—OH)—A, A—O—CO—(C$_1$–C$_4$)-alkyl-, CN, NO$_2$, COOH, halogen-substituted A, in particular CF$_3$, CH$_2$F, CHF$_2$, C$_2$F$_5$, CH$_2$CF$_3$, or S(O)$_n$R'";
  - R'" is A, Ph or -Het;
  - n is zero, 1 or 2; or
- R(2) and R(3) independently of one another are SO$_2$NR'R", Ph or —O—Ph, —O—CH$_2$—Ph, —CO—A, —CHO, —COOA, —CSNR'R", CONR'R", —CH=CH—COOH, —CH=CH—COOA, indenyl, indanyl, decahydronaphthyl, cyclopentenyl, dihydrothienyl, dihydrofuryl, heterobicyclyl, alkylthienyl, halothienyl, haloalkylthienyl, acylthienyl, halofuryl, haloalkylfuryl or pyrrolyl; or
- R(2) and R(3) independently of one another are R(5)—O—;
  - R(5) is hydrogen, A, (C$_1$–C$_6$)-alkenyl or (C$_3$–C$_7$)-cycloalkyl;
- R(4) is Ph, Het, —O-Het; CF$_3$, S(O)$_n$R'", —SO$_2$NR'R", alk;

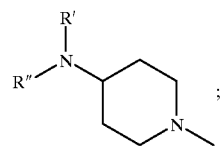

or
two of the substituents R(1) to R(4) together are a group —O—CR(6)R(7)CO—NR(8)—, or

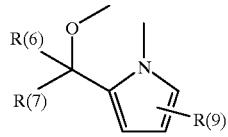 or 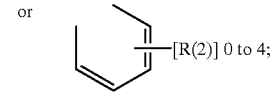

where R(2) has the meaning indicated;
R(6), R(7), R(8) and R(9) independently of one another are H or A; or
R(8) is (C$_5$–C$_7$)-cycloalkyl; or
R(9) is cyano;
alk is straight-chain or branched (C$_1$–C$_8$)-alkyl or (C$_3$–C$_8$)-cycloalkyl,
  which is unsubstituted or mono-, di- or trisubstituted by A; or
alk is an ethenyl or ethynyl radical which is substituted by H, A, Ph or Het.
[DE 41 27 026, DE 43 37 609, JP 07025768, Edward J. Cragoe, Jr., DIURETICS (Chemistry, Pharmacology and Medicine), J. Wiley & Sons (1983), 303–341]

III. Compounds of the Formula

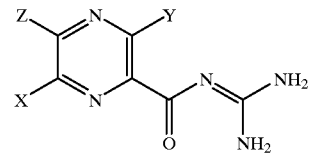

in which:
- X is H, Hal, (Hal)$_3$C—, (C$_1$–C$_6$)-alkyl, (C$_3$–C$_6$)-cycloalkyl, substituted phenyl, (C$_1$–C$_5$)-alkyl-S— or (C$_1$–C$_5$)-alkyl-SO$_2$—;
- Y is NH$_2$ or substituted amino; or
- X and Z together are a —(CH$_2$)$_4$— or a 1,3-butadienylene chain; or
- Z is H, Hal, OH, HS, (C$_1$–C$_5$)-alkyl, (C$_3$–C$_6$)-cycloalkyl, substituted phenyl; or
- Z is an amino group —NR(1)R(2);
  - R(1) is H, straight- or branched-chain, optionally substituted (C$_1$–C$_8$)-alkyl,
    which can be interrupted by oxygen; or
  - R(1) is (C$_3$–C$_8$)-alkenyl, (C$_3$–C$_8$)-alkynyl, (C$_3$–C$_7$)-cycloalkyl or OH-substituted phenyl or OH-substituted phenyl-(C$_1$–C$_4$)-alkyl or OH-substituted (C$_3$–C$_7$)-cycloalkyl;
  - R(2) is 1-morpholino, hydrogen or a straight or branched (C$_1$–C$_8$)-alkyl chain,
    which can be interrupted by oxygen or an amino group,
    which straight or branched (C$_1$–C$_8$)-alkyl chain is unsubstituted or substituted by a substituted or unsubstituted mono- or polynuclear heterocycle which contains nitrogen, oxygen or sulfur atoms; or
which alkyl chain is substituted by phenyl,
  optionally mono- or polysubstituted by $(C_1-C_4)$-alkoxy, optionally substituted by OH, alkylamino, alkyl or phenyl; or
  by an aminocarbonyl group, or
  by hydroxyl or $(C_1-C_4)$-alkoxy groups, or
R(2) is phenyl,
  unsubstituted or substituted by alkyl, alkoxy, an amino group, which as substituents carries:
  H, a mono- or polynuclear heterocycle which contains nitrogen, oxygen or sulfur atoms,
    which is unsubstituted or substituted by H, Hal or $(C_1-C_4)$-alkyl;
  a phenyl radical,
    unsubstituted or substituted by a substituent selected from the group consisting of $(C_1-C_4)$-alkyl, $(C_1-C_4)$-alkoxy, Hal and OH; or
R(2) is 1-piperidino,
  unsubstituted or substituted in the 4-position by an acyl radical of an aliphatic, alicyclic, aromatic or heteroaromatic carboxylic acid, $(C_1-C_8)$-alkyl, which for its part can be substituted by OH or $(C_1-C_4)$-alkoxy or a $(C_1-C_4)$-alkoxy-substituted phenyl radical; or
R(2) is amidino,
  which is unsubstituted or substituted by phenyl, which is unsubstituted or substituted by Hal or alkyl; or
R(2) is an acyl radical of an aliphatic, alicyclic, aromatic or heteroaromatic carboxylic acid, or
R(2) is a $(C_1-C_8)$-alkyl chain, which can be substituted by a phenyl radical carrying OH, alkoxy or alkyl radicals, or
R(1) and R(2) together with the nitrogen atom to which they are bonded, are a piperazine ring,
  which is unsubstituted or via a $(C_1-C_6)$-methylene chain carries a mono- or polynuclear heterocycle, which contains nitrogen, oxygen or sulfur,
Hal is F, Cl, Br or I.
(EP 708 091, EP 622 356, JP 5-125085)

IV. Likewise Suitable are Indoloylguanidine Derivatives of the Formula

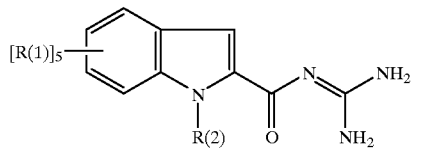

in which
R(2) is hydrogen, unsubstituted or substituted $(C_1-C_8)$-alkyl, $(C_3-C_7)$-cycloalkyl, OH, $(C_1-C_6)$-alkyl-O—, an aromatic radical or a group —CH$_2$—R(20);
R(20) is $(C_2-C_6)$-alkenyl or $(C_2-C_6)$-alkynyl;
R(1) is 1 to 5 identical or different substituents, which are: hydrogen, unsubstituted or substituted $(C_1-C_8)$-alkyl, $(C_2-C_6)$-alkenyl, $(C_2-C_6)$-alkynyl, $(C_3-C_7)$-cycloalkyl, halogen, —NO$_2$, $(C_2-C_8)$-alkanoyl, arylalkanoyl having up to 10 carbon atoms, aroyl having up to 11 carbon atoms, —COOH, $(C_2-C_6)$-alkoxycarbonyl, an aromatic group or one of the following mentioned groups: —OR(3), —NR(6)R(7) or —S(O)$_n$R(40);

R(3) is hydrogen, $(C_1-C_8)$-alkyl, substituted $(C_1-C_8)$-alkyl, $(C_3-C_7)$-cycloalkyl, an aromatic radical or a group —CH$_2$—R(30) R(30) is alkenyl or alkynyl;
R(6) and R(7) independently of one another are hydrogen, unsubstituted or substituted $(C_1-C_8)$-alkyl, $(C_3-C_7)$-cycloalkyl, $(C_2-C_8)$-alkanoyl, an arylalkanoyl group having up to 10 carbon atoms, an aroyl group having up to 11 carbon atoms, an aromatic group or —CH$_2$—R(60);
  R(60) is $(C_2-C_6)$-alkenyl or $(C_2-C_6)$-alkynyl; or
R(6) and R(7) together with the nitrogen atom are a 5–7-membered cyclic amine, which can additionally contain further heteroatoms in the ring;
n is zero, 1 or 2;
R(40) is unsubstituted or substituted $(C_1-C_8)$-alkyl, or an aromatic group, or a group

A is oxygen, —S(O)$_n$— or —N(R50)—;
R(50) is hydrogen or $(C_1-C_8)$-alkyl;
R' is hydrogen, unsubstituted or substituted $(C_1-C_8)$-alkyl,
  in which the ring represents a saturated 3–8-membered heterocycle having a nitrogen atom,
said substituted alkyl carries one or more groups selected from the group consisting of halogen, —OH, $(C_1-C_6)$-alkoxy, —CN, —COOH, $(C_2-C_6)$-alkoxycarbonyl, $(C_2-C_8)$-alkanoyl, arylalkanoyl having up to 10 carbon atoms, aroyl having up to 11 carbon atoms, an aromatic group, —CONR(4)R(5),
R(4) and R(5) identically or differently are hydrogen or $(C_1-C_8)$-alkyl; or
R(4) and R(5) are connected to one another and together form a 5–7-membered cyclic amine which can additionally contain further heteroatoms in the ring,
or said substituted alkyl carries a group

in which:
E is a nitrogen atom or a CH group;
R" is hydrogen, $(C_1-C_8)$-alkyl which is unsubstituted or substituted by OH, $(C_1-C_6)$-alkoxy, —CN, —COOH, $(C_2-C_6)$-alkoxycarbonyl, $(C_2-C_8)$-alkanoyl, aralkanoyl having up to 10 carbon atoms, aroyl having up to 11 carbon atoms, an aromatic group, —NR(6)R(7), —CONR(4)R(5);
R(4) and R(5) independently of one another are hydrogen or $(C_1-C_8)$-alkyl;
where the cyclic system of the formula

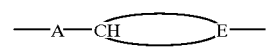

is a 3–8-membered saturated aliphatic or heterocyclic ring system having a nitrogen atom,
and where the aromatic groups mentioned are an aryl radical having up to 10 carbon atoms, a 5- or 6-membered heteroaryl radical having 1–4 nitrogen atoms, a 5- or 6-membered heteroaryl group containing 1 or 2 nitrogen atoms and a heteroatom which is oxygen or sulfur, or furyl, and where the aryl radicals mentioned can be unsubstituted or substituted by unsubstituted ($C_1$–$C_8$)-alkyl or substituted ($C_1$–$C_8$)-alkyl, halogen, —$NO_2$, ($C_2$–$C_6$)-alkoxycarbonyl, COOH, —OR(3), NR(6)R(7), —CONR(4)R(5), —$SO_2$NR(6)R(7) or $S(O)_n$R(40), where R(1) and the guanidinocarbonyl radical can be in any desired position of the 5- or 6membered ring of the indole system, and the appropriate pharmaceutically tolerable salts;

(WO 95 04052)

V. Additionally Suitable are Heterocyclic Guanidine Derivatives of the Formula

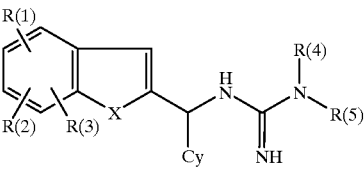

in which:

X is —O—, —S—, —NH—, —N[($C_1$–$C_4$)-alkyl]— or —N(phenyl)-;

R(1), R(2) and R(3) are hydrogen, halogen, ($C_1$–$C_4$)-alkyl, ($C_1$–$C_4$)-alkyl-O—, phenyl, benzyl; or two of the substituents R(1), R(2) and R(3) together with one side of the benzo system are a 4–6membered carbocyclic ring;

R(4) and R(5) independently of one another are hydrogen, ($C_1$–$C_{12}$)-alkyl, benzhydryl, aralkyl, which is unsubstituted or substituted by one or more substituents from the groups halogen, ($C_1$–$C_4$)-alkyl, ($C_1$–$C_4$)-alkyl-O— or —$CF_3$, —$(CH_2)_m$—$CH_2$—T, m is zero to 3;

T is —CO—O—T(1);

T(1) is hydrogen or ($C_1$–$C_4$)-alkyl;

Cy is a benzo-fused unsaturated or dihydro-5-membered ring heterocycle

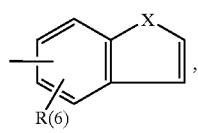

a pyrazole or imidazole ring of the formula

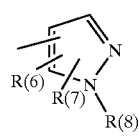

or

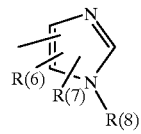

a naphthyl radical or a dihydro- or tetrahydronaphthyl radical

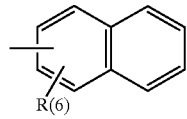

a 2-, 3- or 4-pyridyl radical

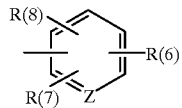

Z is N— or CH;

a thienyl radical

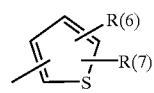

R(6) is hydrogen, halogen, hydroxyl, ($C_1$–$C_{10}$)-alkyl, ($C_1$–$C_{10}$)-alkyl-O—, phenoxy, ($C_1$–$C_{10}$)-alkyloxymethyloxy- or —$(O)_n$S—R(9);

R(9) is ($C_1$–$C_{10}$)-alkyl, thienyl, pyridyl, thiazolyl, thiadiazolyl, imidazolyl, pyrazolyl or phenyl, each of which is unsubstituted or mono- or disubstituted by halogen, ($C_1$–$C_4$)-alkyl or ($C_1$–$C_4$)-alkyl-O—;

R(7) and R(8) is hydrogen, halogen, hydroxyl, ($C_1$–$C_{10}$)-alkyl, ($C_1$–$C_{10}$)-alkyl-O—, phenyl, phenoxy or ($C_1$–$C_{10}$)-alkoxymethyloxy; or Cy is phenyl, which is unsubstituted or mono- or disubstituted by halogen, ($C_1$–$C_4$)-alkyl or ($C_1$–$C_4$)-alkyl-O—; or Cy is —Gr—Am;

Gr is —R(13)—R(12)—$(CH_2)_q$—C[W][W(1)]—$(CH_2)_{q'}$—; R(13)R(14)— or —R(15)—;

R(12) is a single bond, —O—, —$(O)_n$S—, —CO— or —CONH—;

R(13) is a single bond, phenyl, thienyl, pyridyl, thiazolyl, thiadiazolyl, imidazolyl or pyrazolyl;

R(14) is a single bond or $SO_2$—;

R(15) is ($C_2$–$C_{10}$)-alkenyl- or ($C_2$–$C_{10}$)-alkynyl;

W and W(1) independently of one another are hydrogen, ($C_1$–$C_4$)-alkyl; or

W and W(1) cyclically connected to one another are a ($C_3$–$C_8$)-hydrocarbon ring;

q and q' are zero to 9;

Am is —NR(10)R(11);
R(10) is hydrogen, $(C_1-C_4)$-alkyl or benzyl,
R(11) is $(C_1-C_4)$-alkyl, phenyl or benzyl; or
R(10) and R(11) together are a $(C_3-C_{10})$-alkylene group,
which is unsubstituted or substituted by —COOH, $(C_1-C_5)$-alkoxycarbonyl, $(C_2-C_4)$-hydroxylalkylene or benzyl; or
Am is pyrrolyl, pyridyl, pyrazolyl, morpholinyl, dihydropyridyl, tetrahydropyridyl, quinmuclidinyl, imidazolyl, 3-azabicyclo[3.2.1]octyl,
which is unsubstituted or substituted by $(C_1-C_4)$-alkyl, or
Am is azabicyclo[3.2.2]nonyl; or
Am is a piperazine group of the formula

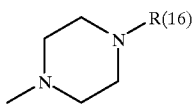

R(16) is hydrogen, $(C_1-C_4)$-alkyl, $(C_3-C_6)$-cycloalkyl, phenyl, tolyl, methoxyphenyl, halophenyl, diphenylmethylene, benzyl or pyridyl; or
Am is an azido group —(O)$_t$(CH$_2$)$_q$—C[W][W(1)]—(CH$_2$)$_{q'}$—N$_3$;
t is zero or 1;
where W and W(1) have the previously indicated meaning;
and the optical enantiomers and the pharmacologically tolerable salts;
VI. Furthermore Suitable are the Guanidine Compounds as Described in EP-743 301 (DE 195 17 848), EP 758 644 (DE 195 29 612), EP 760 365 (DE 195 31 138)

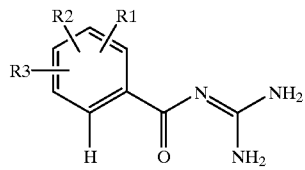

where R1=R2 is H, halo, alkyl, CN, NO$_2$, perfluoroalkyl, SO$_n$CF$_3$; R3=CH=CH$_2$, CH$_2$-CH=CH$_2$, CH$_2$-CH$_2$—CH=CH$_2$, cycloalkenyl, cycloalkenylalkyl; R4=alkyl, (substituted) phenyl,
or as described in DE 195 48 708, WO 97 25 310, WO 97 27 183, DE 196 01 303, EP 787 728, JP 82 25 513, JP 090 59 245, JP 090 67 332, JP 090 67 340, WO 97 11 055 and EP 743 301.

Examples of classes of active compounds having cardiovascular activity which can be combined advantageously with NHE inhibitors therapeutically are beta-receptor blockers, calcium antagonists, angiotensin-converting enzyme inhibitors, angiotensin receptor blockers, loop diuretics, thiazide diuretics, potassium-sparing diuretics, aldosterone antagonists, such as are employed, for example, in lowering of the blood pressure, and also cardiac glycosides or other agents increasing the contractile force in the treatment of cardiac insufficiency and of congestive heart failures, and also antiarrhythmics of the classes I–IV, nitrates, K$_{ATP}$ openers, K$_{ATP}$ blockers, inhibitors of the veratridine-activatable sodium channel, etc. For example, the following are thus suitable: the beta-blockers propanolol, atenolol, metoprolol; the calcium antagonists diltiazem hydrochloride, verapamil hydrochloride, nifedipine; the ACE inhibitors captopril, enalapril; the angiotensin receptor antagonist losartan; the loop diuretics furosemide, piretanide, torasemide; the thiazide diuretics hydrochlorothiazide, metolazone, indapamide; the potassium-sparing diuretics amiloride, triamterene, spironolactone; the cardiac glycosides digoxin, digitoxin, strophanthin; the antiarrhythmics amiodarone, sotalol, bretylium, flecainide; the nitrate glycerol trinitrate; the K$^+$(ATP) openers cromakalim, lemakalim, nocorandil, pinacidil, minoxidil; the inhibitors of the veratridine-activatable Na$^+$ channel.

An example of such a particularly advantageous combination component with NHE inhibitors are blockers of the non-inactivating sodium channel (veratridine-activatable sodium channel). When the two classes of active compounds are therapeutically administered as a combination, they surprisingly show the abovementioned synergistic effects in the treatment of symptoms resulting from ischemic conditions and reperfusion events. The combinations of an NHE inhibitor with a blocker of the non-inactivating sodium channel (veratridine-activatable sodium channel) are thus outstandingly suitable for infarct and reinfarct prophylaxis and infarct treatment and also for the treatment of angina pectoris and the inhibition of is chemically induced cardiac arrhythmias, tachycardia and the formation and maintenance of ventricular fibrillation, the combinations of an NHE inhibitor with a blocker of the non-inactivating sodium channel also preventively inhibiting or greatly decreasing the pathophysiological processes in the formation of ischemically induced damage. Because of their enhanced protective actions against pathological hypoxic and ischemic situations, the combinations according to the invention of an NHE inhibitor with a blocker of the non-inactivating sodium channel can be used, as a result of enhanced inhibition of the Na$^+$ influx into the cell, as pharmaceuticals for the treatment of all acute or chronic damage induced by ischemia or diseases induced primarily or secondarily thereby. This relates to their use as pharmaceuticals for surgical interventions, e.g. in organ transplantation, where the combinations of an NHE inhibitor with a blocker of the non-inactivating sodium channel can be used both for the protection of the organs in the donor before and during removal, for the protection of removed organs, for example, also during storage thereof in physiological bath fluids, and also during transfer to the recipients body. The combinations of an NHE inhibitor with a blocker of the non-inactivating sodium channel are likewise valuable, protectively acting pharmaceuticals when carrying out angioplastic surgical interventions, for example on the heart, and also on peripheral vessels. In accordance with their protective action against ischemically induced damage, the combinations of an NHE inhibitor with a blocker of the non-inactivating sodium channel are also suitable as pharmaceuticals for the treatment of ischemias of the nervous system, in particular of the central nervous system, where they are suitable for the treatment of stroke or of cerebral edema. Moreover, the combinations according to the invention of an NHE inhibitor with a blocker of the non-inactivating sodium channel are also suitable for the treatment of forms of shock, such as, for example, of allergic, cardiogenic, hypovolemic and bacterial shock.

Thus, for example, it has surprisingly been found that the combination of the NHE inhibitor cariporide (HOE 642)

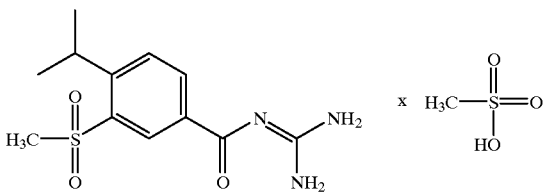

described, for example, in U.S. patent U.S. Pat. No. 5,591, 754, with the inhibitor of the non-inactivating sodium channel (veratridine-activatable sodium channel) R56865 [N-[1-[4-(4-fluorophenoxy)butyl]-4-piperdinyl]-N-methyl-2-benzothiazolamine (see Verdonck F, Bielen F. Ver Donck L: Preferential block of the veratridine-induced, noninactivating $Na^+$ current by R56865 in single cardiac Purkinje cells. Eur J Pharmacol 1991; 203; 371–378)] in a model of experimental cardiac infarct in rats showed an activity which is considerably greater than additive activity. The reduction of the size of the infarct which was obtained using the combination of cariporide and R56865 exceeded the maximum effect of the individual substances in this model by far. The study was carried out as described below.

Preparation of the Animals

Male rats having a body weight of 280 to 410 g were classed into four groups and anaesthetized. The thorax was opened close to the sternum, a silk thread (Ethicon$^R$; 1.0 metric, 5-0) was placed around left coronary artery and the two loose ends of the thread were pulled through a small plastic tube.

For administration of substance, a catheter was placed into the left jugular vein. The systemic blood pressure was recorded in the left carotid artery using a pressure recorder (Combitrans$^R$, B. Braun Melsungen AG) and the ECG was registered using subcutaneous electrodes. After digital conversion, the data were registered in a computer and the ECG was evaluated in accordance with the guidelines of the Lambeth Convention (6. Walker M J A, Curtis M J, Hearse D J, Campbell R W F, Janse M J, Yellon D M, Cobbe S M, Cokes S J, Harness J B, Harron D W G, Higgins S J, Julian D G, Lab M J, Manning A S, Northover B J, Parraft J R, Riemersma R A, Rieva E, Russell D G, Sheridan D J, Winslow E, Woodward B: The Lambeth convention: Guidelines for the study of arrhythmias in ischemia, infarction and reperfusion. Cardiovasx. Res 1988; 22: 447–455).

Protocol of the Experiment

Hoe 642 was dissolved in doubly distilled water and R56865 in tartaric acid (0.6%), dilution was carried out using doubly distilled water, and 4% of mannitol were added. After the preparation of the animals, the substances were administered intraveneously on their own or in combination. The control animals were only given the solvent. The volume of the injection was 1 ml per kg of body weight. Five minutes later, the silk thread was constricted by moving the plastic tube forward, and the coronary artery was closed for one hour. The plastic tube was fixed by a clamp. After re-opening of the coronary artery, the tissue was reperfused for two hours.

Determination of the Size of the Infarct

The coronary artery which had been tied off was closed again, and ink was injected into the left ventricle of heart via the apex of the heart to mark the heart tissue which had been supplied normally with blood. The animals were sacrificed, the hearts were removed and the left ventricle of heart was prepared and cut into slices vertically to the axis of the heart. The slices were washed in sodium chloride solution and subsequently incubated in triphenyltetrazolium chloride at 37° C. for 5–7 minutes to stain the tissue that was still live. The slices were subsequently weighed and measured planimetrically (Imaging Res. Inc. Brock. University, St. Catherines, Ontario, Canada, Phoenix Technologies, Matrox Electronic Systems OS/2). Determined were: firstly, the size of the tissue which had been supplied normally with blood, secondly, the area which had not been supplied with blood after constriction of the loop (risk area), and thirdly the size of the area in which the cells had died (size of infarct).

The statistical evaluation of the differences between the individual groups was carried out using Student's t-test.

Results

Administration of the substances did not effect blood flow in the tissue which was supplied normally with blood. Consequently, there was no change in the size of the risk area of, on average, 59.3% of the left ventricle. In the control group, necrosis of the tissue occurred owing to the one-hour blockade of perfusion and reperfusion. In the control group, the size of infarct was 63.4±4.3% (n=8) of the risk area. Administration of 10 mg/kg of body weight of Hoe 642 reduced the size of infarct to 33.2±3.7% (n=7), and administration of 3 mg/kg of body weight of R56865 reduced the size of infarct to 38.9±3.1% (n=8). Using the combination of the two substances in the dosage in question, however, it was possible to reduce the infarct to 10.5±2.6% (n=10) of the risk area. All figures given are mean±S.E.M.

What is claimed is:

1. A pharmaceutical composition comprising an inhibitor of the $Na^+/H^+$ exchanger and a substance having cardiovascular activity, the inhibitor of the $Na^+/H^+$ exchanger being chosen from benzoylguanidines of formula (I):

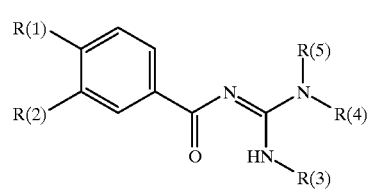

wherein:
R(1) or R(2) is R(6)—S(O)$_n$— or R(7)R(8)N—O$_2$S—;
and the other substituent R(1) or R(2) in each case is H, F, Cl, Br, ($C_1$–$C_4$)-alkyl, ($C_1$–$C_4$)-alkoxy or phenoxy, which is unsubstituted or substituted by 1–3 substituents chosen from fluorine, chorine, methyl and methoxy;
or the other substituent R(1) or R(2) in each case is R(6)—S(O)$_n$ or R(7)R(8)N—;
n is zero, 1 or 2;
R(6) is ($C_1$–$C_6$)-alkyl, ($C_5$–$C_7$)-cycloalkyl, cyclopentylmethyl, cyclohexylmethyl or phenyl, which is unsubstituted or substituted by 1–3 substituents chosen from fluorine, chlorine, methyl and methoxy;
R(7) and R(8) identically or differently are H or ($C_1$–$C_6$)-alkyl; or
R(7) is phenyl-(CH$_2$)$_m$;
m is 1–4; or
R(7) is phenyl,
which is unsubstituted or substituted by 1–2 substituents chosen from fluorine, chlorine, methyl and methoxy; or
R(7) and R(8) together are a straight-chain or branched ($C_4$–$C_7$)-chain, where the chain is uninterrupted or interrupted by O, S or NR(9);

R(9) is H or methyl; or

R(7) and R(8) together with the nitrogen atom to which they are bonded, are a dihydroindole, tetrahydroquinoline or tetrahydroisoquinoline system;

R(3), R(4) and R(5) independently of one another are H or ($C_1$–$C_2$)-alkyl, or R(3) and R(4) together are a ($C_2$–$C_4$)-alkylene chain; or R(4) and R(5) together are a ($C_4$–$C_7$)-alkylene chain;

or a pharmaceutically tolerable salt thereof.

2. The pharmaceutical composition according to claim 1, wherein the substance having cardiovascular activity is an aldosterone antagonist.

3. The pharmaceutical composition according to claim 1, wherein the substance having cardiovascular activity is a medicament for lowering blood pressure.

4. The pharmaceutical composition according to claim 1, wherein the substance having cardiovascular activity is a beta-receptor blocker.

5. The pharmaceutical composition according to claim 1, wherein the substance having cardiovascular activity is a calcium antagonist.

6. The pharmaceutical composition according to claim 1, wherein the substance having cardiovascular activity is an angiotensin conversion enzyme inhibitor.

7. The pharmaceutical composition according to claim 1, wherein the substance having cardiovascular activity is a diuretic.

8. The pharmaceutical composition according to claim 1, wherein the substance having cardiovascular activity is a medicament that strengthens the contractile force of the heart.

9. The pharmaceutical composition according to claim 1, wherein the substance having cardiovascular activity is a cardiac glycoside.

10. The pharmaceutical composition according to claim 1, wherein the substance having cardiovascular activity is an antiarrhythmic.

11. The pharmaceutical composition according to claim 10, wherein the antiarrhythmic is an antiarrhythmic of the classes I, II, III or IV.

12. The pharmaceutical composition according to claim 1, wherein the substance having cardiovascular activity is a nitrate.

13. The pharmaceutical composition according to claim 1, wherein the substance having cardiovascular activity is an opener of the K(ATP) channel.

14. The pharmaceutical composition according to claim 1, wherein the substance having cardiovascular activity is a K(ATP) blocker.

15. The pharmaceutical composition according to claim 1, comprising, as the inhibitor of the $Na^+/H^+$ exchanger, a benzoylguanidine of the formula

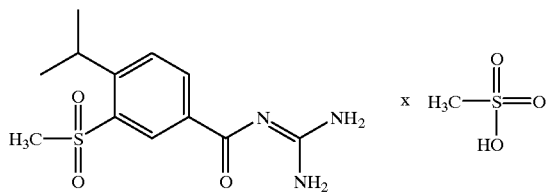

in combination with an inhibitor of the non-inactivating sodium channel.

16. A commercial pack, comprising as pharmaceutically active compound an inhibitor of the $Na^+/H^+$ exchanger and another substance having cardiovascular activity, together with instructions for the combined use of these active compounds for simultaneous or separate use or use at graded time intervals in the treatment or prophylaxis of cardiovascular diseases, wherein the inhibitor of the $Na^+/H^+$ exchanger is chosen from benzoylguanidines of formula (I):

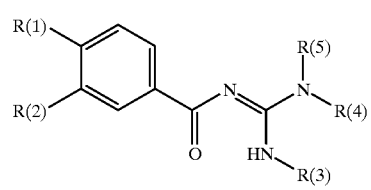

I wherein:

R(1) or R(2) is R(6)—S(O)$_n$— or R(7)R(8)N—O$_2$S—;

and the other substituent R(1) or R(2) in each case is H, F, Cl, Br, ($C_1$–$C_4$)-alkyl, ($C_1$–$C_4$)-alkoxy or phenoxy, which is unsubstituted or substituted by 1–3 substituents chosen from fluorine, chorine, methyl and methoxy;

or the other substituent R(1) or R(2) in each case is R(6)—S(O)$_n$ or R(7)R(8)N—;

n is zero, 1 or 2;

R(6) is ($C_1$–$C_6$)-alkyl, ($C_5$–$C_7$)-cycloalkyl, cyclopentylmethyl, cyclohexylmethyl or phenyl, which is unsubstituted or substituted by 1–3 substituents chosen from fluorine, chlorine, methyl and methoxy;

R(7) and R(8) identically or differently are H or ($C_1$–$C_6$)-alkyl; or

R(7) is phenyl-(CH$_2$)$_m$;

m is 1–4; or

R(7) is phenyl, which is unsubstituted or substituted by 1–2 substituents chosen from fluorine, chlorine, methyl and methoxy; or R(7) and R(8) together are a straight-chain or branched ($C_4$–$C_7$)-chain, where the is uninterrupted or interrupted by O, S or NR(9);

R(9) is H or methyl; or

R(7) and R(8) together with the nitrogen atom to which they are bonded, are a dihydroindole, tetrahydroquinoline or tetrahydroisoquinoline system;

R(3), R(4) and R(5) independently of one another are H or ($C_1$–$C_2$)-alkyl, or R(3) and R(4) together are a ($C_2$–$C_4$)-alkylene chain; or R(4) and R(5) together are a ($C_4$–$C_7$)-alkylene chain;

or a pharmaceutically tolerable salt thereof.

17. A method for treating hypertension under cardioprotective conditions, comprising administering to a patient in need thereof the pharmaceutical composition according to claim 3.

18. A method for treating hypertension or arrhythmia under cardioprotective conditions, comprising administering to a patient in need thereof the pharmaceutical composition according to claim 4.

19. A method for treating hypertension under cardioprotective conditions, comprising administering to a patient in need thereof the pharmaceutical composition according to claim 5.

20. A method for treating hypertension under cardioprotective conditions, comprising administering to a patient in need thereof the pharmaceutical composition according to claim 6.

21. A method for treating hypertension or cardiac insufficiency under cardioprotective conditions, comprising administering to a patient in need thereof the pharmaceutical composition according to claim 7.

22. A method for treating cardiac insufficiency or congestive heart failure under cardioprotective conditions, comprising administering to a patient in need thereof the pharmaceutical composition according to claim 8.

23. A method for treating cardiac insufficiency or congestive heart failure under cardioprotective conditions, comprising administering to a patient in need thereof the pharmaceutical composition according to claim 9.

24. A method for treating cardiac arrhythmias of various genesis under cardioprotective conditions, comprising administering to a patient in need thereof the pharmaceutical composition according to claim 10.

25. A method for treating cardiac arrhythmias of various genesis under cardioprotective conditions, comprising administering to a patient in need thereof the pharmaceutical composition according to claim 11.

* * * * *

UNITED STATES PATENT AND TRADEMARK OFFICE
CERTIFICATE OF CORRECTION

PATENT NO. : 6,348,476 B1
DATED : February 19, 2002
INVENTOR(S) : Wolfgang Scholz et al.

It is certified that error appears in the above-identified patent and that said Letters Patent is hereby corrected as shown below:

Column 86,
Line 48, "chorine" should read -- chlorine --.

Column 88,
Line 22, "chorine" should read -- chlorine --.
Line 41, "the is" should read -- the chain is --.

Signed and Sealed this

Twenty-third Day of April, 2002

Attest:

JAMES E. ROGAN
Attesting Officer    Director of the United States Patent and Trademark Office